US008486681B2

(12) United States Patent
Svendsen et al.

(10) Patent No.: US 8,486,681 B2
(45) Date of Patent: *Jul. 16, 2013

(54) ALPHA-AMYLASE VARIANT WITH ALTERED PROPERTIES

(75) Inventors: Allan Svendsen, Horsholm (DK); Carsten Andersen, Vaerlose (DK); Thomas Thisted, Frederikssund (DK); Claus Von Der Osten, Lyngby (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 12/360,635

(22) Filed: Jan. 27, 2009

(65) Prior Publication Data

US 2009/0143270 A1   Jun. 4, 2009

Related U.S. Application Data

(63) Continuation of application No. 10/477,725, filed as application No. PCT/DK02/00319 on May 15, 2002, now Pat. No. 7,498,158.

(60) Provisional application No. 60/296,631, filed on Jun. 7, 2001, provisional application No. 60/302,391, filed on Jun. 29, 2001, provisional application No. 60/302,392, filed on Jul. 2, 2001, provisional application No. 60/302,395, filed on Jul. 2, 2001, provisional application No. 60/302,570, filed on Jul. 2, 2001, provisional application No. 60/326,750, filed on Oct. 3, 2001.

(30) Foreign Application Priority Data

| May 15, 2001 | (DK) | 2001 00760 |
| Jun. 22, 2001 | (DK) | 2001 00981 |
| Jun. 22, 2001 | (DK) | 2001 00982 |
| Jun. 26, 2001 | (DK) | 2001 00998 |
| Jun. 26, 2001 | (DK) | 2001 00999 |
| Oct. 2, 2001 | (DK) | 2001 01443 |

(51) Int. Cl.
| *C12N 9/26* | (2006.01) |
| *C12N 9/28* | (2006.01) |
| *C07K 14/00* | (2006.01) |
| *C11D 3/386* | (2006.01) |
| *C12P 21/00* | (2006.01) |
| *C12Q 1/40* | (2006.01) |

(52) U.S. Cl.
USPC ............ 435/201; 435/202; 435/22; 435/69.1; 530/350; 510/392

(58) Field of Classification Search
USPC .......... 435/201, 202, 69.1, 252.3, 350, 320.1, 435/22; 530/350; 536/23.2
See application file for complete search history.

(56) References Cited

U.S. PATENT DOCUMENTS

| 3,912,590 A | 10/1975 | Slott |
| 4,106,991 A | 8/1978 | Markussen |
| 4,316,956 A | 2/1982 | Lutzen |
| 4,335,208 A | 6/1982 | Norman |
| 4,435,307 A | 3/1984 | Barbesgaard |
| 4,519,934 A | 5/1985 | Eilertsen |
| 4,643,736 A | 2/1987 | Cholley |
| 4,661,452 A | 4/1987 | Markussen |
| 4,683,202 A | 7/1987 | Mullis |
| 4,689,297 A | 8/1987 | Good |
| 5,231,017 A | 7/1993 | Lantero |
| 5,324,649 A | 6/1994 | Arnold |
| 5,648,263 A | 7/1997 | Schulein |
| 5,691,178 A | 11/1997 | Schulein |
| 5,753,460 A | 5/1998 | Bisgard-Frantzen |
| 5,776,757 A | 7/1998 | Schulein |
| 5,814,501 A | 9/1998 | Becker |
| 5,989,169 A | 11/1999 | Svendsen |
| 6,022,724 A | 2/2000 | Svendsen |
| 6,093,562 A | 7/2000 | Bisgaard-Frantzen |
| 6,143,708 A | 11/2000 | Svendsen et al. |
| 6,187,576 B1 | 2/2001 | Svendsen |
| 6,297,038 B1 | 10/2001 | Bisgaard-Frantzen |
| 6,361,989 B1 | 3/2002 | Svendsen |
| 6,410,295 B1 | 6/2002 | Andersen |
| 6,440,716 B1 | 8/2002 | Svendsen |
| 6,475,762 B1 | 11/2002 | Stafford |
| 6,562,612 B2 | 5/2003 | Jones |
| 6,867,031 B2 | 3/2005 | Bisgaard-Frantzen |
| 7,115,409 B1 | 10/2006 | Svendsen |
| 7,163,816 B2 | 1/2007 | Svendsen |
| 7,378,264 B2 | 5/2008 | Svendsen |
| 7,432,099 B2 | 10/2008 | Andersen |
| 7,498,158 B2 | 3/2009 | Svendsen |
| 7,713,723 B1 | 5/2010 | Thisted |
| 7,993,897 B2 | 8/2011 | Svendsen |
| 2002/0155574 A1 | 10/2002 | Thisted |
| 2008/0220498 A1 | 9/2008 | Cervin |
| 2009/0082246 A1 | 3/2009 | Andersen |
| 2009/0117642 A1 | 5/2009 | Power |
| 2009/0143270 A1 | 6/2009 | Svendsen |
| 2009/0314286 A1 | 12/2009 | Cuevas |
| 2010/0144575 A1 | 6/2010 | Svendsen |
| 2011/0275136 A1 | 11/2011 | Andersen |
| 2012/0156733 A1 | 6/2012 | Cuevas |

FOREIGN PATENT DOCUMENTS

| EP | 0063909 A1 | 11/1982 |
| EP | 0119920 A2 | 9/1984 |
| EP | 0218272 A1 | 4/1987 |
| EP | 0252666 A2 | 1/1988 |
| EP | 0252730 A2 | 1/1988 |
| EP | 0258068 A2 | 3/1988 |

(Continued)

OTHER PUBLICATIONS

Jorgensen et al., PIR Accession No. A54541 (1995).

(Continued)

*Primary Examiner* — Delia Ramirez
(74) *Attorney, Agent, or Firm* — Michael W. Krenicky

(57) ABSTRACT

The present invention relates to variants (mutants) of parent Termamyl-like alpha-amylases, which variant has alpha-amylase activity and exhibits altered properties relative to the parent alpha-amylase.

25 Claims, 3 Drawing Sheets

FOREIGN PATENT DOCUMENTS

| | | |
|---|---|---|
| EP | 0260105 A2 | 3/1988 |
| EP | 00305216 A1 | 3/1989 |
| EP | 0407225 A1 | 1/1991 |
| EP | 1199356 A2 | 4/2002 |
| GB | 1296839 | 11/1972 |
| GB | 1372034 | 10/1974 |
| JP | 64-074992 | 3/1989 |
| WO | 89/06270 A1 | 7/1989 |
| WO | 89/06279 A1 | 7/1989 |
| WO | 89/09259 A1 | 10/1989 |
| WO | 90/11352 A1 | 10/1990 |
| WO | 90/12876 A1 | 11/1990 |
| WO | 91/00353 A2 | 1/1991 |
| WO | 91/16422 A1 | 10/1991 |
| WO | 91/17243 A1 | 11/1991 |
| WO | 92/06165 A1 | 4/1992 |
| WO | 92/06221 A1 | 4/1992 |
| WO | 92/17601 A1 | 10/1992 |
| WO | 92/05249 A1 | 11/1992 |
| WO | 92/19708 A1 | 11/1992 |
| WO | 92/19709 A1 | 11/1992 |
| WO | 92/19729 A1 | 11/1992 |
| WO | 93/09244 A1 | 5/1993 |
| WO | 93/24618 A1 | 12/1993 |
| WO | 94/01541 A1 | 1/1994 |
| WO | 94/02597 A1 | 2/1994 |
| WO | 94/18314 A1 | 8/1994 |
| WO | 94/25578 A1 | 11/1994 |
| WO | 94/25583 A1 | 11/1994 |
| WO | 95/06720 A1 | 3/1995 |
| WO | 95/10602 A1 | 4/1995 |
| WO | 95/10603 A1 | 4/1995 |
| WO | WO 95/10603 * | 4/1995 |
| WO | 95/14807 A1 | 6/1995 |
| WO | 95/21247 A1 | 8/1995 |
| WO | 95/22615 A1 | 8/1995 |
| WO | 95/22625 A1 | 8/1995 |
| WO | 95/26397 A1 | 10/1995 |
| WO | WO 95/26397 | 10/1995 |
| WO | 95/30283 A2 | 11/1995 |
| WO | 95/35381 A1 | 12/1995 |
| WO | 95/35382 A2 | 12/1995 |
| WO | 96/00292 A1 | 1/1996 |
| WO | 96/01323 A1 | 1/1996 |
| WO | 96/02633 A1 | 2/1996 |
| WO | 96/05295 A2 | 2/1996 |
| WO | 96/12012 A1 | 4/1996 |
| WO | 96/13580 A1 | 5/1996 |
| WO | 96/23873 A1 | 8/1996 |
| WO | WO 96/23874 | 8/1996 |
| WO | 96/27002 A1 | 9/1996 |
| WO | 96/28567 A1 | 9/1996 |
| WO | 96/30481 A1 | 10/1996 |
| WO | 96/38578 A1 | 12/1996 |
| WO | 96/39528 A2 | 12/1996 |
| WO | 97/00324 A1 | 1/1997 |
| WO | 97/04079 A1 | 2/1997 |
| WO | 97/07202 A1 | 2/1997 |
| WO | 97/43424 A1 | 11/1997 |
| WO | WO 97/41213 | 11/1997 |
| WO | 98/15257 A1 | 4/1998 |
| WO | 98/20115 A1 | 5/1998 |
| WO | 98/20116 A1 | 5/1998 |
| WO | 98/23732 A2 | 6/1998 |
| WO | 98/34946 A1 | 8/1998 |
| WO | WO 99/09183 | 2/1999 |
| WO | 99/19467 A1 | 4/1999 |
| WO | 99/20770 A2 | 4/1999 |
| WO | WO 99/19467 | 4/1999 |
| WO | 99/23211 A1 | 5/1999 |
| WO | 99/28448 A1 | 6/1999 |
| WO | 99/29876 A2 | 6/1999 |
| WO | 99/42567 A1 | 8/1999 |
| WO | 99/49740 A1 | 10/1999 |
| WO | 00/04136 A1 | 1/2000 |
| WO | WO 00/22103 * | 4/2000 |
| WO | WO 00/29560 | 5/2000 |
| WO | 00/60060 A2 | 10/2000 |
| WO | WO 00/60058 | 10/2000 |
| WO | WO 00/60059 | 10/2000 |
| WO | 01/04273 A2 | 1/2001 |
| WO | 01/14532 A2 | 3/2001 |
| WO | 01/64852 A1 | 9/2001 |
| WO | 01/66712 A2 | 9/2001 |
| WO | 02/10355 A2 | 2/2002 |
| WO | 02/14490 A2 | 2/2002 |
| WO | 02/31124 A2 | 4/2002 |
| WO | 2006/002643 A2 | 1/2006 |
| WO | 2006/043178 A2 | 4/2006 |
| WO | 2006/060062 A2 | 6/2006 |
| WO | 2008/002472 A2 | 1/2008 |
| WO | 2008/153925 A9 | 12/2008 |
| WO | 2009/061378 A2 | 5/2009 |
| WO | 2009/061379 A2 | 5/2009 |
| WO | 2009/061381 A2 | 5/2009 |

OTHER PUBLICATIONS

Takkinen et al., PIR Accession No. ALBSN (1980).
Witkowski et al., "Conversion of A B-Ketoacyl Synthase to a Malonyl", Biochemistry, vol. 38, pp. 11643-11650 (1999).
Seffernick, "Melamine Deaminase and Atrazine Chlorohydrolase: 98 Percent Identical But Functionally Different", Journal of Bacteriology, vol. 183, No. 8, pp. 2405-2410 (2001).
Branden et al., "Prediction, Engineering, and Design of Protein Structures", Introduction to Protein Structure, p. 247 (1991).
Guo et al., "Protein Tolerance to Random Amino Acid Change", PNAS, vol. 101, No. 25 pp. 9205-9210 (2004).
Declerk et al., "Probing Structural Determinants Specifying High", J. Mol. Biol., vol. 301, pp. 1041-1057 (2000).
EP Search Report in corresponding EP application No. 09175294.9 dated Jan. 27, 2010.
Altschul, et al., "Gapped BLAST and PSI-BLAST: a new generation of protein database search programs", Nucleic Acids Res., vol. 25, pp. 3389-3402 (1997).
Beaucage et al., "Deoxynucleoside phosphoramidites—A new class of key intermediates for deoxypolynucleotide synthesis", Tetrahedron Lett., vol. 22, No. 20, pp. 1859-1862 (1981).
Boel et al., "Glucoamylases G1 and G2 from *Aspergillus niger* are synthesized from two different but closely related mRNAs", The EMBO Journal, vol. 3, No. 5, pp. 1097-1102 (1984).
Cha et al., "Lowering the pH optimum of D-xylose isomerase: the effect of mutations of the negatively charged residues", Molecules and Cells, vol. 8, No. 4, pp. 374-382 (1998).
Cohen et al., "In vitro enzyme evolution: the screening challenge of isolating the one in a million", Trends in Biotechnology, vol. 19, No. 12, pp. 507-510 (2001).
Hahn et al., "Regulatory inputs for the synthesis of ComK, the competence transcription factor of *Bacillus subtilis*", Molecular Microbiology, vol. 21, No. 4, pp. 763-775 (1996).
Huber et al., "Protein fold recognition without Boltzmann statistics or explicit physical basis", Protein Science, vol. 7, No. 1, pp. 142-149 (1998).
Dartois et al., "Cloning, nucleotide sequence and expression in Escherichia coli of a lipase gene from *Bacillus subtilis*", Biochimica et Biophysica Acta, vol. 1131, No. 3, pp. 253-260 (1992).
Engelen et al., "Simple and rapid determination of phytase activity", Journal of AOAC International, vol. 77, No. 3, pp. 760-764 (1994).
Freire, "Differential Scanning Calorimetry", In Protein Stability and Folding: Theory and Practice, Methods in Molecular Biology, No. 40, ed. B.A. Shirley, New York: Humana Press pp. 191-218 (1995).
Gaboriaud et al., "Hydrophobic cluster analysis: an efficient new way to compare and analyse amino acid sequences", FEBS Letters, vol. 224, No. 1, pp. 149-155 (1987).
Holm et al., "Random mutagenesis used to probe the structure and function of *Bacillus stearothermophilus* alpha-amylase", Protein Engineering, vol. 3, No. 3, pp. 181-191 (1990).
Matthes et al., "Simultaneous rapid chemical synthesis of over one hundred oligonucleotides on a microscale", EMBO Journal, vol. 3, No. 4, pp. 801-805 (1984).
McKenzie et al., "The nucleotide sequence of pUB110: some salient features in relation to replication and its regulation", Plasmid, vol. 15, No. 2, pp. 93-103 (1986).

Needleman et al., "A general method applicable to the search for similarities in the amino acid sequence of two proteins", Journal Mol. Biol, vol. 48, No. 3, pp. 443-453 (1970).

Niedhardt et al., "Culture medium for Enterobacteria", J. Bacteriology, vol. 119, No. 3, pp. 736-747 (1974).

Pearson et al., "Improved tools for biological sequence comparison", Proc. Natl. Acad. Sci USA, vol. 85, No. 8, pp. 2444-2448 (1988).

Vogtentanz et al., "A *Bacillus subtilis* fusion protein system to produce soybean Bowman-Birk protease inhibitor", Protein Expression and Purification, vol. 55, No. 1, pp. 40-52 (2007).

Russell et al., "Electrostatic effects on modification of charged groups in the active site cleft of *subtilis* by protein engineering", Journal of Molecular Biology, vol. 193, No. 4, pp. 803-813 (1987).

Sambrook et al, Molecular Cloning: A Laboratory Manual, 2nd ed. New York; Cold Spring Harbor Press, (1989).

Smirnova et al., "Mutation in x-amylase gene of Bacillus amyloliquefaciens leading to reduction in temperature of protein inactivation", Molecular Biology Journal, vol. 22, No. 5, pp. 921-1036 (1988).

Tsukamoto et al., "Nucleotide sequence of the maltohexaose-producing amylase gene from an alkalophilic *Bacillus sp.* #707 and structural similarity to liquefying type alpha-amylases", Biochemical and Biophysical Research Communications, vol. 151, No. 1, pp. 25-31 (1988).

*Novozymes A/S* v *Genencor International Inc.* and *Enzyme Development Corporation*, 446 F.Supp.2d 297 (Aug. 24, 1996).

*Novozymes A/S* v *Genencor International Inc.* and *Enzyme Development Corporation*, 474 F.Supp.2d 592 (Feb. 16, 1997).

Gray, J Bacteriology 166(2), 635-643, 1986.

*Danisco* v. *Novozymes A/S* and *Novozymes North America, Inc.*, USDC, Northern District of California, Civil Action No. CV124502—Aug. 27, 2012.

*Danisco* v. *Novozymes A/S* and *Novozymes North America, Inc.*, USDC, Northern District of Iowa, Case No. 1:12-CV-00085-EJM—Aug. 27, 2012.

*Danisco* v. *Novozymes A/S* and *Novozymes North America, Inc.*, USDC, Northern District of California, Order Granting Motion to Dismiss No. CV124502 RS—Jan. 7, 2013.

\* cited by examiner

```
HHNGTNGTMM QYFEWHLPND GNHWNRLRDD ASNLRNRGIT AIWIPPAWKG
HHNGTNGTMM QYFEWYLPND GNHWNRLRDD AANLKSKGIT AVWIPPAWKG
....VNGTLM QYFEWYTPND GQHWKRLQND AEHLSDIGIT AVWIPPAYKG
..ANLNGTLM QYFEWYMPND GQHWRRLQND SAYLAEHGIT AVWIPPAYKG
.AAPFNGTMM QYFEWYLPDD GTLWTKVANE ANNLSSLGIT ALWLPPAYKG

TSQNDVGYGA YDLYDLGEFN QKGTVRTKYG TRSQLESAIH ALKNNGVQVY
TSQNDVGYGA YDLYDLGEFN QKGTVRTKYG TRNQLQAAVT SLKNNGIQVY
LSQSDNGYGP YDLYDLGEFQ QKGTVRTKYG TKSELQDAIG SLHSRNVQVY
TSQADVGYGA YDLYDLGEFH QKGTVRTKYG TKGELQSAIK SLHSRDINVY
TSRSDVGYGV YDLYDLGEFN QKGTVRTKYG TKAQYLQAIQ AAHAAGMQVY

GDVVMNHKGG ADATENVLAV EVNPNNRNQE ISGDYTIEAW TKFDFPGRGN
GDVVMNHKGG ADGTEIVNAV EVNRSNRNQE TSGEYAIEAW TKFDFPGRGN
GDVVLNHKAG ADATEDVTAV EVNPANRNQE TSEEYQIKAW TDFRFPGRGN
GDVVINHKGG ADATEDVTAV EVDPADRNRV ISGEHLIKAW THFHFPGRGS
ADVVFDHKGG ADGTEWVDAV EVNPSDRNQE ISGTYQIQAW TKFDFPGRGN

TYSDFKWRWY HFDGVDWDQS RQFQNRIYKF RGDGKAWDWE VDSENGNYDY
NHSSFKWRWY HFDGTDWDQS RQLQNKIYKF RGTGKAWDWE VDTENGNYDY
TYSDFKWHWY HFDGADWDES RKI.SRIFKF RGEGKAWDWE VSSENGNYDY
TYSDFKWHWY HFDGTDWDES RKL.NRIYKF ..QGKAWDWE VSNENGNYDY
TYSSFKWRWY HFDGVDWDES RKL.SRIYKF RGIGKAWDWE VDTENGNYDY
```

Fig. 1

```
LMYADVDMDH  PEVVNELRRW  GEWYTNTLNL  DGFRIDAVKH  IKYSFTRDWL
LMYADVDMDH  PEVIHELRNW  GVWYTNTLNL  DGFRIDAVKH  IKYSFTRDWL
LMYADVDYDH  PDVVAETKKW  GIWYANELSL  DGFRIDAAKH  IKFSFLRDWV
LMYADIDYDH  PDVAAEIKRW  GTWYANELQL  DGFRLDAVKH  IKFSFLRDWV
LMYADLDMDH  PEVVTELKNW  GKWYVNTTNI  DGFRLDAVKH  IKFSFFPDWL

THVRNATGKE  MFAVAEFWKN  DLGALENYLN  KTNWNHSVFD  VPLHYNLYNA
THVRNTTGKP  MFAVAEFWKN  DLGAIENYLN  KTSWNHSAFD  VPLHYNLYNA
QAVRQATGKE  MFTVAEYWQN  NAGKLENYLN  KTSFNQSVFD  VPLHFNLQAA
NHVREKTGKE  MFTVAEYWQN  DLGALENYLN  KTNFNHSVFD  VPLHYQFHAA
SYVRSQTGKP  LFTVGEYWSY  DINKLHNYIT  KTDGTMSLFD  APLHNKFYTA

SNSGGNYDMA  KLLNGTVVQK  HPMHAVTFVD  NHDSQPGESL  ESFVQEWFKP
SNSGGYYDMR  NILNGSVVQK  HPTHAVTFVD  NHDSQPGEAL  ESFVQQWFKP
SSQGGGYDMR  RLLDGTVVSR  HPEKAVTFVE  NHDTQPGQSL  ESTVQTWFKP
STQGGGYDMR  KLLNGTVVSK  HPLKSVTFVD  NHDTQPGQSL  ESTVQTWFKP
SKSGGAFDMR  TLMTNTLMKD  QPTLAVTFVD  NHDTEPGQAL  QSWVDPWFKP

LAYALILTRE  QGYPSVFYGD  YYGIPTHS..  .VPAMKAKID  PILEARQNFA
LAYALVLTRE  QGYPSVFYGD  YYGIPTHG..  .VPAMKSKID  PLLQARQTFA
LAYAFILTRE  SGYPQVFYGD  MYGTKGTSPK  EIPSLKDNIE  PILKARKEYA
LAYAFILTRE  SGYPQVFYGD  MYGTKGDSQR  EIPALKHKIE  PILKARKQYA
LAYAFILTRQ  EGYPCVFYGD  YYGIPQYN..  .IPSLKSKID  PLLIARRDYA

YGTQHDYFDH  HNIIGWTREG  NTTHPNSGLA  TIMSDGPGGE  KWMYVGQNKA
YGTQHDYFDH  HDIIGWTREG  NSSHPNSGLA  TIMSDGPGGN  KWMYVGKNKA
YGPQHDYIDH  PDVIGWTREG  DSSAAKSGLA  ALITDGPGGS  KRMYAGLKNA
YGAQHDYFDH  HDIVGWTREG  DSSVANSGLA  ALITDGPGGA  KRMYVGRQNA
YGTQHDYLDH  SDIIGWTREG  GTEKPGSGLA  ALITDGPGGS  KWMYVGKQHA
```

Fig. 1 (continued)

```
GQVWHDITGN KPGTVTINAD GWANFSVNGG SVSIWVKR..  ..........
GQVWRDITGN RTGTVTINAD GWGNFSVNGG SVSVWVKQ..  ..........
GETWYDITGN RSDTVKIGSD GWGEFHVNDG SVSIYVQ...  ..........
GETWHDITGN RSEPVVINSE GWGEFHVNGG SVSIYVQR..  ..........
GKVFYDLTGN RSDTVTINSD GWGEFKVNGG SVSVWVPRKT  TVSTIARPIT

..........  ........
..........  ........
..........  ........
..........  ........
TRPWTGEFVR  WTEPRLVAW
```

Fig. 1 (continued)

ALPHA-AMYLASE VARIANT WITH ALTERED PROPERTIES

CROSS-REFERENCE TO RELATED APPLICATIONS

This application is a continuation of U.S. application Ser. No. 10/477,725 filed Nov. 14, 2003 (now U.S. Pat. No. 7,498,158) which is a 35 U.S.C. 371 national application of PCT/DK02/00319 filed May 15, 2002, which claims priority or the benefit under 35 U.S.C. 119 of Danish application nos. PA 2001 00760, PA 2001 00981, PA 2001 00982, PA 2001 00998, PA 2001 00999 and PA 2001 01443 filed May 15, 2001, Jun. 22, 2001, Jun. 22, 2001, Jun. 26, 2001, Jun. 26, 2001, and Oct. 2, 2001, respectively and of U.S. provisional application Nos. 60/296,631, 60/302,391, 60/302,392, 60/302,395, 60/302,570, and 60/326,750, filed Jun. 7, 2001, Jun. 29, 2001, Jul. 2, 2001, Jul. 2, 2001, Jul. 2, 2001, and Oct. 3, 2001, respectively, the contents of which are fully incorporated herein by reference.

FIELD OF THE INVENTION

The present invention relates to a variant of parent Termamyl-like alpha-amylase, which variant has alpha-amylase activity and exhibits an alteration in at least one of the following properties relative to said parent alpha-amylase: Substrate specificity, substrate binding, substrate cleavage pattern, thermal stability, pH activity profile, pH stability profile, stability towards oxidation, $Ca^{2+}$ dependency, reduced and increased pI and improved wash performance, specific activity, stability under, e.g., high temperature and/or low pH conditions, in particular at low calcium concentrations. The variant of the invention are suitable for starch conversion, ethanol production, laundry wash, dish wash, hard surface cleaning, textile desizing, and/or sweetner production.

BACKGROUND OF THE INVENTION

Alpha-Amylases (alpha-1,4-glucan-4-glucanohydrolases, E.C. 3.2.1.1) constitute a group of enzymes, which catalyze hydrolysis of starch and other linear and branched 1,4-glucosidic oligo- and polysaccharides.

BRIEF DISCLOSURE OF THE INVENTION

The object of the present invention is to provide a Termamyl-like alpha-amylase, which variant in comparison to the corresponding parent alpha-amylase, i.e., un-mutated alpha-amylase, has alpha-amylase activity and exhibits an alteration in at least one of the above mentioned properties relative to said parent alpha-amylase.

Nomenclature

In the present description and claims, the conventional one-letter and three-letter codes for amino acid residues are used. For ease of reference, alpha-amylase variants of the invention are described by use of the following nomenclature:

Original Amino Acid(s): Position(s): Substituted Amino Acid(s)

According to this nomenclature, for instance the substitution of alanine for asparagine in position 30 is shown as:
 Ala30Asn or A30N
a deletion of alanine in the same position is shown as:
 Ala30* or A30*
and insertion of an additional amino acid residue, such as lysine, is shown as:
 Ala30AlaLys or A30AK
A deletion of a consecutive stretch of amino acid residues, such as amino acid residues 30-33, is indicated as (30-33)* or Δ(A30-N33).

Where a specific alpha-amylase contains a "deletion" in comparison with other alpha-amylases and an insertion is made in such a position this is indicated as:
 *36Asp or *36D
for insertion of an aspartic acid in position 36.
Multiple mutations are separated by plus signs, i.e.:
 Ala30Asp+Glu34Ser or A30N+E34S
representing mutations in positions 30 and 34 substituting alanine and glutamic acid for asparagine and serine, respectively.

When one or more alternative amino acid residues may be inserted in a given position it is indicated as
 A30N,E or
 A30N or A30E Furthermore, when a position suitable for modification is identified herein without any specific modification being suggested, it is to be understood that any amino acid residue may be substituted for the amino acid residue present in the position. Thus, for instance, when a modification of an alanine in position 30 is mentioned, but not specified, it is to be understood that the alanine may be deleted or substituted for any other amino acid, i.e., any one of:
R,N,D,A,C,Q,E,G,H,I,L,K,M,F,P,S,T,W,Y,V.

Further, "A30X" means any one of the following substitutions:
A30R, A30N, A30D, A30C, A30Q, A30E, A30G, A30H, A30I, A30L, A30K, A30M, A30F, A30P, A30S, A30T, A30W, A30Y, or A30V; or in short: A30R,N,D,C,Q,E,G,H,I,L,K,M,F,P,S,T,W,Y,V.

If the parent enzyme—used for the numbering—already has the amino acid residue in question suggested for substitution in that position the following nomenclature is used:
 "X30N" or "X30N,V" in the case where for instance one or N or V is present in the wildtype.

Thus, it means that other corresponding parent enzymes are substituted to an "Asn" or "Val" in position 30.

Characteristics of Amino Acid Residues
Charged Amino Acids:
Asp, Glu, Arg, Lys, His
Negatively Charged Amino Acids (with the Most Negative Residue First):
Asp, Glu
Positively Charged Amino Acids (with the Most Positive Residue First):
Arg, Lys, His
Neutral Amino Acids:
Gly, Ala, Val, Leu, Ile, Phe, Tyr, Trp, Met, Cys, Asn, Gln, Ser, Thr, Pro
Hydrophobic Amino Acid Residues (with the Most Hydrophobic Residue Listed Last):
Gly, Ala, Val, Pro, Met, Leu, Ile, Tyr, Phe, Trp,
Hydrophilic Amino Acids (with the Most Hydrophilic Residue Listed Last):
Thr, Ser, Cys, Gln, Asn

BRIEF DESCRIPTION OF THE DRAWINGS

FIG. 1 is an alignment of the amino acid sequences of five parent Termamyl-like alpha-amylases. The numbers on the extreme left designate the respective amino acid sequences as follows:
 1: SEQ ID NO: 4 (SP722)
 2: SEQ ID NO: 2 (SP690)
 3: SEQ ID NO: 10 (BAN)
 4: SEQ ID NO: 8 (BLA)
 5: SEQ ID NO: 6 (BSG).

DETAILED DISCLOSURE OF THE INVENTION

The object of the present invention is to provide a Termamyl-like amylase, which variant has alpha-amylase activity and exhibits an alteration in at least one of the following properties relative to the parent alpha-amylase: substrate specificity, substrate binding, substrate cleavage pattern, thermal stability, pH activity profile, pH stability profile, stability towards oxidation, $Ca^{2+}$ dependency, specific activity, stability under, e.g., high temperature and/or low pH conditions, in particular at low calcium concentrations.

Termamyl-Like Alpha-Amylases

A number of alpha-amylases produced by *Bacillus* spp. are highly homologous (identical) on the amino acid level.

The identity of a number of known *Bacillus* alpha-amylases can be found in the below Table 1:

TABLE 1

| | Percent identity | | | | | | | |
|---|---|---|---|---|---|---|---|---|
| | 707 | AP1378 | BAN | BSG | SP690 | SP722 | AA560 | Termamyl |
| 707 | 100.0 | 86.4 | 66.9 | 66.5 | 87.6 | 86.2 | 95.5 | 68.1 |
| AP1378 | 86.4 | 100.0 | 67.1 | 68.1 | 95.1 | 86.6 | 86.0 | 69.4 |
| BAN | 66.9 | 67.1 | 100.0 | 65.6 | 67.1 | 68.8 | 66.9 | 80.7 |
| BSG | 66.5 | 68.1 | 65.6 | 100.0 | 67.9 | 67.1 | 66.3 | 65.4 |
| SP690 | 87.6 | 95.1 | 67.1 | 67.9 | 100.0 | 87.2 | 87.0 | 69.2 |
| SP722 | 86.2 | 86.6 | 68.8 | 67.1 | 87.2 | 100.0 | 86.8 | 70.8 |
| AA560 | 95.5 | 86.0 | 66.9 | 66.3 | 87.0 | 86.8 | 100.0 | 68.3 |
| Termamyl | 68.1 | 69.4 | 80.7 | 65.4 | 69.2 | 70.8 | 68.3 | 100.0 |

For instance, the *B. licheniformis* alpha-amylase (BLA) comprising the amino acid sequence shown in SEQ ID NO: 8 (commercially available as Termamyl™) has been found to be about 81% homologous with the *B. amyloliquefaciens* alpha-amylase comprising the amino acid sequence shown in SEQ ID NO: 10 and about 65% homologous with the *B. stearothermophilus* alpha-amylase (BSG) comprising the amino acid sequence shown in SEQ ID NO: 6. Further homologous alpha-amylases include SP690 and SP722 disclosed in WO 95/26397 and further depicted in SEQ ID NO: 2 and SEQ ID NO: 4, respectively, herein. Other amylases are the AA560 alpha-amylase derived from *Bacillus* sp. and shown in SEQ ID NO: 12, and the #707 alpha-amylase derived from *Bacillus* sp., shown in SEQ ID NO: 13 and described by Tsukamoto et al., *Biochemical and Biophysical Research Communications*, 151 (1988), pp. 25-31.

The KSM AP1378 alpha-amylase is disclosed in WO 97/00324 (from KAO Corporation).

Still further homologous alpha-amylases include the alpha-amylase produced by the *B. licheniformis* strain described in EP 0252666 (ATCC 27811), and the alpha-amylases identified in WO 91/00353 and WO 94/18314. Other commercial Termamyl-like alpha-amylases are comprised in the products sold under the following tradenames: Optitherm™ and Takatherm™ (Solvay); Maxamyl™ (available from Gist-brocades/Genencor), Spezym AA™ and Spezyme Delta AA™ (available from Genencor), and Keistase™ (available from Daiwa), Dex lo, GC 521 (available from Genencor) and Ultraphlow (from Enzyme Biosystems).

Because of the substantial homology found between these alpha-amylases, they are considered to belong to the same class of alpha-amylases, namely the class of "Termamyl-like alpha-amylases".

Accordingly, in the present context, the term "Termamyl-like" alpha-amylase is intended to indicate an alpha-amylase, in particular *Bacillus* alpha-amylase, especially *Bacillus licheniformis* alpha-amylase, which, at the amino acid level, exhibits a substantial identity to Termamyl™, i.e., the *B. licheniformis* alpha-amylase having the amino acid sequence shown in SEQ ID NO: 8, herein.

In other words, all the following alpha-amylases, which has the amino acid sequences shown in SEQ ID NOS: 2, 4, 6, 8, 10, 12 and 13 herein are considered to be "Termamyl-like alpha-amylase". Other Termamyl-like alpha-amylases are alpha-amylases i) which displays at least 60%, such as at least 70%, e.g., at least 75%, or at least 80%, at least 85%, at least 90%, at least 95%, at least 96%, at least 97%, at least 98%, at least 99% homology (identity) with at least one of said amino acid sequences shown in SEQ ID NOS: 2, 4, 6, 8, 10, 12, and 13, and/or is encoded by a DNA sequence which hybridizes to the DNA sequences encoding the above-specified alpha-amylases which are apparent from SEQ ID NOS: 1, 3, 5, 7, 9, and of the present specification (which encoding sequences encode the amino acid sequences shown in SEQ ID NOS: 2, 4, 6, 8, 10 and 12 herein, respectively).

Homology (Identify)

The homology may be determined as the degree of identity between the two sequences indicating a derivation of the first sequence from the second. The homology may suitably be determined by means of computer programs known in the art such as GAP provided in the GCG program package (described above). Thus, Gap GCGv8 may be used with the default scoring matrix for identity and the following default parameters: GAP creation penalty of 5.0 and GAP extension penalty of 0.3, respectively for nucleic acidic sequence comparison, and GAP creation penalty of 3.0 and GAP extension penalty of 0.1, respectively, for protein sequence comparison. GAP uses the method of Needleman and Wunsch, (1970), J. Mol. Biol. 48, p. 443-453, to make alignments and to calculate the identity.

A structural alignment between Termamyl (SEQ ID NO: 8) and, e.g., another alpha-amylase may be used to identify equivalent/corresponding positions in other Termamyl-like alpha-amylases. One method of obtaining said structural alignment is to use the Pile Up programme from the GCG package using default values of gap penalties, i.e., a gap creation penalty of 3.0 and gap extension penalty of 0.1. Other structural alignment methods include the hydrophobic cluster analysis (Gaboriaud et al., (1987), FEBS LETTERS 224, pp. 149-155) and reverse threading (Huber, T; Torda, A E, PROTEIN SCIENCE Vol. 7, No. 1 pp. 142-149 (1998).

Hybridisation

The oligonucleotide probe used in the characterisation of the Termamyl-like alpha-amylase above may suitably be prepared on the basis of the full or partial nucleotide or amino acid sequence of the alpha-amylase in question.

Suitable conditions for testing hybridisation involve presoaking in 5×SSC and prehybridizing for 1 hour at 40° C. in a solution of 20% formamide, 5×Denhardt's solution, 50 mM sodium phosphate, pH 6.8, and 50 mg of denatured sonicated calf thymus DNA, followed by hybridisation in the same solution supplemented with 100 mM ATP for 18 hours at 40° C., followed by three times washing of the filter in 2×SSC, 0.2% SDS at 40° C. for 30 minutes (low stringency), preferred at 50° C. (medium stringency), more preferably at 65° C. (high stringency), even more preferably at 75° C. (very high stringency). More details about the hybridisation method can be found in Sambrook et al., Molecular Cloning: A Laboratory Manual, 2nd Ed., Cold Spring Harbor, 1989.

In the present context, "derived from" is intended not only to indicate an alpha-amylase produced or producible by a strain of the organism in question, but also an alpha-amylase encoded by a DNA sequence isolated from such strain and produced in a host organism trans-formed with said DNA sequence. Finally, the term is intended to indicate an alpha-amylase, which is encoded by a DNA sequence of synthetic and/or cDNA origin and which has the identifying characteristics of the alpha-amylase in question. The term is also intended to indicate that the parent alpha-amylase may be a variant of a naturally occurring alpha-amylase, i.e., a variant, which is the result of a modification (insertion, substitution, deletion) of one or more amino acid residues of the naturally occurring alpha-amylase.

Parent Termamyl-Like Alpha-Amylases

According to the invention any Termamyl-like alpha-amylase, as defined above, may be used as the parent (i.e., backbone) alpha-amylase. In a preferred embodiment of the invention the parent alpha-amylase is derived from *B. licheniformis*, e.g., one of those referred to above, such as the *B. licheniformis* alpha-amylase having the amino acid sequence shown in SEQ ID NO: 8.

Parent Hybrid Termamyl-Like Alpha-Amylases

The parent alpha-amylase (i.e., backbone alpha-amylase) may also be a hybrid alpha-amylase, i.e., an alpha-amylase, which comprises a combination of partial amino acid sequences derived from at least two alpha-amylases.

The parent hybrid alpha-amylase may be one, which on the basis of amino acid homology (identity) and/or DNA hybridization (as defined above) can be determined to belong to the Termamyl-like alpha-amylase family. In this case, the hybrid alpha-amylase is typically composed of at least one part of a Termamyl-like alpha-amylase and part(s) of one or more other alpha-amylases selected from Termamyl-like alpha-amylases or non-Termamyl-like alpha-amylases of microbial (bacterial or fungal) and/or mammalian origin.

Thus, the parent hybrid alpha-amylase may comprise a combination of partial amino acid sequences deriving from at least two Termamyl-like alpha-amylases, or from at least one Termamyl-like and at least one non-Termamyl-like bacterial alpha-amylase, or from at least one Termamyl-like and at least one fungal alpha-amylase. The Termamyl-like alpha-amylase from which a partial amino acid sequence derives, may be any of the specific Termamyl-like alpha-amylase referred to herein.

For instance, the parent alpha-amylase may comprise a C-terminal part of an alpha-amylase derived from a strain of *B. licheniformis*, and a N-terminal part of an alpha-amylase derived from a strain of *B. amyloliquefaciens* or from a strain of *B. stearothermophilus* (BSG). For instance, the parent alpha-amylase may comprise at least 430 amino acid residues of the C-terminal part of the *B. licheniformis* alpha-amylase, and may, e.g., comprise a) an amino acid segment corresponding to the 37 N-terminal amino acid residues of the *B. amyloliquefaciens* alpha-amylase having the amino acid sequence shown in SEQ ID NO: 10 and an amino acid segment corresponding to the 445 C-terminal amino acid residues of the *B. licheniformis* alpha-amylase having the amino acid sequence shown in SEQ ID NO: 8, or a hybrid Termamyl-like alpha-amylase being identical to the Termamyl sequence, i.e., the *Bacillus licheniformis* alpha-amylase shown in SEQ ID NO: 8, except that the N-terminal 35 amino acid residues (of the mature protein) has been replaced by the N-terminal 33 residues of BAN (mature protein), i.e., the *Bacillus amyloliquefaciens* alpha-amylase shown in SEQ ID NO: 10; or b) an amino acid segment corresponding to the 68 N-terminal amino acid residues of the *B. stearothermophilus* alpha-amylase having the amino acid sequence shown in SEQ ID NO: 6 and an amino acid segment corresponding to the 415 C-terminal amino acid residues of the *B. licheniformis* alpha-amylase having the amino acid sequence shown in SEQ ID NO: 8.

Another suitable parent hybrid alpha-amylase is the one previously described in WO 96/23874 (from Novo Nordisk) constituting the N-terminus of BAN, *Bacillus amyloliquefaciens* alpha-amylase (amino acids 1-300 of the mature protein) and the C-terminus from Termamyl (amino acids 301-483 of the mature protein).

In a preferred embodiment of the invention the parent Termamyl-like alpha-amylase is a hybrid alpha-amylase of SEQ ID NO: 8 and SEQ ID NO: 10. Specifically, the parent hybrid Termamyl-like alpha-amylase may be a hybrid alpha-amylase comprising the 445 C-terminal amino acid residues of the *B. licheniformis* alpha-amylase shown in SEQ ID NO: 8 and the 37 N-terminal amino acid residues of the alpha-amylase derived from *B. amyloliquefaciens* shown in SEQ ID NO: 10, which may suitably further have the following mutations: H156Y+A181T+N190F+A209V+Q264S (using the numbering in SEQ ID NO: 8). The latter mentioned hybrid is used in the examples below and is referred to as LE174.

Other specifically contemplated parent alpha-amylase include LE174 with fewer mutations, i.e., the right above mentioned hybrid having the following mutations: A181T+N190F+A209V+Q264S; N190F+A209V+Q264S; A209V+Q264S; Q264S; H156Y+N190F+A209V+Q264S; H156Y+A209V+Q264S; H156Y+Q264S; H156Y+A181T+A209V+Q264S; H156Y+A181T+Q264S; H156Y+Q264S; H156Y+A181T+N190F+Q264S; H156Y+A181T+N190F; H156Y+A181T+N190F+A209V. These hybrids are also considered to be part of the invention.

In a preferred embodiment the parent Termamyl-like alpha amylase is LE174, SP722, or AA560 including any of LE174+G48A+T49I+G107A+I201F; LE174+M197L; LE174+G48A+T49I+G107A+M197L+I201F, or SP722+D183*+G184*; SP722+D183*+G184*+N195F; SP722+D183*+G184*+M202L; SP722+D183*+G184*+N195F+M202L; BSG+I181*+G182*; BSG+I181*+G182*+N193F; BSG+I181*+G182*+M200L; BSG+I181*+G182*+N193F+M200L; AA560+D183*+G184*; AA560+D183*+G184*+N195F; AA560+D183*+G184*+M202L; AA560+D183*+G184*+N195F+M202L.

"BSG+I181*+G182*+N193F" means the *B. stearothermophilus* alpha-amylase has been mutated as follows: deletions in positions I181 and G182 and a substitution from Asn (N) to Phe (F) in position 193.

Other parent alpha-amylases contemplated include LE429, which is LE174 with an additional substitution in I201F. According to the invention LE335 is the alpha-amylase, which in comparison to LE429 has additional substitutions in T49I+G107A; LE399 is LE335+G48A, i.e., LE174, with G48A+T49I+G107A+I201F.

Altered Properties

The following section describes the relationship between mutations, which are present in a variant of the invention, and desirable alterations in properties (relative to those of a parent Termamyl-like alpha-amylase), which may result therefrom.

As mentioned above the invention relates to a Termamyl-like alpha-amylase with altered properties.

Parent Termamyl-like alpha-amylases specifically contemplated in connection with going through the specifically contemplated altered properties are the above mentioned parent Termamyl-like alpha-amylase and parent hybrid Termamyl-like alpha-amylases.

The *Bacillus licheniformis* alpha-amylase (SEQ ID NO: 8) is used as the starting point, but corresponding positions in, e.g., the SP722, BSG, BAN, AA560, SP690, KSM AP1378, #707 and other Termamyl-like alpha-amylases should be understood as disclosed and specifically contemplated too.

In an aspect the invention relates to variant with altered properties as mentioned above.

In the first aspect a variant of a parent Termamyl-like alpha-amylase, comprising an alteration at one or more positions (using SEQ ID NO: 8 for the amino acid numbering) selected from the group of:

5, 6, 36, 37, 38, 39, 42, 45, 47, 63, 66, 69, 70, 71, 72, 74, 75, 76, 79, 82, 83, 86, 87, 89, 93, 112, 113, 117, 120, 137, 213, 216, 220, 223, 225, 226, 227, 229, 243, 245, 279, 282, 311, 321, 324, 352, 353, 354, 357, 361, 362, 364, 368, 390, 395, 397, 399, 400, 401, 425, 451, 452, 453, 466, 468, 470, 471, 478, wherein (a) the alteration(s) are independently (i) an insertion of an amino acid downstream of the amino acid which occupies the position, (ii) a deletion of the amino acid which occupies the position, or (iii) a substitution of the amino acid which occupies the position with a different amino acid, (b) the variant has alpha-amylase activity and (c) each position corresponds to a position of the amino acid sequence of the parent Termamyl-like alpha-amylase having the amino acid sequence shown in SEQ ID NO: 8.

In the *Bacillus licheniformis* alpha-amylase shown in SEQ ID NO: 8 the positions to be mutates are one or more of:
G5, T6, G36, I37, T38, A39, I42, A45, K47, D63, E66, Q69, K70, G71, T72, R74, T75, K76, T79, E82, L83, A86, I87, S89, R93, T112, E113, A117, V120, A137, K213, G216, A220, L223, L225, D226, G227, R229, D243, V245, F279, S282, T311, V321, V324, L352, T353, R354, G357, V361, F362, G364, G368, A390, A395, G397, Q399, H400, D401, A425, D451, I452, T453, G466, G468, F470, H471, S478.

In the first aspect the invention also relates to a variant of a parent Termamyl-like alpha-amylase, comprising a substitution at one or more positions (using SEQ ID NO: 8 for the amino acid numbering) selected from the group of:

7, 8, 9, 11, 12, 19, 21, 22, 25, 32, 40, 41, 46, 48, 55, 57, 58, 60, 77, 95, 97, 98, 99, 100, 101, 102, 103, 105, 107, 115, 118, 135, 139, 141, 143, 151, 159, 160, 161, 162, 163, 166, 175, 177, 183, 186, 187, 192, 199, 200, 202, 203, 208, 212, 215, 219, 228, 230, 233, 236, 238, 240, 241, 244, 248, 256, 258, 259, 260, 262, 270, 273, 274, 277, 281, 283, 284, 285, 286, 287, 288, 289, 292, 295, 296, 304, 307, 312, 313, 320, 322, 323, 325, 326, 478, 327, 329, 331, 339, 343, 344, 346, 347, 349, 350, 359, 360, 369, 377, 380, 387, 409, 410, 411, 412, 423, 424, 426, 427, 428, 429, 430, 438, 440, 441, 449, 462, 472, 477, 479, 480, 481 wherein (a) the variant has alpha-amylase activity and (b) each position corresponds to a position of the amino acid sequence of the parent Termamyl-like alpha-amylase having the amino acid sequence shown in SEQ ID NO: 8.

In the *Bacillus licheniformis* alpha-amylase shown in SEQ ID NO: 8 the positions to be mutated are one or more of:
L7, M8, Q9, F11, E12, G19, H21, W22, L25, L32, V40, W41, Y46, G48, G55, G57, A58, D60, Y77, I95, V97, Y98, G99, D100, V101, V102, I103, H105, G107, V115, V118, I135, T139, F141, F143, S151, H159, F160, D161, G162, T163, D166, Y175, F177, D183, V186, S187, N192, A199, D200, D202, Y203, V208, I212, W215, Y219, F228, L230, V233, I236, F238, F240, L241, W244, V248, M256, T258, V259, A260, Y262, I270, Y273, L274, T277, H281, V283, F284, D285, V286, P287, L288, H289, F292, A295, S296, M304, L307, V312, V313, S320, T322, F323, D325, N326, H327, T329, P331, V339, F343, K344, L346, A347, A349, F350, P359, Q360, T369, I377, L380, I387, V409, G410, W411, T412, G423, S478, L424, A426, L427, I428, T429, D430, M438, V440, G441, W449, I462, V472, V477, I479, Y480, V481

Specific substitutions contemplated are:
X7A,R,N,D,C,Q,E,G,H,K,M,P,S,Y,V;
X8C,M;
X9A,R,N,D,C,Q,G,H,M,P,S,T,W,Y,V;
X11A,N,D,C,Q,G,H,I,L,M,P,S,T,W,Y,V;
X12A,R,N,D,C,E,G,H,I,L,K,M,F,P,S,T,W,Y,V;
X19A,R,N,D,C,Q,E,G,H,I,L,K,M,F,P,S,T,W,Y,V;
X21A,R,N,D,C,Q,E,G,H,I,L,K,M,F,P,S,T,W,Y,V;
X22A,R,N,D,C,Q,E,G,H,I,L,K,M,F,P,S,T,W,Y,V;
X25A,R,N,D,C,Q,E,G,H,I,L,K,M,F,P,S,T,W,Y,V;
X32A,R,N,D,C,Q,E,G,H,I,L,K,M,F,P,S,T,W,Y,V;
X40A,R,N,D,C,Q,E,G,H,I,L,K,M,F,P,S,T,W,Y,V;
X41A,R,N,D,C,Q,E,G,H,I,L,K,M,F,P,S,T,W,Y,V;
X46A,R,D,C,G,K,M,P,W,Y;
X48R,N,D,C,Q,E,G,H,K,M,F,P,W,Y;
X55A,R,N,D,C,Q,E,G,H,I,L,K,M,F,P,S,T,W,Y,V;
X57R,N,D,C,Q,E,G,H,K,M,P,W;
X58A,R,N,D,C,Q,E,G,H,K,M,S,T,W,Y,V;
X60A,R,D,C,Q,E,G,H,I,L,K,M,F,P,S,T,W,Y,V;
X77A,R,D,C,G,K,M,P,W,Y;
X95A,R,N,D,C,Q,E,G,H,I,L,K,M,F,P,S,T,W,Y,V;
X97A,R,N,D,C,Q,E,G,H,I,L,K,M,F,P,S,T,W,Y,V;
X98A,R,D,C,G,K,M,P,W,Y;
X99R,N,D,C,Q,E,G,H,I,L,K,M,F,P,S,T,W,Y,V;
X100A,R,D,C,Q,E,G,H,I,K,M,F,P,S,T,W,Y,V;
X101A,N,C,Q,G,I,L,M,P,S,T,W,Y,V;
X102N,D,C,Q,E,H,I,L,M,F,P,W,Y,V;
X103A,N,D,C,Q,E,G,M,P,S,W,Y;
X105A,N,C,Q,G,H,I,L,M,P,S,T,Y,V;
X107R,N,D,Q,E,H,K,M,F,P,W,Y;
X115R,N,D,C,Q,E,H,I,L,K,M,F,P,S,T,W,Y,V;
X118R,N,C,Q,E,H,I,L,K,M,F,P,S,T,W,Y,V;
X135A,R,N,D,C,Q,E,G,H,I,L,K,M,F,P,S,T,W,Y,V;
X139A,R,N,D,C,Q,E,G,H,I,L,K,M,F,P,S,T,W,Y,V;
X141A,R,N,D,C,Q,E,G,H,I,L,K,M,F,P,S,T,W,Y,V;
X143A,R,N,D,C,Q,E,G,H,I,L,K,M,F,P,S,T,Y,V;
X151A,R,N,D,C,Q,E,G,H,K,M,P,S,T,Y,V;
X159A,R,N,D,C,Q,E,G,H,I,L,K,M,F,P,S,T,W,V;
X160A,R,N,D,C,Q,E,G,H,I,L,K,M,F,P,S,T,W,Y,V;
X161A,R,D,C,Q,E,G,H,I,L,K,M,F,P,S,T,W,Y,V;
X162A,R,N,D,C,Q,E,G,H,I,L,K,M,F,P,S,T,W,Y,V;
X163A,R,N,D,C,Q,E,G,H,I,L,K,M,F,P,S,T,W,Y,V;
X166A,R,N,D,C,Q,G,H,I,L,K,M,F,P,S,T,WY,V;
X175A,R,D,C,G,K,M,P,W,Y;
X177A,N,D,C,Q,E,H,I,L,K,M,P,S,T,W,Y,V;
X183A,R,D,C,Q,E,G,H,I,L,K,M,F,P,S,T,W,Y,V;

X186A,R,N,D,C,Q,E,G,H,I,L,K,M,F,P,S,T,W,Y,V;
X187A,R,C,Q,E,G,H,I,L,K,M,F,P,W,Y,V;
X192A,R,N,D,C,Q,E,G,H,I,L,K,M,F,P,S,T,W,Y,V;
X199R,N,D,C,Q,E,G,H,I,L,K,M,F,P,S,T,W,Y,V;
X200A,R,D,C,Q,E,G,H,I,L,K,M,F,P,S,T,W,Y,V;
X202A,R,D,C,Q,E,G,H,I,L,K,M,F,P,S,T,W,Y,V;
X203A,R,D,C,G,K,M,P;
X208A,R,N,D,C,Q,E,G,H,I,L,K,M,F,P,S,T,W,Y,V;
X212A,N,C,Q,G,H,M,P,S,T,V;
X215A,R,N,D,C,Q,E,G,H,I,L,K,M,F,P,S,T,W,Y,V;
X219A,R,D,C,G,K,M,P,W,Y;
X228A,R,N,D,C,Q,E,G,H,I,L,K,M,P,S,T,W,Y,V;
X230A,R,N,D,C,Q,E,G,L,M,P,S,T,W,Y,V;
X233R,N,C,Q,E,G,H,I,K,M,P,S,T,W,Y;
X236A,C,Q,G,H,I,M,P,S,T,V;
X238A,R,N,D,C,Q,E,G,H,I,K,M,P,S,T,W,Y,V;
X240A,R,N,D,C,Q,E,G,H,I,L,K,M,F,P,S,T,W,Y,V;
X241A,N,C,Q,G,H,P,S,T,V;
X244A,R,N,D,C,Q,E,G,H,I,L,K,M,F,P,S,T,W,Y,V;
X248A,R,N,D,C,Q,E,G,H,I,L,K,M,F,P,S,T,W,Y,V;
X256C,M;
X258A,R,N,D,C,Q,E,G,H,I,L,K,M,F,P,S,T,W,Y,V;
X259A,R,N,D,C,Q,E,G,H,I,K,M,P,S,T,W,Y,V;
X260R,N,D,C,Q,E,H,I,L,K,M,F,P,T,W,Y,V;
X262A,R,D,C,G,K,M,P,W,Y;
X270A,N,C,Q,G,I,L,M,F,P,S,T,W,Y,V;
X273A,R,D,C,G,K,M,P,Y;
X274A,R,N,D,C,Q,E,G,H,I,L,K,M,F,P,S,T,WY,V;
X277A,R,N,D,C,Q,E,G,H,K,M,P,S,W,Y,V;
X281A,R,N,D,C,Q,E,G,K,M,P,S,T,W,Y,V;
X283A,R,N,C,Q,E,G,I,L,K,M,F,P,S,T,W,Y,V;
X284A,R,N,D,C,Q,E,G,I,L,K,M,F,P,S,T,Y,V;
X285A,R,D,C,Q,E,G,H,I,K,M,F,P,S,T,W,Y,V;
X286A,R,D,C,Q,E,G,H,I,K,M,F,P,S,T,W,Y,V; preferably
X286N,C,Q,I,L,M,P,T,V,Y,F;
X287R,N,D,C,Q,E,G,H,I,L,K,M,F,P,S,T,W,Y,V;
X288A,R,N,D,C,Q,E,G,H,I,L,K,M,F,P,S,T,W,Y,V;
X289A,R,N,D,C,Q,E,G,H,I,L,K,M,F,P,S,T,W,Y,V;
X292A,R,N,D,C,Q,E,G,H,I,L,K,M,F,P,S,T,W,Y,V;
X295A,R,N,D,C,Q,E,G,H,I,L,K,M,F,P,S,T,W,Y,V;
X296A,R,N,D,C,Q,E,G,H,I,L,K,M,F,P,S,T,W,Y,V;
X304C,M;
X307A,R,N,D,C,Q,E,G,H,I,L,K,M,F,P,S,T,W,Y,V;
X312A,N,C,Q,G,H,I,L,M,F,P,S,T,W,Y,V;
X313A,R,N,D,C,Q,E,G,H,I,L,K,M,F,P,S,T,W,Y,V;
X320R,N,D,C,Q,E,G,H,I,L,K,M,F,P,S,T,W,Y,V;
X322R,N,D,C,Q,E,G,H,L,K,M,F,P,S,T,W,Y,V;
X323A,R,N,D,C,Q,E,G,I,L,K,M,F,P,S,T,W,Y,V;
X325A,R,D,C,Q,E,G,H,I,L,K,M,F,P,S,T,W,Y,V;
X326A,R,N,C,Q,E,G,M,P,S,T,W;
X327A,R,C,G,H,I,L,K,M,P,S,T,W,Y,V;
X329A,R,N,D,C,Q,E,G,H,I,L,K,M,F,P,T,W,Y,V;
X331N,D,C,Q,E,G,H,I,L,M,F,P,S,T,W,Y,V;
X339A,R,N,C,Q,E,G,H,I,L,K,M,F,P,S,T,W,Y,V;
X343A,R,N,D,C,Q,E,G,H,I,L,K,M,F,P,S,T,Y,V;
X344A,R,N,D,C,Q,E,G,H,I,L,K,M,F,P,S,T,W,Y,V;
X346A,R,N,D,Q,E,G,H,I,L,K,M,F,P,S,T,W,Y,V;
X347A,R,N,D,C,Q,E,G,H,I,L,K,M,F,P,S,T,W,Y,V;
X349R,N,D,Q,E,G,H,I,L,K,M,F,P,S,T,W,Y,V;
X350A,R,N,C,Q,G,H,I,L,K,M,F,P,S,T,Y,V;
X359R,N,D,C,Q,E,G,H,I,L,K,M,F,P,S,T,W,Y,V;
X360N,D,Q,G,H,I,L,M,F,P,S,T,W,Y,V;
X369A,R,N,D,C,Q,E,G,H,I,L,K,M,F,P,S,T,W,Y,V;
X377A,R,N,D,C,Q,E,G,H,I,L,K,M,F,P,S,T,W,Y,V;
X380A,R,N,D,C,Q,E,G,H,K,P,S,W,Y,V;
X387A,R,N,D,C,Q,E,G,H,L,K,M,P,S,T,W,Y,V;
X409N,C,Q,E,G,H,M,P,S,T,W,Y,V;
X410A,R,N,D,C,Q,E,G,H,I,L,K,M,F,P,S,T,W,Y,V;
X411A,R,N,D,C,Q,E,G,H,I,L,K,M,F,P,S,T,W,Y,V;
X412R,N,C,Q,E,G,H,I,L,K,M,F,P,S,T,W,Y,V;
X423A,R,N,D,C,Q,E,G,H,I,L,K,M,F,P,S,T,W,Y,V;
X424A,R,N,D,C,Q,E,G,H,I,L,K,M,F,P,S,T,W,Y,V;
X426A,R,N,D,C,Q,E,G,H,I,L,K,M,F,P,S,T,W,Y,V;
X427A,R,N,D,C,Q,E,G,H,K,M,P,S,T,Y,V;
X428A,N,D,Q,E,G,H,I,M,F,P,S,W,Y,V;
X429A,R,N,D,C,Q,E,G,H,I,L,K,M,F,P,S,T,W,Y,V;
X430A,R,D,C,Q,E,G,H,I,L,K,M,F,P,S,T,W,Y,V;
X438C,M;
X440R,N,D,C,Q,E,G,H,I,L,K,M,F,P,S,T,W,Y,V;
X441A,R,N,D,C,Q,E,G,H,I,L,K,M,F,P,S,T,W,Y,V;
X449A,R,N,D,C,Q,E,G,H,I,L,K,M,F,P,S,T,W,Y,V;
X462A,R,N,D,C,Q,E,G,H,I,L,K,M,F,P,S,T,W,Y,V;
X472A,R,N,D,C,Q,E,G,H,I,L,K,M,F,P,S,T,W,Y,V;
X477A,R,N,D,C,Q,E,G,H,I,L,K,M,F,P,S,T,W,Y,V;
X479A,R,N,D,Q,E,G,H,I,L,K,M,F,P,S,W,Y,V;
X480A,R,D,C,G,K,M,P,W,Y;
X481A,R,N,D,C,Q,E,G,H,K,M,P,S,T,Y,V where each position corresponds to a position of the amino acid sequence of the parent Termamyl-like alpha-amylase having the amino acid sequence shown in SEQ ID NO: 8 (*Bacillus licheniformis* alpha-amylase).

Also according to the first aspect, the invention relates to a variant of a parent Termamyl-like alpha-amylase, comprising a substitution at one or more positions (using SEQ ID NO: 8 for the amino acid numbering) selected from the group of: 1, 2, 3, 4, 13, 14, 16, 17, 18, 20, 23, 24, 26, 34, 35, 49, 50, 51, 52, 53, 61, 62, 67, 68, 73, 84, 85, 88, 91, 92, 96, 106, 108, 114, 116, 119, 121, 122, 123, 124, 125, 126, 127, 128, 129, 130, 131, 132, 133, 134, 136, 138, 145, 147, 148, 149, 150, 152, 153, 154, 155, 156, 157, 158, 164, 165, 167, 168, 169, 170, 171, 172, 173, 176, 179, 180, 181, 182, 184, 185, 188, 189, 190, 191, 193, 196, 198, 204, 205, 206, 209, 210, 211, 214, 217, 218, 221, 222, 234, 235, 237, 239, 242, 246, 247, 249, 250, 251, 252, 253, 254, 255, 257, 261, 263, 265, 266, 267, 268, 269, 271, 272, 275, 276, 278, 280, 290, 291, 293, 294, 297, 298, 299, 300, 301, 302, 303, 305, 306, 308, 309, 310, 314, 315, 316, 317, 318, 319, 328, 332, 333, 334, 335, 336, 337, 338, 340, 341, 342, 345, 355, 358, 363, 370, 371, 373, 374, 375, 376, 378, 379, 381, 389, 393, 394, 396, 398, 402, 403, 404, 405, 406, 407, 408, 413, 414, 415, 416, 417, 418, 419, 420, 421, 422, 431, 432, 433, 434, 435, 436, 437, 439, 442, 443, 444, 445, 446, 447, 448, 450, 454, 455, 456, 457, 458, 459, 460, 461, 463, 464, 465, 467, 469, 473, 474, 475, 476, 482, 483 wherein
(a) the variant has alpha-amylase activity and (b) each position corresponds to a position of the amino acid sequence of the parent Termamyl-like alpha-amylase having the amino acid sequence shown in SEQ ID NO: 8.

In the *Bacillus licheniformis* alpha-amylase shown in SEQ ID NO: 8 the positions to be mutated are one or more of:
A1, N2, L3, N4, W13, Y14, P16, N17, D18, Q20, R23, R24, Q26, E34, H35, T49, S50, Q51, A52, D53, L61, Y62, F67, H68, V73, Q84, S85, K88, H91, S92, N96, K106, G108, D114, T116, E119, D121, P122, A123, D124, R125, N126, R127, V128, I129, S130, G131, E132, H133, L134, K136, W138, G145, G147, S148, T149, Y150, D152, F153, K154, W155, H156, W157, Y158, D164, W165, E167, S168, R169, K170, L171, N172, R173, K176, G179, K180, A181, W182, W184, E185, N188, E189, N190, G191, Y193, L196, Y198, D204, H205, P206, A209, A210, E211, R214, T217, W218, N221, E222, K234, H235, K237, S239, R242, N246, H247, R249, E250, K251, T252, G253, K254, E255, F257, E261, W263, N265, D266, L267, G268, A269, E271, N272, N275, K276, N278, N280, Y290, Q291, H293, A294, T297, Q298, G299, G300, G301, Y302, D303, R305, K306, L308, N309, G310, S314, K315, H316, P317, L318, K319, D328, G332, Q333, S334, L335, E336, S337, T338, Q340, T341, W342, P345, E355, Y358, Y363, K370, G371, S373, Q374, R375, E376, P378, A379, K381, K389, Q393, Y394, Y396, A398, Y402, F403, D404, H405, H406, D407, I408, R413, E414, G415, D416, S417, S418, V419, A420, N421, S422, G431, P432, G433, G434, A435, K436, R437, Y439, R442, Q443, N444, A445, G446, E447, T448, H450, G454, N455, R456, S457, E458, P459, V460, V461, N463, S464, E465, W467, E469, N473, G474, G475, S476, Q482, R483.

Specific substitutions contemplated are:
X1A,R,N,D,C,Q,E,G,H,I,L,K,M,F,P,S,T,W,Y;
X2R,N,D,C,Q,E,G,H,I,L,K,M,F,S,T,W,Y,V;
X3A,R,N,D,C,Q,E,G,H,I,L,K,M,F,P,S,T,W,Y;
X4A,R,N,D,C,Q,E,G,H,I,L,K,M,F,P,S,T,W,Y,V;
X13R,N,D,C,Q,E,G,H,K,M,P,S,T,W;
X14A,R,D,C,G,K,M,P,W;
X16R,N,D,C,Q,E,G,H,I,L,K,M,F,S,T,W,Y,V;
X17A,R,N,D,C,Q,E,G,H,I,L,K,M,F,P,S,T,W,Y,V;
X18A,R,N,D,C,Q,E,G,H,I,L,K,M,F,P,S,T,W,Y,V;
X20A,R,N,D,C,Q,E,G,H,I,L,K,M,F,P,S,T,W,Y,V;
X23A,R,N,D,C,Q,E,G,H,I,L,M,F,P,S,W,Y,V;
X24A,R,N,D,C,Q,E,G,H,I,L,K,M,F,P,S,T,W,Y,V;
X26A,D,C,E,G,H,I,L,M,F,P,S,T,W,V;
X34A,R,N,C,Q,E,G,H,I,L,K,M,F,P,T,W,Y,V;
X35A,R,N,D,C,Q,E,G,H,K,M,F,P,S,T,W,Y,V;
X49A,C,G,H,P,T;
X50A,R,N,C,Q,E,G,H,K,M,F,P,S,W;
X51A,N,D,C,Q,E,G,H,I,L,M,F,P,S,T,W,Y,V;
X52A,R,D,C,Q,E,G,H,K,P;
X53A,D,C,G,H,K,M,P;
X61A,R,N,D,C,Q,E,G,H,I,L,K,M,P,S,T,Y;
X62A,R,D,C,G,K,M,P,Y;
X67A,R,N,D,C,Q,E,G,H,I,L,K,M,F,P,S,T,Y,V;
X68A,R,D,C,E,G,H,I,L,K,M,F,P,S,T,W,Y,V;
X73A,R,N,D,C,Q,E,G,H,K,M,P,S,T,W,Y,V;
X84A,R,N,D,C,G,H,I,L,K,M,F,P,S,T,W,Y,V;
X85A,R,N,C,E,G,H,I,L,K,M,F,P,S,T,W,Y,V;
X88A,R,N,D,C,E,G,H,I,L,K,M,F,P,S,T,W,Y,V;
X91A,R,N,D,C,Q,E,G,H,I,L,K,M,F,P,S,T,W,Y,V;
X92A,R,N,D,C,Q,E,G,H,I,L,M,F,P,S,T,W,Y,V;
X96A,R,N,D,C,E,G,H,I,L,K,M,F,P,S,T,W,Y,V;
X106A,N,D,C,Q,E,G,H,I,L,K,M,P,S,T,Y,V;
X108R,N,D,C,Q,E,G,H,I,L,K,M,F,P,S,T,W,Y,V;
X114A,N,C,Q,E,G,H,K,F,P,S,T,W,Y;
X116A,R,D,C,Q,E,G,H,I,L,M,F,P,S,W,Y,V;
X119A,R,N,D,Q,E,G,H,I,L,K,M,F,P,S,T,W,Y,V;
X121A,R,D,C,Q,E,G,H,I,L,K,M,F,P,S,T,W,Y,V;
X122R,N,Q,G,H,I,L,M,F,S,T,W,Y,V;
X123N,D,C,Q,E,G,H,I,L,M,F,P,S,T,W,Y,V;
X124N,Q,G,H,I,L,M,F,P,S,T,W,Y,V;
X125R,N,Q,E,G,I,K,M,F,S,T,W,Y;
X126N,Q,G,H,I,L,M,F,P,S,T,W,Y,V;
X127A,R,N,D,E,G,H,I,L,K,M,F,P,S,T,W,Y,V;
X128A,R,N,D,C,Q,G,H,I,L,K,M,F,P,S,W,Y,V;
X129A,R,N,D,C,Q,E,G,H,I,L,K,M,F,P,S,W,Y,V;
X130A,R,N,D,Q,E,G,H,I,L,K,M,F,P,S,W,Y,V;
X131A,R,N,D,C,Q,G,H,I,L,K,M,F,P,S,T,W,Y,V;
X132R,N,D,C,Q,E,G,H,I,L,K,M,F,S,W,Y;
X133R,N,D,C,M,T,W,V;
X134A,N,D,C,E,G,H,I,L,K,M,F,P,S,T,W,Y,V;
X136A,R,N,D,C,E,G,H,I,L,K,M,F,P,S,T,W,Y,V;
X138R,N,D,Q,E,G,I,K,M,P,S,T,W,V;
X145A,R,N,D,C,Q,E,G,H,I,L,K,M,P,S,T,Y,V;
X147A,R,N,D,C,Q,E,G,H,I,L,K,M,P,S,T,W,Y,V;
X148A,R,D,C,Q,E,G,H,I,L,K,M,F,P,T,W,Y,V;
X149A,R,N,D,C,Q,E,G,H,L,K,M,F,P,S,T,W,Y,V;
X150A,D,C,G,M,P,W,Y;
X152A,R,N,C,Q,E,G,H,I,L,K,M,F,P,T,W,Y,V;
X153A,R,N,D,C,Q,E,G,H,I,L,K,M,F,P,S,T,W,Y,V;
X154A,R,N,D,C,Q,E,G,H,I,L,K,M,F,P,S,T,W,Y,V;
X155A,R,N,D,C,Q,E,G,H,I,L,K,M,F,P,S,T,W,Y,V;
X156A,C,Q,E,G,I,L,M,F,P,S,T,W,V;
X157R,I,L,M,F,P,S,T,W,Y,V;
X158R,M,P,W,Y;
X164R,I,L,M,F,P,S,T,W,Y,V;
X165A,N,D,C,Q,E,H,I,L,K,M,F,P,S,T,W,Y,V;
X167A,R,N,D,C,Q,G,H,I,L,K,M,F,P,S,T,W,Y,V;
X168A,R,N,D,C,Q,E,G,H,I,L,K,M,F,S,T,W,V;
X169A,R,N,D,C,Q,E,G,H,M,P,S,W,Y,V;
X170A,R,N,D,C,E,G,H,I,L,K,M,F,P,S,T,W,Y,V;
X171A,R,N,D,C,Q,E,G,H,K,M,P,S,T,W,Y,V;
X172A,N,D,C,Q,E,G,I,L,M,F,P,T,W,Y,V;
X173A,N,D,C,Q,E,G,H,M,P,S,W,Y,V;
X176A,N,D,C,Q,E,G,H,I,L,K,M,F,P,S,T,W,Y,V;
X179D,C,Q,E,H,I,L,K,M,F,P,W,Y,V;
X180A,G,I,L,M,F,P,W,Y,V;
X181G;
X182A,R,N,D,C,Q,E,G,H,I,L,K,M,F,P,S,T,W,Y,V;
X184I,L,M,F,P,W,Y,V;
X185R,I,L,M,F,P,S,T,W,Y,V;
X188A,R,N,Q,G,H,L,M,F,W,V;
X189A,R,N,G,H,I,L,M,F,P,S,T,W,Y,V;
X190N;
X191A,R,N,Q,G,H,I,L,M,F,P,S,T,W,Y,V;
X193A,R,G,M,P,W,Y;
X196A,N,Q,G,H,I,L,M,P,S,T,W,V;
X198A,R,G,M,P,W;
X204R,L,M,F,P,T,W,Y,V;
X205A,G,H,I,L,M,F,P,W,Y,V;
X206R,N,D,C,Q,E,G,H,I,L,K,M,F,P,S,T,W,Y,V;
X209R,P,S,W,Y;
X210A,R,N,D,C,Q,E,G,H,I,L,K,M,F,P,W,Y,V;
X211E;
X214A,D,C,Q,E,G,I,L,M,F,P,S,T,Y,V;
X217A,R,N,D,C,Q,G,H,I,L,M,F,P,S,T,W,Y;
X218A,R,N,D,C,Q,E,G,H,I,L,K,M,F,P,S,T,W,Y,V;
X221A,R,D,C,Q,E,G,H,I,L,K,M,F,P,S,T,W,Y,V;
X222A,R,N,D,C,E,G,H,I,L,K,M,F,P,S,W,Y,V;
X234A,D,C,G,H,I,K,M,F,P,S,T,W,Y,V;
X235A,R,N,D,C,Q,E,G,H,I,L,K,M,F,P,S,T,W,Y,V;
X237A,G,H,I,L,M,F,W,Y,V;
X239G,H,I,L,M,F,P,S,T,Y,V;
X242G,I,L,M,F,S,T,W,Y,V;
X246A,R,N,D,C,Q,E,G,H,I,L,K,M,F,P,S,T,W,Y,V;
X247R,N,D,C,Q,E,G,H,I,L,K,M,F,P,S,T,W,V;
X249A,R,N,D,C,Q,E,G,H,I,L,K,M,F,P,S,T,W,Y,V;
X250A,R,N,D,C,E,H,I,L,K,M,P,T,W,Y,V;
X251R,N,D,C,E,G,H,I,L,K,M,F,P,S,T,W,Y,V;
X252A,R,N,D,C,Q,E,G,H,I,L,K,M,F,P,S,W,Y,V;
X253R,D,C,Q,E,H,I,L,K,M,F,P,S,T,W,Y;
X254A,R,N,D,C,Q,E,G,H,I,L,M,F,P,S,T,W,Y,V;
X255A,R,D,C,G,H,I,L,K,M,F,S,T,W,Y,V;
X257A,R,N,D,C,Q,E,G,H,I,L,K,M,F,P,S,T,W,Y,V;
X261A,R,N,D,C,Q,E,G,H,I,L,K,M,F,P,S,T,W,Y,V;
X263A,R,N,D,C,Q,E,G,I,L,K,M,F,P,S,T,W,Y,V;
X265C,Q,E,H,I,L,M,F,P,W;
X266A,R,N,D,C,Q,E,G,H,I,L,K,M,F,P,S,T,W,Y,V;
X267A,R,N,D,C,Q,E,G,H,K,P,S,T,W,Y,V;
X268A,R,N,D,C,Q,E,G,H,I,L,K,M,F,P,S,T,W,Y,V;
X269A,N,C,Q,G,H,I,L,M,F,P,S,T,W,Y,V;
X271A,R,N,D,C,Q,E,G,H,I,L,K,M,F,P,S,T,W,Y,V;

X272A,R,N,D,C,Q,E,G,H,I,L,K,M,F,P,S,T,W,Y,V;
X275A,R,D,C,Q,E,G,H,I,L,K,M,F,P,S,W,Y,V;
X276A,R,N,D,C,Q,E,G,H,I,L,M,F,P,S,T,W,Y,V;
X278A,R,N,D,C,Q,E,G,H,I,L,K,M,F,P,S,T,W,Y,V;
X280A,R,D,C,E,G,H,I,L,K,M,F,P,W,Y,V;
X290W,Y;
X291A,R,N,Q,G,H,I,L,M,F,P,S,T,W,Y,V;
X293A,R,N,G,I,L,M,P,S,T,W,V;
X294R,N,Q,G,H,I,L,M,F,P,S,T,W,Y;
X297A,G,H,I,L,M,F,P,W,Y,V;
X298G,H,I,L,M,F,P,S,T,W,Y,V;
X299A,G,H,M,P,S,T;
X300A,C,G,H,I,L,M,F,P,T,W,Y,V;
X301N,Q,H,I,L,M,F,P,S,T,W,Y,V;
X302R,M,P,W,Y;
X303R,I,L,M,F,P,S,T,W,Y,V;
X305G,I,L,M,F,P,S,T,W,Y,V;
X306Q,G,H,I,L,M,F,P,S,T,W,Y,V;
X308A,R,N,D,C,Q,E,G,H,I,L,K,M,F,P,S,T,W,Y,V;
X309N,Q,G,H,I,L,M,F,P,S,T,W,Y,V;
X310A,R,N,C,Q,E,H,I,L,K,M,F,P,S,T,W,Y,V;
X314A,D,C,E,G,I,L,M,F,P,W,Y,V;
X315A,N,C,Q,E,G,H,I,L,M,F,P,S,T,W,Y,V;
X316A,R,N,D,C,Q,E,G,H,I,L,K,M,F,P,S,T,W,V;
X317R,N,D,C,Q,E,G,H,I,L,K,M,F,P,S,T,W,Y,V;
X318A,R,N,D,C,Q,E,G,H,I,K,P,S,W,Y,V;
X319A,R,N,D,C,Q,E,G,H,I,L,M,F,P,S,T,W,Y,V;
X328A,R,N,D,C,Q,E,G,H,I,L,K,M,F,P,S,T,W,Y,V;
X332A,R,N,C,Q,E,G,H,I,L,K,M,F,P,S,T,W,Y,V;
X333A,N,D,C,G,I,M,F,P,S,T,Y,V;
X334R,N,C,Q,E,G,H,K,M,F,P,S,W,Y;
X335R,D,C,Q,E,H,I,L,K,M,F,P,W,Y,V;
X336A,N,D,C,Q,E,G,H,I,L,M,F,P,S,T,W,Y,V;
X337A,R,N,C,Q,E,G,H,I,L,M,F,P,S,T,W,Y,V;
X338A,R,N,C,Q,G,H,I,L,K,M,F,P,S,T,W,Y,V;
X340I,L,M,F,P,S,T,W,Y,V;
X341A,R,D,C,G,H,I,L,K,M,F,W,Y,V;
X342R,I,L,M,F,P,S,T,W,Y,V;
X345R,N,D,C,Q,E,G,H,I,L,K,M,F,P,T,W,Y,V;
X355A,R,N,D,C,Q,G,H,I,L,K,M,F,P,S,T,W,Y,V;
X358A,R,D,C,G,K,M,P,W,Y;
X363A,R,D,C,G,K,M,P,W,Y;
X370A,R,N,D,C,Q,E,G,H,I,L,K,M,F,P,S,T,W,Y,V;
X371A,N,C,Q,E,G,H,I,L,K,M,F,P,S,T,W,Y,V;
X373A,R,N,D,C,Q,E,G,H,I,L,K,M,F,S,T,W,Y,V;
X374A,N,D,C,Q,E,G,H,I,L,K,M,F,S,T,W,Y,V;
X375A,R,N,D,C,Q,G,H,I,L,K,M,F,P,S,T,W,Y,V;
X376A,R,N,D,C,Q,E,G,H,I,L,K,M,F,P,S,T,W,Y,V;
X378R,N,D,C,Q,E,G,H,I,L,K,M,F,S,T,W,Y,V;
X379A,R,N,D,C,Q,E,G,H,I,L,K,M,F,P,T,W,Y,V;
X381A,R,N,D,C,Q,E,G,H,I,L,K,M,F,P,S,T,W,Y,V;
X389A,D,C,G,H,M,F,P,S,T,W,Y,V;
X393A,N,C,Q,E,G,H,I,L,K,M,F,P,S,T,W,Y,V;
X394A,R,D,C,G,K,M,P,W,Y;
X396A,R,D,C,G,K,M,P,W,Y;
X398A,R,N,D,C,Q,E,G,H,I,L,M,F,W,Y,V;
X402R,C,G,K,M,P,W,Y;
X403A,R,N,Q,G,H,I,L,M,F,P,S,T,W,Y,V;
X404R,I,L,M,F,P,S,T,W,Y,V;
X405R,G,H,I,L,M,F,P,W,Y,V;
X406A,R,G,H,I,M,F,P,Y,V;
X407A,R,Q,G,H,I,L,M,F,P,S,T,W,Y,V;
X408A,R,N,D,C,Q,E,G,H,I,K,M,P,S,T,W,Y,V;
X413A,R,N,D,C,Q,E,G,H,I,L,K,M,F,P,S,T,W,Y,V;
X414A,R,N,D,C,Q,E,G,H,I,L,K,M,F,P,S,T,W,Y,V;
X415A,R,N,D,C,Q,E,G,H,I,L,K,M,F,P,S,T,W,Y,V;
X416A,R,N,D,C,Q,E,G,H,I,L,K,M,F,P,S,T,W,Y,V;
X417A,R,N,D,C,Q,E,G,H,I,L,K,M,F,P,S,W,Y,V;
X418A,R,N,D,C,Q,E,G,H,I,L,K,M,F,P,S,T,W,Y,V;
X419A,R,N,D,C,Q,E,G,H,I,L,M,F,P,S,T,W,Y,V;
X420A,N,D,C,E,G,H,I,L,K,M,F,S,T,W,Y,V;
X421A,R,N,D,C,Q,E,H,I,L,K,M,F,P,S,T,W,Y,V;
X422A,R,N,D,C,Q,E,G,H,I,L,K,M,F,P,S,T,W,Y,V;
X431A,R,N,Q,G,H,I,L,M,F,P,S,T,W,Y,V;
X432G,H,I,L,M,F,P,S,T,W,Y,V;
X433A,R,N,Q,G,H,I,L,M,F,P,S,T,W,Y,V;
X434A,R,N,Q,G,H,I,L,M,F,P,S,T,W,Y,V;
X435Q,G,H,I,L,M,F,P,T,W,Y,V;
X436A,R,N,D,C,Q,E,G,H,I,L,K,M,F,P,S,T,W,Y,V;
X437A,N,D,C,Q,E,G,H,I,L,K,M,F,P,S,T,W,Y,V;
X439A,R,D,C,G,K,M,P,W,Y;
X442A,R,N,D,C,E,G,H,I,L,M,F,P,S,T,W,Y,V;
X443A,R,N,D,C,E,G,H,I,L,M,F,P,S,T,W,Y,V;
X444A,C,G,H,I,L,M,F,P,S,T,W,Y,V;
X445A,R,N,D,C,Q,E,G,H,I,L,K,M,F,P,S,T,W,Y,V;
X446A,R,N,D,C,Q,E,G,H,I,L,K,M,F,P,S,T,W,Y,V;
X447A,N,D,C,G,H,I,L,M,F,P,S,T,W,Y,V;
X448A,R,N,D,C,Q,E,G,H,I,L,K,M,F,P,S,T,W,Y,V;
X450A,N,D,C,Q,E,G,I,L,K,M,F,P,S,T,W,V;
X454A,R,N,D,C,Q,E,G,H,I,L,K,M,F,P,S,T,W,Y,V;
X455A,R,N,C,Q,G,H,I,L,K,M,F,P,S,T,W,Y,V;
X456A,D,C,E,G,H,I,L,M,F,P,S,T,W,Y,V;
X457A,R,N,D,C,Q,E,G,H,I,L,K,M,F,W,Y,V;
X458A,R,N,C,Q,E,G,H,I,L,K,M,F,P,S,T,W,Y,V;
X459R,N,D,C,Q,E,G,H,I,L,K,M,F,S,W,Y,V;
X460A,R,N,D,C,Q,E,G,H,I,L,K,M,F,P,S,T,W,Y,V;
X461A,R,N,D,C,Q,E,G,H,I,L,M,F,P,S,W,Y,V;
X463A,R,N,D,C,Q,E,H,I,L,K,M,F,P,S,T,W,Y,V;
X464A,R,N,D,C,Q,E,G,H,I,L,K,M,F,P,S,T,W,Y,V;
X465A,R,N,C,Q,E,G,H,I,L,K,M,F,P,S,T,W,Y,V;
X467A,R,N,D,C,Q,E,G,H,I,L,K,M,F,P,S,T,W,Y,V;
X469A,R,N,D,C,Q,G,H,I,L,K,M,F,P,S,T,W,Y,V;
X473N,Q,G,H,I,L,M,F,P,S,T,W,Y,V;
X474A,R,G,H,I,L,M,F,P,W,Y,V;
X475A,N,Q,G,H,I,L,M,F,P,S,T,W,Y,V;
X476G,H,I,L,M,F,P,S,T,W,Y,V;
X482A,N,D,C,G,H,I,L,M,F,S,T,W,Y,V;
X483A,N,D,C,Q,E,G,H,I,L,M,F,P,S,T,W,Y,V where each position corresponds to a position of the amino acid sequence of the parent Termamyl-like alpha-amylase having the amino acid sequence shown in SEQ ID NO: 8 (*Bacillus licheniformis* alpha-amylase).

Specifically contemplated according to the invention is substitution at position 183 and/or 184 (using SEQ ID NO: 2 (SP690) for the amino acid numbering) with any amino acid, i.e. any one of A, R, N, D, C, Q, E, G, H, I, L, K, M, F, P, S, T, W, Y or V.

Also in the first aspect the invention relates to a variant of a parent Termamyl-like alpha-amylase, comprising an alteration at one or more positions (using SEQ ID NO: 8 for the amino acid numbering) selected from the group of:

1, 3, 4, 17, 18, 20, 23, 24, 28, 56, 61, 62, 67, 68, 80, 81, 84, 85, 91, 92, 106, 110, 114, 119, 121, 122, 123, 124, 125, 126, 127, 129, 131, 134, 136, 172, 185, 196, 206, 217, 218, 231, 232, 235, 246, 247, 249, 251, 257, 278, 310, 316, 317, 328, 332, 355, 358, 363, 367, 370, 373, 375, 376, 381, 382, 391, 396, 413, 414, 415, 416, 417, 418, 419, 420, 421, 422, 439, 445, 446, 448, 450, 454, 455, 458, 459, 460, 461, 463, 464, 465, 467 wherein
(a) the alteration(s) are independently
  (i) an insertion of an amino acid downstream of the amino acid which occupies the position, or (ii) a deletion of the amino acid which occupies the position,
(b) the variant has alpha-amylase activity and (c) each position corresponds to a position of the amino acid sequence of the parent Termamyl-like alpha-amylase having the amino acid sequence shown in SEQ ID NO: 8.

In the *Bacillus licheniformis* alpha-amylase shown in SEQ ID NO: 8 the positions to be mutated are one or more of:
A1, L3, N4, N17, D18, Q20, R23, R24, D28, Y56, L61, Y62, F67, H68, K80, G81, Q84, S85, H91, S92, K106, D110, D114, E119, D121, P122, A123, D124, R125, N126, R127, I129, G131, L134, K136, N172, E185, L196, P206, T217, W218, D231, A232, H235, N246, H247, R249, K251, F257, N278, G310, H316, P317, D328, G332, E355, Y358, Y363, Y367, K370, S373, R375, E376, K381, H382, R391, Y396, R413, E414, G415, D416, S417, S418, V419, A420, N421, S422, Y439, A445, G446, T448, H450, G454, N455, E458, P459, V460, V461, N463, S464, E465, W467.

Specific insertions/deletions contemplated are:
A1 insertion;
L3 insertion;
N4 insertion;
N17 insertion;
D18 insertion;
Q20 insertion;
R23 insertion;
R24 insertion;
D28 insertion;
Y56 insertion;
L61 insertion or deletion;
Y62 insertion;
F67 insertion or deletion;
H68 insertion;
K80 insertion or deletion;
G81 insertion or deletion;
Q84 insertion;
S85 insertion;
H91 insertion or deletion;
S92 insertion or deletion;
K106 insertion or deletion;
D110 insertion or deletion;
D114 deletion;
E119 insertion or deletion;
D121 insertion;
P122 insertion;
A123 insertion;
D124 insertion;
R125 insertion;
N126 insertion;
R127 insertion;
I129 insertion;
G131 insertion;
L134 insertion;
K136 insertion;
N172 insertion;
E185 insertion;
L196 insertion or deletion;
P206 insertion or deletion;
T217 insertion;
W218 insertion;
D231 insertion or deletion;
A232 insertion or deletion;
H235 insertion or deletion;
N246 insertion;
H247 insertion;
R249 insertion;
K251 insertion;
F257 insertion or deletion;
N278 insertion;
G310 insertion or deletion;
H316 insertion;
P317 insertion;
D328 insertion or deletion;
G332 insertion or deletion;
E355 insertion or deletion;
Y358 insertion;
Y363 insertion;
Y367 insertion;
K370 insertion;
S373 insertion;
R375 insertion;
E376 insertion;
K381 insertion;
H382 insertion;
R391 insertion or deletion;
Y396 insertion;
R413 insertion or deletion;
E414 insertion or deletion;
G415 insertion or deletion;
D416 insertion;
S417 insertion;
S418 insertion;
V419 insertion;
A420 insertion;
N421 insertion;
S422 insertion or deletion;
Y439 insertion;
A445 insertion or deletion;
G446 insertion or deletion;
T448 insertion or deletion;
H450 insertion;
G454 insertion or deletion;
N455 insertion;
E458 insertion;
P459 insertion;
V460 insertion;
V461 insertion;
N463 insertion;
S464 insertion;
E465 insertion;
W467 insertion
where each position corresponds to a position of the amino acid sequence of the parent Termamyl-like alpha-amylase having the amino acid sequence shown in SEQ ID NO: 8 (*Bacillus licheniformis* alpha-amylase).

Also in the first aspect the invention relates to a variant of a parent Termamyl-like alpha-amylase, comprising an alteration at one or more positions (using SEQ ID NO: 8 for the amino acid numbering) selected from the group of:
7, 8, 10, 11, 12, 15, 19, 21, 22, 25, 40, 41, 43, 44, 46, 55, 59, 77, 78, 90, 95, 97, 98, 99, 100, 101, 102, 105, 109, 115, 118, 135, 139, 141, 195, 208, 215, 219, 236, 238, 240, 244, 248, 256, 258, 259, 312, 313, 320, 322, 323, 325, 326, 327, 330, 331, 348, 349, 350, 359, 360, 365, 366, 369, 377, 384, 388, 423, 424, 438, 441, 449, 462, 479, 480, 481
wherein
(a) the alteration(s) are independently
(i) an insertion of an amino acid downstream of the amino acid which occupies the position, or
(ii) a deletion of the amino acid which occupies the position,
(b) the variant has alpha-amylase activity and (c) each position corresponds to a position of the amino acid sequence of the parent Termamyl-like alpha-amylase having the amino acid sequence shown in SEQ ID NO: 8.

In the *Bacillus licheniformis* alpha-amylase shown in SEQ ID NO: 8 the positions to be mutated are one or more of: L7, M8, Y10, F11, E12, M15, G19, H21, W22, L25, V40, W41, P43, P44, Y46, G55, Y59, Y77, G78, L90, I95, V97, Y98, G99, D100, V101, V102, H105, A109, V115, V118, I135, T139, F141, Y195, V208, W215, Y219, I236, F238, F240, W244, V248, M256, T258, V259, V312, V313, S320, T322, F323, D325, N326, H327, Q330, P331, Y348, A349, F350, P359, Q360, D365, M366, T369, I377, I384, L388, G423, L424, M438, G441, W449, I462, I479, Y480, V481.

Specific insertions/deletions contemplated are:
L7 insertion or deletion;
M8 insertion;
Y10 insertion;
F11 insertion;
E12 insertion or deletion;
M15 insertion;
G19 insertion;
H21 insertion;
W22 insertion;
L25 insertion;
V40 insertion or deletion;
W41 insertion;
P43 insertion or deletion;
P44 insertion or deletion;
Y46 insertion;
G55 insertion;
Y59 insertion;
Y77 insertion;
G78 insertion or deletion;
L90 insertion or deletion;
I95 insertion;
V97 insertion;
Y98 insertion;
G99 insertion;
D100 insertion;
V101 insertion;
V102 insertion;
H105 insertion or deletion;
A109 insertion or deletion;
V115 insertion or deletion;
V118 insertion or deletion;
I135 insertion;
T139 insertion or deletion;
F141 insertion or deletion;
Y195 insertion;
V208 insertion or deletion;
W215 insertion;
Y219 insertion;
I236 insertion or deletion;
F238 insertion or deletion;
F240 insertion or deletion;
W244 insertion;
V248 insertion;
M256 insertion;
T258 insertion or deletion;
V259 insertion or deletion;
V312 insertion or deletion;
V313 insertion or deletion;
S320 insertion;
T322 insertion or deletion;
F323 insertion or deletion;
D325 insertion or deletion;
N326 insertion;
H327 insertion or deletion;
Q330 insertion or deletion;
P331 insertion or deletion;
Y348 insertion;
A349 insertion or deletion;
F350 insertion or deletion;
P359 insertion or deletion;
Q360 insertion;
D365 insertion or deletion;
M366 insertion;
T369 insertion;
I377 insertion;
I384 insertion or deletion;
L388 insertion or deletion;
G423 insertion or deletion;
L424 insertion or deletion;
M438 insertion;
G441 insertion or deletion;
W449 insertion;
I462 insertion;
I479 insertion or deletion;
Y480 insertion;
V481 insertion or deletion;
where each position corresponds to a position of the amino acid sequence of the parent Termamyl-like alpha-amylase having the amino acid sequence shown in SEQ ID NO: 8 (*Bacillus licheniformis* alpha-amylase).

Corresponding positions in other parent alpha-amylases can be found by alignment as described above and shown in the alignment in FIG. 1.

Stability

In the context of the present invention, mutations (including amino acid substitutions and deletion) of importance with respect to achieving altered stability, in particular improved stability (i.e., higher or lower), at especially high temperatures (i.e., 70-120° C.) and/or extreme pH (i.e. low or high pH, i.e, pH 4-6 or pH 8-11, respectively), in particular at free (i.e., unbound, therefore in solution) calcium concentrations below 60 ppm, include any of the mutations listed in the "Altered Properties" section. The stability may be determined as described in the "Materials & Methods" section below.

$Ca^{2+}$ Stability

Altered $Ca^{2+}$ stability means the stability of the enzyme under $Ca^{2+}$ depletion has been improved, i.e., higher or lower stability. In the context of the present invention, mutations (including amino acid substitutions and deletions) of importance with respect to achieving altered $Ca^{2+}$ stability, in particular improved $Ca^{2+}$ stability, i.e., higher or lower stability, at especially high pH (i.e., pH 8-10.5) include any of the mutations listed in the in "Altered properties" section.

Specific Activity

In a further aspect of the present invention, important mutations (including amino acid substitutions and deletions) with respect to obtaining variants exhibiting altered specific activity, in particular increased or decreased specific activity, especially at temperatures from 10-60° C., preferably 20-50° C., especially 30-40° C., include any of the mutations listed in the in "Altered properties" section. The specific activity may be determined as described in the "Material & Methods" section below.

Oxidation Stability

Variants of the invention may have altered oxidation stability, in particular higher oxidation stability, in comparison to the parent alpha-amylase. Increased oxidation stability is advantageous in, e.g., detergent compositions and descresed oxidation stability may be advantageous in composition for starch liquefaction. Oxidation stability may be determined as described in the "Material & Methods" section below.

Altered pH Profile

Important positions and mutations with respect to obtaining variants with altered pH profile, in particular improved activity at especially high pH (i.e., pH 8-10.5) or low pH (i.e., pH 4-6) include mutations of amino residues located dose to the active site residues.

Preferred specific mutations/substitutions are the ones listed above in the section "Altered Properties" for the positions in question. Suitable assays are described in the "Materials & Methods" section below.

Wash Performance

Important positions and mutations with respect to obtaining variants with improved wash performance at especially high pH (i.e., pH 8.5-11) include the specific mutations/substitutions listed above in the section "Altered Properties" for the positions in question. The wash performance may be tested as described below in the "Materials & Methods" section.

Increased pI

Substitutions Resulting in Higher pI

In an aspect the invention relates to a variant with a higher pI than the parent alpha-amylase. Such variants are suitable when adjusting the pI to the washing conditions of various detergents. This means that if the pI of the parent alpha-amylase is below the pH in the washing solution the target is to increase the pI to the pH of the washing solution. Such variant may be prepared by making the following kind of substitutions:

1) Substituting one or more of the below mentioned negatively charged amino acid residue in a parent alpha-amylase with a positively charged amino acid residue.
2) Substituting one or more of the below mentioned neutral amino acid residue in a parent alpha-amylase with a positively charged amino acid residue;
3) Substituting one or more of the below mentioned negatively charged amino acid residue in a parent alpha-amylase with a neutral amino acid residue;
4) Substituting one or more of the below mentioned positively charged amino acid residue in a parent alpha-amylase with a more positively charged amino acid residue;

Variants of the invention with increased pI in comparison to the parent alpha-amylase may have improved-wash performance. Wash performance tests may be carried out as described in the "Materials & Method" section.

Thus, variants of the invention include (using SEQ ID NO: 8 for the numbering):
G5R,K,H;
T6R,K,H;
G36R,K,H;
I37R,K,H;
T38R,K,H;
A39R,K,H;
I42R,K,H;
A45R,K,H;
D63A,R,N,C,Q,G,H,I,L,K,M,F,P,S,T,W,Y,V;
E66A,R,N,C,Q,G,H,I,L,K,M,F,P,S,T,W,Y,V;
Q69R,K,H;
G71R,K,H;
T72R,K,H;
T75R,K,H;
T79R,K,H;
E82A,R,N,C,Q,G,H,I,L,K,M,F,P,S,T,W,Y,V;
L83R,K,H;
A86R,K,H;
I87R,K,H;
S89R,K,H;
T112R,K,H;
E113A,R,N,C,Q,G,H,I,L,K,M,F,P,S,T,W,Y,V;
A117R,K,H;
V120R,K,H;
A137R,K,H;
G216R,K,H;
A220R,K,H;
L223R,K,H;
L225R,K,H;
D226A,R,N,C,Q,G,H,I,L,K,M,F,P,S,T,W,Y,V;
G227R,K,H;
D243A,R,N,C,Q,G,H,I,L,K,M,F,P,S,T,W,Y,V;
V245R,K,H;
F279R,K,H;
S282R,K,H;
T311R,K,H;
V321R,K,H;
V324R,K,H;
L352R,K,H;
T353R,K,H;
G357R,K,H;
V361R,K,H;
F362R,K,H;
G364R,K,H;
G368R,K,H;
A390R,K,H;
A395R,K,H;
G397R,K,H;
Q399R,K,H;
H400R,K,H;
D401A,R,N,C,Q,G,H,I,L,K,M,F,P,S,T,W,Y,V;
A425R,K,H;
D451A,R,N,C,Q,G,H,I,L,K,M,F,P,S,T,W,Y,V;
I452R,K,H;
T453R,K,H;
G466R,K,H;
G468R,K,H;
F470R,K,H;
S478R,K,H;
L7R,K,H;
Q9R,H;
F11H;
E12A,R,N,C,G,H,I,L,K,M,F,P,S,T,W,Y,V;
G19R,K,H;
W22R,K,H;
L25R,K,H;
L32R,K,H;
V40R,K,H;
W41R,K,H;
Y46R,K;
G48R,K,H;
G55R,K,H;
G57R,K,H;
A58R,K,H;
D60A,R,C,Q,G,H,I,L,K,M,F,P,S,T,W,Y,V;
Y77R,K;
I95R,K,H;
V97R,K,H;
Y98R,K;
G99R,K,H;
D100A,R,C,Q,G,H,I,K,M,F,P,S,T,W,Y,V;
V102H;
G107R,K,H;
V115R,K,H;
V118R,K,H;
I135R,K,H;
T139R,K,H;
F141R,K,H;

F143R,K,H;
S151R,K,H;
F160R,K,H;
D161R,K,H;
G162R,K,H;
T163R,K,H;
D166A,R,N,C,Q,G,H,I,L,K,M,F,P,S,T,W,Y,V;
Y175R,K;
F177K,H;
D183A,R,C,Q,G,H,I,L,K,M,F,P,S,T,W,Y,V;
V186R,K,H;
S187R,K,H;
N192R,K,H;
A199R,K,H;
D200A,R,C,Q,G,H,I,L,K,M,F,P,S,T,W,Y,V;
D202A,R,C,Q,G,H,I,L,K,M,F,P,S,T,W,Y,V;
Y203R,K;
V208R,K,H;
I212H;
W215R,K,H;
Y219R,K;
F228R,K,H;
L230R;
V233R,K,H;
I236H;
F238R,K,H;
F240R,K,H;
L241H;
W244R,K,H;
V248R,K,H;
T258R,K,H;
V259R,K,H;
A260R,K,H;
Y262R,K;
Y273R,K;
L274R,K,H;
T277R,K,H;
H281R,K;
V283R,K;
F284R,K;
D285A,R,C,Q,G,H,I,K,M,F,P,S,T,W,Y,V;
V286R,K,H;
P287R,H;
L288R,K,H;
H289R,K;
F292R,K,H;
A295R,K,H;
S296R,K,H;
L307R,K,H;
V312H;
V313R,K,H;
S320R,K,H;
T322R,K,H;
F323R,K;
D325A,R,C,Q,G,H,I,L,K,M,F,P,S,T,W,Y,V;
N326R;
T329R,K,H;
P331H;
V339R,H,K;
F343R,H,K;
K344H;
L346R,K,H;
A347R,K,H;
A349R,K,H;
F350R,K,H;
P359R,K,H;
Q360H;
T369R,K,H;
I377R,K,H;
L380R,K,H;
I387R,K,H;
V409H;
G410R,K,H;
W411R,K,H;
T412R,K,H;
G423R,K,H;
L424R,K,H;
A426R,K,H;
L427R,K,H;
I428H;
T429R,K,H;
D430A,R,C,Q,G,H,I,L,K,M,F,P,S,T,W,Y,V;
V440R,K,H;
G441R,K,H;
W449R,K,H;
I462R,K,H;
V472R,K,H;
V477R,K,H;
I479R,K,H;
Y480R,K;
V481R,K,H;
A1R,K,H;
N2R,K,H;
L3R,K,H;
N4R,K,H;
W13R,K,H;
Y14R,K;
P16R,K,H;
N17R,K,H;
D18A,R,N,C,Q,E,G,H,I,L,K,M,F,P,S,T,W,Y,V;
Q20R,K,H;
R23H;
R24K,H;
Q26H;
E34A,R,N,C,Q,G,H,I,L,K,M,F,P,T,W,Y,V;
T49H;
S50R,K,H;
Q51H;
A52R,K,H;
D53A,C,G,H,K,M,P;
L61R,K,H;
Y62R,K;
F67R,K,H;
V73R,K,H;
Q84R,K,H;
S85R,K,H;
K88H;
S92R,H;
N96R,K,H;
K106H;
G108R,K,H;
D114A,N,C,Q,G,H,K,F,P,S,T,W,Y;
T116R,H;
E119A,R,N,D,Q,G,H,I,L,K,M,F,P,S,T,W,Y,V;
D121A,R,C,Q,G,H,I,L,K,M,F,P,S,T,W,Y,V;
P122R,H;
A123H;
D124N,Q,G,H,I,L,M,F,P,S,T,W,Y,V;
R125K;
N126H;
R127K,H;
V128R,K,H;
I129R,K,H;
S130R,K,H;

G131R,K,H;
E132R,N,D,C,Q,G,H,I,L,K,M,F,S,W,Y;
L134K,H;
K136A,R,N,D,C,E,G,H,I,L,M,F,P,S,T,W,Y,V;
W138R,K;
G145R,K,H;
G147R,K,H;
S148R,K,H;
T149R,K,H;
D152A,R,N,C,Q,G,H,I,L,K,M,F,P,T,W,Y,V;
F153R,K,H;
K154H;
W155R,K,H;
W157R;
Y158R;
D164R,I,L,M,F,P,S,T,W,Y,V;
W165K,H;
E167A,R,N,D,C,Q,G,H,I,L,K,M,F,P,S,T,W,Y,V;
S168R,K,H;
R169H;
K170H;
L171R,K,H;
R173H;
K176H;
G179K,H;
W182R,K,H;
E185R,I,L,M,F,P,S,T,W,Y,V;
N188R,H;
E189A,R,N,G,H,I,L,M,F,P,S,T,W,Y,V;
G191R,H;
Y193R;
L196H;
Y198R;
D204R,L,M,F,P,T,W,Y,V;
P206R,K,H;
A209R;
A210R,K,H;
T217R,H;
W218R,K,H;
N221R,K,H;
E222R,K,H;
K234H;
K237H;
S239H;
N246R,K,H;
R249H;
E250A,R,N,D,C,H,I,L,K,M,P,T,W,Y,V;
K251H;
T252R,K,H;
G253R,K,H;
K254H;
E255A,R,D,C,G,H,I,L,K,M,F,S,T,W,Y,V;
F257R,K,H;
E261A,R,N,D,C,Q,G,H,I,L,K,M,F,P,S,T,W,Y,V;
W263R,K;
N265H;
D266A,R,N,C,Q,G,H,I,L,K,M,F,P,S,T,W,Y,V;
L267R,K,H;
G268R,K,H;
A269H;
E271A,R,N,D,C,Q,G,H,I,L,K,M,F,P,S,T,W,Y,V;
N272R,K,H;
N275R,K,H;
K276H;
N278R,K,H;
N280R,K,H;
Q291R,H;
A294R,H;
T297H;
Q298H;
G299H;
G300H;
G301H;
Y302R;
D303R,I,L,M,F,P,S,T,W,Y,V;
K306H;
L308R,K,H;
N309H;
G310R,K,H;
K315H;
P317R,K,H;
L318R,K,H;
K319H;
D328A,R,N,C,Q,G,H,I,L,K,M,F,P,S,T,W,Y,V;
G332R,K,H;
S334R,K,H;
L335R,K,H;
E336A,N,D,C,Q,G,H,I,L,M,F,P,S,T,W,Y,V;
S337R,H;
T338R,K,H;
T341R,K,H;
W342R;
P345R,K,H;
E355A,R,N,D,C,Q,G,H,I,L,K,M,F,P,S,T,W,Y,V;
Y358R,K;
Y363R,K;
K370H;
G371K,H;
S373R,K,H;
Q374K,H;
R375H;
E376A,R,N,D,C,Q,G,H,I,L,M,F,P,S,T,W,Y,V;
P378R,K,H;
A379R,K,H;
K381H;
K389H;
Q393K,H;
Y394R,K;
Y396R,M;
A398R,H;
Y402R,K;
F403R,H;
D404R,I,L,M,F,P,S,T,W,Y,V;
H406R;
D407A,R,Q,G,H,I,L,M,F,P,S,T,W,Y,V;
I408R,K,H;
R413K,H;
E414A,R,N,D,C,Q,G,H,I,L,K,M,F,P,S,T,W,Y,V;
G415R,K,H;
D416A,R,N,C,Q,G,H,I,L,K,M,F,P,S,T,W,Y,V;
S417R,K,H;
S418R,K,H;
V419R,H;
A420K,H;
N421R,K,H;
S422R,K,H;
G431R,H;
P432H;
G433R,H;
G434R;
A435H;
K436H;
R437K,H;
Y439R,K;

R442H;
Q443R,H;
N444H;
A445R,K,H;
G446R,K,H;
E447A,N,D,C,G,H,I,L,M,F,P,S,T,W,Y,V;
T448R,K,H;
G454R,K,H;
N455R,K,H;
R456H;
S457R,K,H;
E458A,R,N,C,Q,G,H,I,L,K,M,F,P,S,T,W,Y,V;
P459R,K,H;
V460R,K,H;
V461R,H;
N463R,K,H;
S464R,K,H;
E465A,R,N,C,Q,G,H,I,L,K,M,F,P,S,T,W,Y,V;
W467R,K,H;
E469A,R,N,D,C,Q,G,H,I,L,K,M,F,P,S,T,W,Y,V;
N473H;
G474R,H;
G475H;
S476H;
Q482H;
R483H.

Decreased pI
Substitutions Resulting in Lower pI

Variants of the invention with decreased pI in comparison to the parent alpha-amylase may have improved liquefying effect. This means that the pI of the parent amylase should be adjusted to the pH conditions in the liquefying process in question. Normally the pH during liquefaction lies in the range of 4-7, such as between pH 4.5-6.5. An example of a liquefaction process is descripted below in the section "Liquefaction". Improved liquefying effect may be carried out as described in the "Materials & Method" section.

Alternatively, variants with decreased pI may advantageously be used in detergent. If the pI of the parent alpha-amylase is above the pH in the washing solution the target is to decrease the pI to the pH of the washing solution. Such variant may be prepared by making the following kind of substitutions:

1) Substituting one or more of the below mentioned positively charged amino acid residue in a parent alpha-amylase with a neutral amino acid residue.
2) Substituting one or more of the below mentioned neutral amino acid residue in a parent alpha-amylase with a negatively charged amino acid residue.
3) Substituting one or more of the below mentioned positively charged amino acid residue with a negatively charged amino acid residue.
4) Substituting one or more of the below mentioned negatively charged amino acid residue with a more negatively charged amino acid residue.

Thus, variants of the invention include (using SEQ ID NO: 8 for the numbering):
G5D,E;
T6D,E;
G36D,E;
I37D,E;
T38D,E;
A39D,E;
I42D,E;
A45D,E;
K47A,R,N,D,C,Q,E,G,H,M,F,P,S,T,W,Y,V;
D63E;
Q69D,E;
K70A,N,D,C,Q,E,G,I,M,F,P,S,T,W,Y,V;
G71D,E;
T72D,E;
R74A,N,D,C,Q,E,G,I,M,F,P,S,T,W,Y,V;
T75D,E;
K76A,N,D,C,Q,E,G,L,M,F,P,S,T,W,Y,V;
T79D,E;
L83D,E;
A86D,E;
I87D,E;
S89D,E;
R93A,N,D,C,Q,E,G,I,L,M,F,P,S,T,W,Y,V;
T112D,E;
A117D,E;
V120D,E;
A137D,E;
K213A,N,D,C,Q,E,G,I,L,M,F,P,S,T,W,Y,V;
G216D,E;
A220D,E;
L223D,E;
L225D,E;
D226E;
G227D,E;
R229A,N,D,C,Q,E,G,I,L,M,F,P,S,T,W,Y,V;
D243E;
V245D,E;
F279D,E;
S282D,E;
T311D,E;
V321D,E;
V324D,E;
L352D,E;
T353D,E;
R354A,N,D,C,Q,E,G,I,L,M,F,P,S,T,W,Y,V;
G357D,E;
V361D,E;
F362D,E;
G364D,E;
G368D,E;
A390D,E;
A395D,E;
G397D,E;
Q399D,E;
H400A,N,D,C,Q,E,G,I,L,M,F,P,S,T,W,Y,V;
D401E;
A425D,E;
D451E;
I452D,E;
T453D,E;
G466D,E;
G468D,E;
F470D,E;
H471A,N,D,C,Q,E,G,I,L,M,F,P,S,T,W,Y,V;
S478D,E;
L7D,E;
Q9D;
F11D;
G19D,E;
H21R,D,E,K;
W22D,E;
L25D,E;
L32D,E;
V40D,E;
W41D,E;
Y46D;
G48D,E;

G55D,E;
G57D,E;
A58D,E;
D60E;
Y77D;
I95D,E;
V97D,E;
Y98D;
G99D,E;
D100E;
V102D,E;
I103A,D,E;
H105A,N,C,Q,G,I,L,M,P,S,T,Y,V;
G107D,E;
V115D,E;
V118E;
I135D,E;
T139D,E;
F141D,E;
F143A,D,E;
S151D,E;
H159A,R,N,D,C,Q,E,G,I,L,K,M,F,P,S,T,W,V;
F160D,E;
D161E;
G162D,E;
T163D,E;
Y175D;
F177D,E;
D183E;
V186D,E;
S187E;
N192D,E;
A199D,E;
D200E;
D202E;
Y203D;
V208D,E;
W215D,E;
Y219D;
F228D,E;
L230D,E;
V233E;
F238D,E;
F240D,E;
W244D,E;
V248D,E;
T258D,E;
V259D,E;
A260D,E;
Y262D;
Y273D;
L274D,E;
T277D,E;
H281A,R,N,D,C,Q,E,G,K,M,P,S,T,W,Y,V;
V283E;
F284D,E;
D285E;
V286D,E;
P287D,E;
L288D,E;
H289A,R,N,D,C,Q,E,G,I,L,K,M,F,P,S,T,W,Y,V;
F292D,E;
A295D,E;
S296D,E;
L307D,E;
V313D,E;
S320D,E;
T322D,E;
F323D,E;
D325E;
N326E;
H327A,R,C,G,I,L,K,M,P,S,T,W,Y,V;
T329D,E;
P331D,E;
V339E;
F343D,E;
K344A,R,N,D,C,Q,E,G,I,L,M,F,P,S,T,W,Y,V;
L346D,E;
A347D,E;
A349D,E;
P359D,E;
Q360D;
T369D,E;
I377D,E;
L380D,E;
I387D,E;
V409E;
G410D,E;
W411D,E;
T412E;
G423D,E;
L424D,E;
A426D,E;
L427D,E;
I428D,E;
T429D,E;
D430E;
V440D,E;
G441D,E;
W449D,E;
I462D,E;
V472D,E;
V477D,E;
I479D,E;
Y480D;
V481D,E;
A1D,E;
N2D,E;
L3D,E;
N4D,E;
W13D,E;
Y14D;
P16D,E;
N17D,E;
D18E;
Q20D,E;
R23D,E;
R24D,E;
Q26D,E;
H35A,R,N,D,C,Q,E,G,K,M,F,P,S,T,W,Y,V;
S50E;
Q51D,E;
A52D,E;
L61D,E;
Y62D;
F67D,E;
H68A,R,D,C,E,G,I,L,K,M,F,P,S,T,W,Y,V;
V73D,E;
Q84D;
S85E;
K88A,R,N,D,C,E,G,I,L,M,F,P,S,T,W,Y,V;
H91A,R,N,D,C,Q,E,G,I,L,M,F,P,S,T,W,Y,V;
S92D,E;
N96D,E;

K106A,N,D,C,Q,E,G,I,L,M,P,S,T,Y,V;
G108D,E;
D114E;
T116D,E;
D121E;
A123D,E;
R125N,Q,E,G,I,M,F,S,T,W,Y;
R127D,E;
V128D;
I129D,E;
S130D,E;
G131D;
H133R,N,D,C,M,T,W,V;
L134D,E;
K136A,R,N,D,C,E,G,I,L,M,F,P,S,T,W,Y,V;
W138D,E;
G145D,E;
G147D,E;
S148D,E;
T149D,E;
Y150D;
D152E;
F153D,E;
K154A,R,N,D,C,Q,E,G,I,L,M,F,P,S,T,W,Y,V;
W155D,E;
H156A,C,Q,E,G,I,L,M,F,P,S,T,W,V;
W165D,E;
S168D,E;
R169D,E;
K170A,R,N,D,C,E,G,I,L,M,F,P,S,T,W,Y,V;
L171D,E;
N172D,E;
R173A,N,D,C,Q,E,G,M,P,S,W,Y,V;
K176A,N,D,C,Q,E,G,I,L,M,F,P,S,T,W,Y,V;
G179D,E;
K180A,G,I,L,M,F,P,W,Y,V;
W182D,E;
P206D,E;
A210D,E;
R214A,D,C,Q,E,G,I,L,M,F,P,S,T,Y,V;
T217D;
W218D,E;
N221D,E;
K234A,D,C,G,I,M,F,P,S,T,W,Y,V;
H235A,R,N,D,C,Q,E,G,I,L,K,M,F,P,S,T,W,Y,V;
K237A,G,I,L,M,F,W,Y,V;
R242G,I,L,M,F,S,T,W,Y,V;
N246D,E;
H247R,N,D,C,Q,E,G,I,L,K,M,F,P,S,T,W,Y,V;
R249A,N,D,C,Q,E,G,I,L,M,F,P,S,T,W,Y,V;
K251R,N,D,C,E,G,I,L,M,F,P,S,T,W,Y,V;
T252D,E;
G253E;
K254A,R,N,D,C,Q,E,G,I,L,M,F,P,S,T,W,Y,V;
F257D,E;
W263D,E;
N265E;
D266E;
L267D,E;
G268D,E;
N272D,E;
N275D,E;
K276A,R,N,D,C,Q,E,G,I,L,M,F,P,S,T,W,Y,V;
N278D,E;
N280D,E;
H293A,R,N,G,I,L,M,P,S,T,W,V;
R305G,I,L,M,F,P,S,T,W,Y,V;
K306Q,G,I,L,M,F,P,S,T,W,Y,V;
L308D,E;
G310E;
S314D,E;
K315A,N,C,Q,E,G,I,L,M,F,P,S,T,W,Y,V;
H316A,R,N,D,C,Q,E,G,I,L,K,M,F,P,S,T,W,V;
P317D,E;
L318D,E;
K319A,R,N,D,C,Q,E,G,I,L,M,F,P,S,T,W,Y,V;
D328E;
G332E;
Q333D;
S334E;
L335D,E;
S337E;
T341D;
P345D,E;
Y358D;
Y363D;
K370A,R,N,D,C,Q,E,G,I,L,M,F,P,S,T,W,Y,V;
G371E;
S373D,E;
Q374D,E;
R375A,N,D,C,Q,G,I,L,M,F,P,S,T,W,V;
P378D,E;
A379D,E;
K381A,R,N,D,C,Q,E,G,I,L,M,F,P,S,T,W,Y,V;
K389A,D,C,G,M,F,P,S,T,W,Y,V;
Q393E;
Y394D;
Y396D;
A398D,E;
H405R,G,I,L,M,F,P,W,Y,V;
H406A,R,G,I,M,F,P,Y,V;
I408D,E;
R413A,N,D,C,Q,E,G,I,L,M,F,P,S,T,W,Y,V;
G415D,E;
D416E;
S417D,E;
S418D,E;
V419D,E;
A420D,E;
N421D,E;
S422D,E;
K436A,R,N,D,C,Q,E,G,I,L,M,F,P,S,T,W,Y,V;
R437A,N,D,C,Q,E,G,I,L,M,F,P,S,T,W,Y,V;
Y439D;
R442A,N,D,C,E,G,I,L,M,F,P,S,T,W,Y,V;
Q443D,E;
A445D,E;
G446D,E;
T448D,E;
H450A,N,D,C,Q,E,G,I,L,K,M,F,P,S,T,W,V;
G454D,E;
R456A,D,C,E,G,I,L,M,F,P,S,T,W,Y,V;
S457D,E;
P459D,E;
V460D,E;
V461D,E;
N463D,E;
S464D,E;
W467D,E;
Q482D;
R483A,N,D,C,Q,E,G,I,L,M,F,P,S,T,W,Y,V.

Reduced Sensitivity to Anionic Surfactants
Substitutions Resulting in a More Hydrophilic Amino Acid Residue In an aspect, the invention relates to providing alpha-amylase variants with reduced sensitivity (or improved stability against denaturation) to anionic surfactants (in particular linear alkyl sulphonates (LAS)). These variants are provided by substituting, deleting or inserting an amino acid residue in the parent alpha-amylase as indicated below with a more hydrophilic amino acid residue. Such variants may be prepared by:
1) Substituting one or more of the below mentioned positively charged amino acid residue in a parent alpha-amylase with a hydrophilic amino acid residue.
2) Substituting one or more of the below mentioned hydrophobic amino acid residue in a parent alpha-amylase with a hydrophilic amino acid residue
3) Substituting one or more of the below mentioned positively charged amino acid residue in a parent alpha-amylase with a neutral or negatively charged amino acid residue.

The anionic surfactants (in particular linear alkyl sulphonates (LAS)) sensitivity (in detergent) may be tested as described in the "Materials & Methods" section.

Variants of the invention with reduced sensitivity to anionic surfactants, in particular linear alkyl sulphonates (LAS), include (using the *Bacillus licheniformis* alpha-amylase shown in SEQ ID NO: 8 numbering):

G5N,C,Q,S,T;
T6N,C,Q,S;
G36N,C,Q,S,T;
I37N,C,Q,S,T;
T38N,C,Q,S;
A39N,C,Q,S,T;
I42N,C,Q,S,T;
A45N,C,Q,S,T;
K47N,C,Q,S,T,A,I,L,M,F,P,W,Y,V,D,E;
Q69N;
K70N,C,Q,S,T,A,I,L,M,F,P,W,Y,V,D,E;
G71N,D,C,Q,S,T;
T72N,C,Q,S;
R74N,C,Q,S,T,A,I,L,M,F,P,W,Y,V,D,E;
T75N,C,Q,S;
K76N,C,Q,S,T,A,I,L,M,F,P,W,Y,V,D,E;
T79N,C,Q,S;
L83N,C,Q,S,T;
A86N,C,Q,S,T;
I87N,C,Q,S,T;
S89N,C,Q;
R93N,C,Q,S,T,A,I,L,M,F,P,W,Y,V,D,E;
T112N,C,Q,S;
A117N,C,Q,S,T;
V120N,C,Q,S,T;
A137N,C,Q,S,T;
K213N,C,Q,S,T,A,I,L,M,F,P,W,Y,V,D,E;
G216N,C,Q,S,T;
A220N,C,Q,S,T;
L223N,C,Q,S,T;
L225N,C,Q,S,T;
G227N,C,Q,S,T;
R229N,C,Q,S,T,A,I,L,M,F,P,W,Y,V,D,E;
V245N,C,Q,S,T;
F279N,C,Q,S,T;
S282N,C,Q;
T311N,C,Q,S;
V321N,C,Q,S,T;
V324N,C,Q,S,T;
L352N,C,Q,S,T;
T353N,C,Q,S;
R354N,C,Q,S,T,A,I,L,M,F,P,W,Y,V,D,E;
G357N,C,Q,S,T;
V361N,C,Q,S,T;
F362N,C,Q,S,T;
G364N,C,Q,S,T;
G368N,C,Q,S,T;
A390N,C,Q,S,T;
A395N,C,Q,S,T;
G397N,C,Q,S,T;
Q399N;
H400N,C,Q,S,T,A,I,L,M,F,P,W,Y,V,D,E;
A425N,C,Q,S,T;
I452N,C,Q,S,T;
T453N,C,Q,S;
G466N,C,Q,S,T;
G468N,C,Q,S,T;
F470N,C,Q,S,T;
H471N,C,Q,S,T,A,I,L,M,F,P,W,Y,V,D,E;
S478N,C,Q;
L7N,C,Q,S;
M8C;
Q9N;
F11N,C,Q,S,T;
G19N,C,Q,S,T;
H21N,C,Q,S,T,A,I,L,M,F,P,W,Y,V,D,E;
W22N,C,Q,S,T;
L25N,C,Q,S,T;
L32N,C,Q,S,T;
V40N,C,Q,S,T;
W41N,C,Q,S,T;
Y46C;
G48N,C,Q;
G55N,C,Q,S,T;
G57N,C,Q;
A58N,C,Q,S,T;
Y77C;
I95N,C,Q,S,T;
V97N,C,Q,S,T;
Y98C;
G99N,C,Q,S,T;
V101N,C,Q,S,T;
V102N,C,Q;
I103N,C,Q,S;
H105N,C,Q,S,T,A,I,L,M,P,Y,V;
G107N,Q;
V115N,C,Q,S,T;
V18N,C,Q,S,T;
I135N,C,Q,S,T;
T139N,C,Q,S;
F141N,C,Q,S,T;
F143N,C,Q,S,T;
S151N,C,Q;
H159N,C,Q,S,T,A,I,L,M,F,P,W,Y,V,D,E;
F160N,C,Q,S,T;
G162N,C,Q,S,T;
T163N,C,Q,S;
Y175C;
F177N,C,Q,S,T;
V186N,C,Q,S,T;
S187C,Q;
A199N,C,Q,S,T;
Y203C;
V208N,C,Q,S,T;
I212N,C,Q,S,T;
W215N,C,Q,S,T;
Y219C;
F228N,C,Q,S,T;

L230N,C,Q,S,T;
V233N,C,Q,S,T;
I236C,Q,S,T;
F238N,C,Q,S,T;
F240N,C,Q,S,T;
L241N,C,Q,S,T;
W244N,C,Q,S,T;
V248N,C,Q,S,T;
M256C;
T258N,C,Q,S;
V259N,C,Q,S,T;
A260N,C,Q,T;
Y262C;
L270N,C,Q,S,T;
Y273C;
L274N,C,Q,S,T;
T277N,C,Q,S;
H281N,C,Q,S,T,A,M,P,W,Y,V,D,E;
V283N,C,Q,S,T;
F284N,C,Q,S,T;
V286C,Q,S,T;
P287N,C,Q,S,T;
L288N,C,Q,S,T;
H289N,C,Q,S,T,A,I,L,M,F,P,W,Y,V,D,E;
F292N,C,Q,S,T;
A295N,C,Q,S,T;
S296N,C,Q,T;
M304C;
L307N,C,Q,S,T;
V312N,C,Q,S,T;
V313N,C,Q,S,T;
S320N,C,Q;
T322N,C,Q,S;
F323N,C,Q,S,T;
H327C,S,T,A,I,L,M,P,W,Y,V;
T329N,C,Q;
P331N,C,Q,S,T;
V339N,C,Q,S,T;
F343N,C,Q,S,T;
K344N,C,Q,S,T;
L346N,Q,S,T;
A347N,C,Q,S,T;
A349N,Q,S,T;
F350N,C,Q,S,T;
P359N,C,Q,S,T;
Q360N;
T369N,C,Q,S;
I377N,C,Q,S,T;
L380N,C,Q,S;
I387N,C,Q,S,T;
V409N,C,Q,S,T;
G410N,C,Q,S,T;
W411N,C,Q,S,T;
T412N,C,Q,S;
G423N,C,Q,S,T;
L424N,C,Q,S,T;
A426N,C,Q,S,T;
L427N,C,Q,S,T;
I428N,Q,S;
T429N,C,Q,S;
M438C;
V440N,C,Q,S,T;
G441N,C,Q,S,T;
W449N,C,Q,S,T;
I462N,C,Q,S,T;
V472N,C,Q,S,T;
V477N,C,Q,S,T;

I479N,Q,S;
Y480C;
V481N,C,Q,S,T;
A1N,C,Q,S,T;
L3N,C,Q,S,T;
N4C,Q,S,T;
W13N,C,Q,S,T;
Y14C;
P16N,C,Q,S,T;
Q20N;
R23N,C,Q,S,A,I,L,M,F,P,W,Y,V,D,E;
R24N,C,Q,S,T,A,I,L,M,F,P,W,Y,V,D,E;
H35N,C,Q,S,T,A,M,F,P,W,Y,V,D,E;
T49C;
S50N,C,Q;
Q51N;
A52C,Q;
L61N,C,Q,S,T;
Y62C;
F67N,C,Q,S,T;
H68C,S,T,A,I,L,M,F,P,W,Y,V,D,E;
V73N,C,Q,S,T;
Q84N;
S85N,C,T;
K88N,C,S,T,A,I,L,M,F,P,W,Y,V,D,E;
H91N,C,Q,S,T,A,I,L,M,F,P,W,Y,V,D,E;
S92N,C,Q;
K106N,C,Q,S,T,A,I,L,M,F,P,W,Y,V,D,E;
G108N,C,Q,S,T;
T116C,Q,S;
E119N,Q,S,T;
P122N,Q,S,T;
A123N,C,Q,S,T;
R125N,Q,S,T,I,M,F,W,Y,E;
R127N,S,T,A,I,L,M,F,P,W,Y,V,D,E;
V128N,C,Q,S;
I129N,C,Q,S;
S130N,Q;
G131N,C,Q,S,T;
H133N,C,T,M,W,V,D;
L134N,C,S,T;
K136N,C,S,T A,I,L,M,F,P,W,Y,V,D,E;
W138N,Q,S,T;
G145N,C,Q,S,T;
G147N,C,Q,S,T;
S148C,Q,T;
T149N,C,Q,S;
Y150C;
F153N,C,Q,S,T;
K154N,C,Q,S,T A,I,L,M,F,P,W,Y,V,D,E;
W155N,C,Q,S,T;
H156C,Q,S,T A,I,L,M,F,P,W,V,E;
W157S,T;
W165N,C,Q,S,T;
S168N,C,Q;
R169AN,C,Q,S A,M,P,W,Y,V,D,E;
K170N,C,S,T A,I,L,M,F,P,W,Y,V,D,E;
L171N,C,Q,S,T;
R173N,C,Q,S A,M,P,W,Y,V,D,E;
K176N,C,Q,S,T A,I,L,M,F,P,W,Y,V,D,E;
G179C,Q;
W182N,C,Q,S,T;
K180A,I,L,M,F,P,W,Y,V;
W182N,C,Q,S,T,A,I,L,M,F,P,W,Y,V,D,E;
W184I,L,M,F,P,W,Y,V;
G191N,Q,S,T;
L196N,Q,S,T;

P206N,C,Q,S,T;
A209S;
A210N,C,Q;
R214C,Q,S,T A,I,L,M,F,P,W,Y,V,D,E;
T217N,C,Q,S;
W218N,C,Q,S,T;
K234C,S,T A,I,M,F,P,W,Y,V,D;
H235N,C,Q,S,T A,I,L,M,F,P,W,Y,V;
R242S,T,I,L,M,F,W,Y,V;
H247N,C,Q,S,T,I,L,M,F,P,W,V;
R249N,C,Q,S,T A,I,L,M,F,P,W,Y,V,D,E;
K251N,C,S,T I,L,M,F,P,W,Y,V,D,E;
T252N,C,Q,S;
G253C,Q,S,T;
K254N,C,Q,S,T A,I,L,M,F,P,W,Y,V,D,E;
F257N,C,Q,S,T;
W263N,C,Q,S,T;
L267N,C,Q,S,T;
G268N,C,Q,S,T;
A269N,C,Q,S,T;
K276N,C,Q,S,T A,I,L,M,F,P,W,Y,V,D,E;
Q291N;
H293N,S,T A,I,L,M,P,W,V;
A294N,Q,S,T;
G299S,T;
G300C,T;
G301N,Q,S,T;
R305S,T,I,L,M,F,P,W,Y,V;
K306Q,S,T,I,L,M,F,P,W,Y,V;
L308N,C,Q,S,T;
G310N,C,Q,S,T;
S314C;
K315N,C,Q,S,T A,I,L,M,F,P,W,Y,V,E;
H316N,C,Q,S,T A,I,L,M,F,P,W,V,D,E;
P317N,C,Q,S,T;
L318N,C,Q,S;
K319N,C,Q,S,T A,I,L,M,F,P,W,Y,V,D,E;
G332N,C,Q,S,T;
Q333N;
S334N,C,Q;
L335C,Q;
S337N,C,Q;
T338N,C,Q,S;
T341C;
W342S,T;
P345N,C,Q,T;
E355N,C,Q,S,T;
Y358C;
Y363C;
K370N,C,Q,S,T A,I,L,M,F,P,W,Y,V,D,E;
G371N,C,Q,S,T;
S373N,C,Q,T;
Q374N;
R375N,C,Q,S,T A,I,L,M,F,P,W,V,D;
P378N,C,Q,S,T;
A379N,C,Q,T;
K381N,C,Q,S,T A,I,L,M,F,P,W,Y,V,D,E;
K389C,S,T,A,M,F,P,W,Y,V,D;
Q393N;
Y394C;
Y396C;
A398N,C,Q;
Y402C;
F403N,Q,S,T;
H405I,L,M,F,P,W,Y,V;
H406A,I,M,F,P,Y,V;
I408N,C,Q,S,T;
R413N,C,Q,S,T A,I,L,M,F,P,W,Y,V,D,E;
G415N,C,Q,S,T;
S417N,Q;
S418N,Q;
V419N,C,Q,S,T;
A420N,C,S,T;
S422N,Q;
G431N,Q,S,T;
P432S,T;
G433N,Q,S,T;
G434N,Q,S,T;
A435Q,T;
K436N,C,Q,S,T,A,I,L,M,F,P,W,Y,V,D,E;
R437N,C,Q,S,T,A,I,L,M,F,P,W,Y,V,D,E;
Y439C;
R442N,C,S,T, A,I,L,M,F,P,W,Y,V,D,E;
Q443N;
A445N,C,Q,S,T;
G446N,C,Q,S,T;
T448N,C,Q,S;
H450N,C,Q,S,T,A,I,L,M,F,P,W,V,D,E;
G454N,C,Q,S,T;
R456C,S,T,A,I,L,M,F,P,W,Y,V,D,E;
S457N,C,Q;
P459N,C,Q,S;
V460N,C,Q,S,T;
V461N,C,Q,S;
S464N,C,Q,T;
W467N,C,Q,S,T;
G475N,Q,S,T;
Q482N;
R483N,C,Q,S,T,A,I,L,M,F,P,W,Y,V,D,E.

Increased Stability at Low pH and/or at High Temperature Substitutions Resulting in a More Hydrophobic Amino Acid Residue In an aspect the invention relates to Termamyl-like alpha-amylase variant with increased stability at acidic pH and/or at high temperature in comparison to the parent alpha-amylase. Such variants are especially suitable for starch liquefaction.

In the context of the invention the term "acidic pH" means a pH below 7.0, especially below the pH range, in which industrial starch liquefaction processes are normally performed, which is between pH 5.5 and 6.2.

In the context of the invention "high temperature" is a temperature in the range from 60-110° C.

Such variant are variant having a substitution resulting in a more hydrophobic amino acid residues. Providing such variant of the invention may be prepared by 1) Substituting a charged amino acid residue with a hydrophobic amino acid residue;
2) Substituting a hydrophilic amino acid residue with a hydrophobic amino acid residue;
3) Substituting a hydrophilic amino acid residue with a more hydrophilic amino acid residue;
4) Substituting a hydrophilic amino acid residue with a less hydrophilic amino acid residue.

Thus, variants of the invention include (using SEQ ID NO: 8 for the numbering):
G5A,V,P,M,L,I,Y,F,W;
T6G,A,V,P,M,L,I,Y,F,W;
G36A,V,P,M,L,I,Y,F,W;
I37Y,F,W;
T38G,A,V,P,M,L,I,Y,F,W;
A39V,P,M,L,I,Y,F,W;
I42Y,F,W;
A45V,P,M,L,I,Y,F,W;
K47G,A,I,L,M,F,P,W,Y,V;

D63G,A,V,P,M,L,I,Y,F,W;
E66G,A,V,P,M,L,I,Y,F,W;
Q69T,S,C, G,A,V,P,M,L,I,Y,F,W;
K70G,A,V,P,M,L,I,Y,F,W;
G71A,V,P,M,L,I,Y,F,W;
T72G,A,V,P,M,L,I,Y,F,W;
R74G,A,V,P,M,L,I,Y,F,W;
T75G,A,V,P,M,L,I,Y,F,W;
K76G,A,V,P,M,L,I,Y,F,W;
T79G,A,V,P,M,L,I,Y,F,W;
E82G,A,V,P,M,L,I,Y,F,W;
L83I,Y,F,W;
A86V,P,M,L,I,Y,F,W;
I87Y,F,W;
S89G,A,V,P,M,L,I,Y,F,W;
R93G,A,V,P,M,L,I,Y,F,W;
T112G,A,V,P,M,L,I,Y,F,W;
E113G,A,V,P,M,L,I,Y,F,W;
A117,V,P,M,L,I,Y,F,W;
V120P,M,L,I,Y,F,W;
A137V,P,M,L,I,Y,F,W;
K213G,A,V,P,M,L,I,Y,F,W;
G216A,V,P,M,L,I,Y,F,W;
A220V,P,M,L,I,Y,F,W;
L223I,Y,F,W;
L225I,Y,F,W;
D226G,A,V,P,M,L,I,Y,F,W;
G227G,A,V,P,M,L,I,Y,F,W;
R229G,A,V,P,M,L,I,Y,F,W;
D243G,A,V,P,M,L,I,Y,F,W;
V245P,M,L,I,Y,F,W;
F279W;
S282T,G,A,V,P,M,L,I,Y,F,W;
T311G,A,V,P,M,L,I,Y,F,W;
V321P,M,L,I,Y,F,W;
V324P,M,L,I,Y,F,W;
L352I,Y,F,W;
T353G,A,V,P,M,L,I,Y,F,W;
R354G,A,V,P,M,L,I,Y,F,W;
G357A,V,P,M,L,I,Y,F,W;
V361P,M,L,I,Y,F,W;
F362W;
G364A,V,P,M,L,I,Y,F,W;
G368A,V,P,M,L,I,Y,F,W;
A390V,P,M,L,I,Y,F,W;
A395V,P,M,L,I,Y,F,W;
G397A,V,P,M,L,I,Y,F,W;
Q399T,S,C,G,A,V,P,M,L,I,Y,F,W;
H400G,A,V,P,M,L,I,Y,F,W;
D401G,A,V,P,M,L,I,Y,F,W;
A425V,P,M,L,I,Y,F,W;
D451G,A,V,P,M,L,I,Y,F,W;
I452Y,F,W;
T453G,A,V,P,M,L,I,Y,F,W;
G466G,A,V,P,M,L,I,Y,F,W;
G468A,V,P,M,L,I,Y,F,W;
F470W;
H471G,A,V,P,M,L,I,Y,F,W;
S478T,G,A,V,P,M,L,I,Y,F,W
Q9A,C,G,M,P,S,T,W,Y,V;
F11W;
E12A,G,I,L,M,F,P,W,Y,V;
G19A,I,L,M,F,P,W,Y,V;
H21A,G,I,L,M,F,P,W,Y,V;
L25I,W,Y;
L32I,F,W,Y;
V40I,L,M,F,P,W,Y;
Y46W;
G48M,F,P,W,Y;
G55AI,L,M,F,P,W,Y,V;
G57M,P,W;
A58G,M,W,Y;
D60AG,I,L,M,F,PW,Y,V;
Y77W;
I95F,W,Y;
V97I,L,M,F,P,W,Y;
Y98W;
G99I,L,M,F,P,W,Y,V;
D100A,G,I,M,F,P,W,Y,V;
V101I,L,M,P,W,Y;
V102I,L,M,F,P,W,Y;
I103W;
H105A,G,I,L,M,P,Y,V;
G107M,F,P,W,Y;
V115I,L,M,F,P,W,Y;
V118I,L,M,F,P,W,Y;
I135F,W,Y;
T139AG,I,L,M,F,P,W,Y,V;
F141W;
S151A,G,M,P,T,Y,V;
H159A,G,I,L,M,F,P,W,V;
F160W;
D161A,G,I,L,M,F,P,W,Y,V;
G162A,I,L,M,F,P,W,Y,V;
T163A,G,I,L,M,F,P,Y,V;
D166A,G,I,L,M,F,P,W,Y,V;
Y175W;
F177W;
D183A,G,I,L,M,F,P,W,Y,V;
V186I,L,M,F,P,W,Y;
S187A,G,I,L,M,F,P,W,Y,V;
N192A,G,I,L,M,F,P,W,Y,V;
A199G,I,L,M,F,P,W,Y,V;
D200AG,I,L,M,F,P,W,Y,V;
D202A,G,I,L,M,F,P,W,Y,V;
V208L,M,F,P,W,Y;
Y219W;
F228W;
L230W,Y;
V233G,I,M,P,W,Y;
I236M,P;
F238W;
F240W;
L241P;
V248A,G,I,L,M,F,P,W,Y;
T258A,G,I,M,F,P,W,Y,V;
V259M,P,W,Y;
A260I,L,M,F,P,W,Y,V;
Y262W;
L270I,F,W,Y;
L274I,M,F,P,W,Y;
T277A,G,M,P,W,Y,V;
H281A,G,M,P,W,Y,V;
V283I,L,M,F,P,W,Y;
D285A,G,I,M,F,P,W,Y,V;
V286I,M,F,P,W,Y;
P287I,L,M,F,W,Y;
L288I,F,W,Y;
H289A,G,I,L,M,F,P,W,Y,V;
F292W;
A295I,L,M,F,P,W,Y,V;
S296A,G,I,L,M,F,P,W,T,Y,V;
L307I,F,W,Y;
V312I,L,M,F,P,W,Y;

V313I,L,M,F,P,W,Y;
S320G,I,L,M,F,P,T,W,Y,V;
T322G,L,M,F,P,W,Y,V;
F323W;
D325A,G,I,L,M,F,P,W,Y,V;
N326A,C,G,M,P,S,T,W;
H327A,G,I,L,M,P,W,Y,V;
T329A,G,I,L,M,F,P,W,Y,V;
P331I,L,M,F,W,Y;
V339I,L,M,F,P,W,Y;
K344A,G,I,L,M,F,P,W,Y,V;
L346I,F,W,Y;
A347I,L,M,F,P,W,Y,V;
A349I,L,M,F,P,W,Y,V;
P359I,L,M,F,W,Y;
Q360I,L,M,F,P,S,T,W,Y,V;
T369A,G,I,L,M,F,P,W,Y,V;
I377F,W,Y;
L380W,Y;
I387W,Y;
V409M,P,W,Y;
G410A,I,L,M,F,P,W,Y,V;
T412G,I,L,M,F,P,W,Y,V;
G423A,I,L,M,F,P,W,Y,V;
L424I,F,W,Y;
A426I,L,M,F,P,W,Y,V;
L427Y;
I428F,W,Y;
T429A,G,I,L,M,F,P,W,Y,V;
D430A,G,I,L,M,F,P,W,Y,V;
V440I,L,M,F,P,W,Y;
G441A,I,L,M,F,P,W,Y,V;
I462F,W,Y;
V472I,L,M,F,P,W,Y;
V477I,L,M,F,P,W,Y;
I479F,W,Y;
Y480W;
V481M,P,Y
A1I,L,M,F,P,W,Y;
N2C,Q,I,L,M,F,S,T,W,Y,V;
L3I,M,F,P,W,Y;
N4A,C,Q,I,L,M,F,P,S,T,W,Y,V;
Y14W;
P16I,L,M,F,W,Y;
N17A,C,Q,G,I,L,M,F,P,S,T,W,Y,V;
D18A,G,I,L,M,F,P,W,Y,V;
Q20A,C,I,L,M,F,P,S,T,W,Y,V;
R23A,G,I,L,M,F,P,W,Y,V;
R24A,G,I,L,M,F,P,W,Y,V;
Q26A,C,G,I,L,M,F,P,S,T,W,V;
E34A,G,I,L,M,F,P,W,Y,V;
H35A,G,M,F,P,W,Y,V;
T49A,G,P;
S50A,G,M,F,P,W;
Q51A,C,G,I,L,M,F,P,S,T,W,Y,V;
A52P;
D53A,G,M,P;
L61I,M,Y;
H68A,G,I,L,M,F,P,W,Y,V;
V73M,P,W,Y;
Q84A,C,G,I,L,M,F,P,S,T,W,Y,V;
S85A,G,I,L,M,F,P,T,W,Y,V;
K88A,G,I,L,M,F,P,W,Y,V;
H91A,G,I,L,M,F,P,W,Y,V;
S92A,G,I,L,M,F,P,T,W,Y,V;
N96A,C,G,I,L,M,F,P,S,T,W,Y,V;
K106A,G,I,L,M,P,Y,V;
G108I,L,M,F,P,W,Y,V;
D114A,G,F,P,W,Y;
T116A,G,I,L,M,F,P,W,Y,V;
E119A,G,I,L,M,F,P,W,Y,V;
D121A,G,I,L,M,F,P,W,Y,V;
P122I,L,M,F,W,Y;
A123I,L,M,F,P,W,Y,V;
D124G,I,L,M,F,P,W,Y,V;
R125G,I,M,F,W,Y;
N126Q,G,I,L,M,F,P,S,T,W,Y,V;
R127A,G,I,L,M,F,P,W,Y,V;
V128I,L,M,F,P,W,Y;
I129F,W,Y;
S130A,G,I,L,M,F,P,W,Y,V;
G131A,I,L,M,F,P,W,Y,V;
E132G,I,L,M,F,W,Y;
H133M,W,V;
L134I,F,W,Y;
K136A,G,I,L,M,F,P,W,Y,V;
G145A,I,L,M,P,Y,V;
G147A,I,L,M,P,W,Y,V;
S148A,G,I,L,M,F,P,T,W,Y,V;
T149A,G,L,M,F,P,V,Y,V;
Y150W;
D152A,G,I,L,M,F,P,W,Y,V;
F153W;
K154A,G,I,L,M,F,P,W,Y,V;
H156A,G,I,L,M,F,P,W,V;
Y158W;
D164I,L,M,F,P,W,Y,V;
E167A,G,I,L,M,F,P,W,Y,V;
S168A,G,I,L,M,F,T,W,V;
R169A,G,M,P,W,Y,V;
K170A,G,I,L,M,F,P,W,Y,V;
L171W,Y;
N172A,C,Q,G,I,L,M,F,P,T,W,Y,V;
R173A,G,M,P,W,Y,V;
K176A,G,I,L,M,F,P,W,Y,V;
G179I,L,M,F,P,W,Y,V;
K180A,G,I,L,M,F,P,W,Y,V;
E185I,L,M,F,P,W,Y,V;
N188A,Q,G,L,M,F,W,V;
E189A,G,I,L,M,F,P,W,Y,V;
G191A,I,L,M,F,P,W,Y,V;
Y193W;
L196I,W;
Y198W;
D204L,M,F,P,W,Y,V;
H205A,G,I,L,M,F,P,W,Y,V;
P206G,I,L,M,F,W,Y,V;
A209P,W,Y;
A210G,I,L,M,F,P,W,Y,V;
R214A,G,I,L,M,F,P,Y,V;
T217A,G,I,L,M,F,P,W,Y;
N221A,C,Q,G,I,L,M,F,P,S,T,W,Y,V;
E222A,G,I,L,M,F,P,W,Y,V;
K234A,G,I,M,F,P,W,Y,V;
H235A,G,I,L,M,F,P,W,Y,V;
K237A,G,I,L,M,F,W,Y,V;
S239G,I,L,M,F,P,T,Y,V;
R242G,I,L,M,F,W,Y,V;
N246A,C,Q,G,I,L,M,F,P,S,T,W,Y,V;
H247G,I,L,M,F,P,W,V;
R249A,G,I,L,M,F,P,W,Y,V;
E250A,I,L,M,P,W,Y,V;
K251G,I,L,M,F,P,W,Y,V;
T252A,G,I,L,M,F,P,W,Y,V;

G253I,L,M,F,P,W,Y;
K254A,G,I,L,M,F,P,W,Y,V;
E255A,G,I,L,M,F,W,Y,V;
F257W;
E261A,G,I,L,M,F,P,W,Y,V;
N265C,Q,I,L,M,F,P,W;
D266A,G,I,L,M,F,P,W,Y,V;
L267W,Y;
G268A,I,L,M,F,P,W,Y,V;
A269I,L,M,F,P,W,Y,V;
E271A,G,I,L,M,F,P,W,Y,V;
N272A,C,Q,G,I,L,M,F,P,S,T,W,Y,V;
N275A,C,Q,G,I,L,M,F,P,S,W,Y,V;
K276A,G,I,L,M,F,P,W,Y,V;
N278A,C,Q,G,H,I,L,M,F,P,S,T,W,Y,V;
N280A,C,G,I,L,M,F,P,W,Y,V;
Y290W;
Q291A,G,I,L,M,F,P,S,T,W,Y,V;
H293A,G,I,L,M,P,W,V;
A294I,L,M,F,P,W,Y;
T297A,G,I,L,M,F,P,W,Y,V;
Q298G,I,L,M,F,P,S,T,W,Y,V;
G299A,M,P;
G300A,I,L,M,F,P,W,Y,V;
G301I,L,M,F,P,W,Y,V;
Y302W;
D303I,L,M,F,P,W,Y,V;
R305G,I,L,M,F,P,W,Y,V;
K306G,I,L,M,F,P,W,Y,V;
L308I,F,W,Y;
N309Q,G,I,L,M,F,P,S,T,W,Y,V;
G310A,I,L,M,F,P,W,Y,V;
S314A,G,I,L,M,F,P,W,Y,V;
K315A,G,I,L,M,F,P,W,Y,V;
H316A,G,I,L,M,F,P,W,V;
P317I,L,M,F,W,Y;
L318I,W,Y;
K319A,G,I,L,M,F,P,W,Y,V;
D328A,G,I,L,M,F,P,W,Y,V;
G332A,I,L,M,F,P,W,Y,V;
Q333A,C,G,I,M,F,P,S,T,Y,V;
S334G,M,F,P,W,Y;
L335I,F,W,Y;
E336A,G,I,L,M,F,P,W,Y,V;
S337A,G,I,L,M,F,P,T,W,Y,V;
T338A,G,I,L,M,F,P,W,Y,V;
Q340I,L,M,F,P,S,T,W,Y,V;
T341A,G,I,L,M,F,W,Y,V;
P345I,L,M,F,W,Y;
E355A,G,I,L,M,F,P,W,Y,V;
Y358W;
Y363W;
K370A,G,I,L,M,F,P,W,Y,V;
G371A,I,L,M,F,P,W,Y,V;
S373A,G,I,L,M,F,T,W,Y,V;
Q374A,C,G,I,L,M,F,S,T,W,Y,V;
R375A,G,I,L,M,F,P,W,V;
E376A,G,I,L,M,F,P,W,Y,V;
P378G,I,L,M,F,W,Y,V;
A379I,L,M,F,P,W,Y,V;
K381A,G,I,L,M,F,P,W,Y,V;
K389A,G,M,F,P,W,Y,V;
Q393A,C,G,I,L,M,F,P,S,T,W,Y,V;
Y394W;
Y396W;
A398I,L,M,F,W,Y,V;
Y402W;
F403W;
D404I,L,M,F,P,W,Y,V;
H405G,I,L,M,F,P,W,Y,V;
H406A,G,I,M,F,P,Y,V;
D407A,G,I,L,M,F,P,W,Y,V;
I408W,Y;
R413A,G,I,L,M,F,P,W,Y,V;
E414A,G,I,L,M,F,P,W,Y,V;
G415A,I,L,M,F,P,W,Y,V;
D416A,G,I,L,M,F,P,W,Y,V;
S417A,G,I,L,M,F,P,W,Y,V;
S418A,G,I,L,M,F,P,T,W,Y,V;
V419I,L,M,F,P,W,Y;
A420I,L,M,F,W,Y,V;
N421A,C,Q,I,L,M,F,P,S,T,W,Y,V;
S422A,G,I,L,M,F,P,T,W,Y,V;
G431A,I,L,M,F,P,W,Y,V;
P432I,L,M,F,W,Y;
G433A,I,L,M,F,P,W,Y,V;
G434A,I,L,M,F,P,W,Y,V;
A435I,L,M,F,P,W,Y,V;
K436A,G,I,L,M,F,P,W,Y,V;
R437A,G,I,L,M,F,P,W,Y,V;
Y439W;
R442A,G,I,L,M,F,P,W,Y,V;
Q443A,C,G,I,L,M,F,P,S,T,W,Y,V;
N444A,C,G,I,L,M,F,P,S,T,W,Y,V;
A445I,L,M,F,P,W,Y,V;
G446A,I,L,M,F,P,W,Y,V;
E447A,G,I,L,M,F,P,W,Y,V;
T448A,G,I,L,M,F,P,W,Y,V;
H450A,G,I,L,M,F,P,W,V;
G454A,I,L,M,F,P,W,Y,V;
N455A,C,Q,G,I,L,M,F,P,S,T,W,Y,V;
R456A,I,L,M,F,P,W,Y,V;
S457A,G,I,L,M,F,W,Y,V;
E458A,G,I,L,M,F,P,W,Y,V;
P459I,L,M,F,W,Y;
V460I,L,M,F,P,W,Y;
V461I,L,M,F,P,W,Y;
N463A,C,Q,I,L,M,F,P,S,T,W,Y,V;
S464A,G,I,L,M,F,P,T,W,Y,V;
E465A,G,I,L,M,F,P,W,Y,V;
E469A,G,I,L,M,F,P,W,Y,V;
N473Q,G,I,L,M,F,P,S,T,W,Y,V;
G474A,I,L,M,F,P,W,Y,V;
G475A,I,L,M,F,P,W,Y,V;
S476G,I,L,M,F,P,T,W,Y,V;
Q482A,C,G,I,L,M,F,S,T,W,Y,V;
R483A,G,I,L,M,F,P,W,Y,V.

General Mutations in Variants of the Invention

A variant of the invention may in one embodiment comprise one or more modifications in addition to those outlined above. Thus, it may be advantageous that one or more Proline (Pro) residues present in the part of the alpha-amylase variant which is modified is/are replaced with a non-Proline residue which may be any of the possible, naturally occurring non-Proline residues, and which preferably is an Alanine, Glycine, Serine, Threonine, Valine or Leucine.

Analogously, in one embodiment one or more Cysteine residues present in the parent alpha-amylase may be replaced with a non-Cysteine residue such as Serine, Alanine, Threonine, Glycine, Valine or Leucine.

Furthermore, a variant of the invention may—either as the only modification or in combination with any of the above outlined modifications—be modified so that one or more Asp and/or Glu present in an amino acid fragment corresponding to the amino acid fragment 185-209 of SEQ ID NO: 10 is replaced by an Asn and/or Gln, respectively. Also of interest is the replacement, in the Termamyl-like alpha-amylase, of one or more of the Lys residues present in an amino acid fragment corresponding to the amino acid fragment 185-209 of SEQ ID NO: 10 by an Arg.

It is to be understood that the present invention encompasses variants incorporating two or more of the above outlined modifications.

Furthermore, it may be advantageous to introduce mutations in one or more of the following positions (using SEQ ID NO: 8 (Termamyl) for the numbering):
M15, V128, A111, H133, W138, T149, M197, N188, A209, A210, H405, T412, in particular the following single, double or triple or multi mutations:
M15X, in particular M15T,L;
V128X, in particular V128E;
H133X, in particular H133Y;
N188X, in particular N188S,T,P;
M197X, in particular M197T,L;
A209X, in particular A209V;
M197T/W138F; M197T/W138Y; M15T/H133Y/N188S; M15N128E/H133Y/N188S; E119C/S130C; D124C/R127C; H133Y/T149I;
G475R, H133Y/S187D; H133Y/A209V.

Methods for Preparing Alpha-Amylase Variants of the Invention

Several methods for introducing mutations into genes are known in the art. After a brief description of cloning of alpha-amylase-encoding DNA sequences, methods for generating mutations at specific sites within the alpha-amylase-encoding sequence will be described.

Cloning a DNA Sequence Encoding an Alpha-Amylase

The DNA sequence encoding a parent alpha-amylase may be isolated from any cell or microorganism producing the alpha-amylase in question, using various methods well known in the art. First, a genomic DNA and/or cDNA library should be constructed using chromosomal DNA or messenger RNA from the organism that produces the alpha-amylase to be studied. Then, if the amino acid sequence of the alpha-amylase is known, homologous, labeled oligonucleotide probes may be synthesized and used to identify alpha-amylase-encoding clones from a genomic library prepared from the organism in question. Alternatively, a labeled oligonucleotide probe containing sequences homologous to a known alpha-amylase gene could be used as a probe to identify alpha-amylase-encoding clones, using hybridization and washing conditions of lower stringency.

Yet another method for identifying alpha-amylase-encoding clones would involve inserting fragments of genomic DNA into an expression vector, such as a plasmid, transforming alpha-amylase-negative bacteria with the resulting genomic DNA library, and then plating the transformed bacteria onto agar containing a substrate for alpha-amylase, thereby allowing clones expressing the alpha-amylase to be identified.

Alternatively, the DNA sequence encoding the enzyme may be prepared synthetically by established standard methods, e.g., the phosphoroamidite method described by S. L. Beaucage and M. H. Caruthers, *Tetrahedron Letters* 22, 1981, pp. 1859-1869, or the method described by Matthes et al., *The EMBO J.* 3, 1984, pp. 801-805. In the phosphoroamidite method, oligonucleotides are synthesized, e.g., in an automatic DNA synthesizer, purified, annealed, ligated and cloned in appropriate vectors.

Finally, the DNA sequence may be of mixed genomic and synthetic origin, mixed synthetic and cDNA origin or mixed genomic and cDNA origin, prepared by ligating fragments of synthetic, genomic or cDNA origin (as appropriate, the fragments corresponding to various parts of the entire DNA sequence), in accordance with standard techniques. The DNA sequence may also be prepared by polymerase chain reaction (PCR) using specific primers, for instance as described in U.S. Pat. No. 4,683,202 or R. K. Saiki et al., *Science* 239, 1988, pp. 487-491.

Site-Directed Mutagenesis

Once an alpha-amylase-encoding DNA sequence has been isolated, and desirable sites for mutation identified, mutations may be introduced using synthetic oligonucleotides. These oligonucleotides contain nucleotide sequences flanking the desired mutation sites; mutant nucleotides are inserted during oligonucleotide synthesis. In a specific method, a single-stranded gap of DNA, bridging the alpha-amylase-encoding sequence, is created in a vector carrying the alpha-amylase gene. Then the synthetic nucleotide, bearing the desired mutation, is annealed to a homologous portion of the single-stranded DNA. The remaining gap is then filled in with DNA polymerase I (Klenow fragment) and the construct is ligated using T4 ligase. A specific example of this method is described in Morinaga et al. (1984). U.S. Pat. No. 4,760,025 disclose the introduction of oligonucleotides encoding multiple mutations by performing minor alterations of the cassette. However, an even greater variety of mutations can be introduced at any one time by the Morinaga method, because a multitude of oligonucleotides, of various lengths, can be introduced.

Another method for introducing mutations into alpha-amylase-encoding DNA sequences is described in Nelson and Long (1989). It involves the 3-step generation of a PCR fragment containing the desired mutation introduced by using a chemically synthesized DNA strand as one of the primers in the PCR reactions. From the PCR-generated fragment, a DNA fragment carrying the mutation may be isolated by cleavage with restriction endonucleases and reinserted into an expression plasmid.

Alternative methods for providing variants of the invention include gene shuffling, e.g., as described in WO 95/22625 (from Affymax Technologies N.V.) or in WO 96/00343 (from Novo Nordisk A/S), or other corresponding techniques resulting in a hybrid enzyme comprising the mutation(s), e.g., substitution(s) and/or deletion(s), in question.

Expression of Alpha-Amylase Variants

According to the invention, a DNA sequence encoding the variant produced by methods described above, or by any alternative methods known in the art, can be expressed, in enzyme form, using an expression vector which typically includes control sequences encoding a promoter, operator, ribosome binding site, translation initiation signal, and, optionally, a repressor gene or various activator genes.

The recombinant expression vector carrying the DNA sequence encoding an alpha-amylase variant of the invention may be any vector, which may conveniently be subjected to recombinant DNA procedures, and the choice of vector will often depend on the host cell into which it is to be introduced. Thus, the vector may be an autonomously replicating vector, i.e., a vector which exists as an extrachromosomal entity, the replication of which is independent of chromosomal replication, e.g., a plasmid, a bacteriophage or an extrachromosomal element, minichromosome or an artificial chromosome. Alternatively, the vector may be one which, when introduced into a host cell, is integrated into the host cell genome and replicated together with the chromosome(s) into which it has been integrated.

In the vector, the DNA sequence should be operably connected to a suitable promoter sequence. The promoter may be any DNA sequence, which shows transcriptional activity in the host cell of choice and may be derived from genes encoding proteins either homologous or heterologous to the host cell. Examples of suitable promoters for directing the transcription of the DNA sequence encoding an alpha-amylase variant of the invention, especially in a bacterial host, are the promoter of the lac operon of *E. coli*, the *Streptomyces coelicolor* agarase gene dagA promoters, the promoters of the *Bacillus licheniformis* alpha-amylase gene (amyL), the promoters of the *Bacillus stearothermophilus* maltogenic amylase gene (amyM), the promoters of the *Bacillus amyloliquefaciens* alpha-amylase (amyQ), the promoters of the *Bacillus subtilis* xylA and xylB genes etc. For transcription in a fungal host, examples of useful promoters are those derived from the gene encoding *A. oryzae* TAKA amylase, *Rhizomucor miehei* aspartic proteinase, *A. niger* neutral alpha-amylase, *A. niger* acid stable alpha-amylase, *A. niger* glucoamylase, *Rhizomucor miehei* lipase, *A. oryzae* alkaline protease, *A. oryzae* triose phosphate isomerase or *A. nidulans* acetamidase.

The expression vector of the invention may also comprise a suitable transcription terminator and, in eukaryotes, polyadenylation sequences operably connected to the DNA sequence encoding the alpha-amylase variant of the invention. Termination and polyadenylation sequences may suitably be derived from the same sources as the promoter.

The vector may further comprise a DNA sequence enabling the vector to replicate in the host cell in question. Examples of such sequences are the origins of replication of plasmids pUC19, pACYC177, pUB110, pE194, pAMB1 and pIJ702.

The vector may also comprise a selectable marker, e.g. a gene the product of which complements a defect in the host cell, such as the dal genes from *B. subtilis* or *B. licheniformis*, or one which confers antibiotic resistance such as ampicillin, kanamycin, chloramphenicol or tetracyclin resistance. Furthermore, the vector may comprise *Aspergillus* selection markers such as amdS, argB, niaD and sC, a marker giving rise to hygromycin resistance, or the selection may be accomplished by co-transformation, e.g., as described in WO 91/17243.

While intracellular expression may be advantageous in some respects, e.g., when using certain bacteria as host cells, it is generally preferred that the expression is extracellular. In general, the *Bacillus* alpha-amylases mentioned herein comprise a preregion permitting secretion of the expressed protease into the culture medium. If desirable, this preregion may be replaced by a different preregion or signal sequence, conveniently accomplished by substitution of the DNA sequences encoding the respective preregions.

The procedures used to ligate the DNA construct of the invention encoding an alpha-amylase variant, the promoter, terminator and other elements, respectively, and to insert them into suitable vectors containing the information necessary for replication, are well known to persons skilled in the art (cf., for instance, Sambrook et al., *Molecular Cloning: A Laboratory Manual,* 2nd Ed., Cold Spring Harbor, 1989).

The cell of the invention, either comprising a DNA construct or an expression vector of the invention as defined above, is advantageously used as a host cell in the recombinant production of an alpha-amylase variant of the invention. The cell may be transformed with the DNA construct of the invention encoding the variant, conveniently by integrating the DNA construct (in one or more copies) in the host chromosome. This integration is generally considered to be an ad-vantage as the DNA sequence is more likely to be stably maintained in the cell. Integration of the DNA constructs into the host chromosome may be performed according to conventional methods, e.g., by homologous or heterologous recombination. Alternatively, the cell may be transformed with an expression vector as described above in connection with the different types of host cells.

The cell of the invention may be a cell of a higher organism such as a mammal or an insect, but is preferably a microbial cell, e.g., a bacterial or a fungal (including yeast) cell.

Examples of suitable bacteria are Gram-positive bacteria such as *Bacillus subtilis*, *Bacillus licheniformis*, *Bacillus lentus*, *Bacillus brevis*, *Bacillus stearothermophilus*, *Bacillus alkalophilus*, *Bacillus amyloliquefaciens*, *Bacillus coagulans*, *Bacillus circulans*, *Bacillus lautus*, *Bacillus megaterium*, *Bacillus thuringiensis*, or *Streptomyces lividans* or *Streptomyces murinus*, or gram-negative bacteria such as *E. coli*. The transformation of the bacteria may, for instance, be effected by protoplast transformation or by using competent cells in a manner known per se.

The yeast organism may favorably be selected from a species of *Saccharomyces* or *Schizosaccharomyces*, e.g. *Saccharomyces cerevisiae*. The filamentous fungus may advantageously belong to a species of *Aspergillus*, e.g., *Aspergillus oryzae* or *Aspergillus niger*. Fungal cells may be transformed by a process involving protoplast formation and transformation of the protoplasts followed by regeneration of the cell wall in a manner known per se. A suitable procedure for transformation of *Aspergillus* host cells is described in EP 238 023.

In a yet further aspect, the present invention relates to a method of producing an alpha-amylase variant of the invention, which method comprises cultivating a host cell as described above under conditions conducive to the production of the variant and recovering the variant from the cells and/or culture medium.

The medium used to cultivate the cells may be any conventional medium suitable for growing the host cell in question and obtaining expression of the alpha-amylase variant of the invention. Suitable media are available from commercial suppliers or may be prepared according to published recipes (e.g., as described in catalogues of the American Type Culture Collection).

The alpha-amylase variant secreted from the host cells may conveniently be recovered from the culture medium by well-known procedures, including separating the cells from the medium by centrifugation or filtration, and precipitating proteinaceous components of the medium by means of a salt such as ammonium sulphate, followed by the use of chromatographic procedures such as ion exchange chromatography, affinity chromatography, or the like.

Industrial Applications

The alpha-amylase variants of this invention possess valuable properties allowing for a variety of industrial applications. In particular, enzyme variants of the invention are applicable as a component in washing, dishwashing, and hard surface cleaning detergent compositions.

Variant of the invention with altered properties may be used for starch processes, in particular starch conversion, especially liquefaction of starch (see, e.g., U.S. Pat. No. 3,912,590, EP patent application nos. 252 730 and 63 909, WO 99/19467, and WO 96/28567 all references hereby incorporated by reference). Also contemplated are compositions for starch conversion purposes, which may beside the variant of the invention also comprise a glucoamylase, pullulanase, and other alpha-amylases.

Further, variants of the invention are also particularly useful in the production of sweeteners and ethanol (see, e.g., U.S.

Pat. No. 5,231,017 hereby incorporated by reference), such as fuel, drinking and industrial ethanol, from starch or whole grains.

Variants of the invention may also be useful for desizing of textiles, fabrics and garments (see, e.g., WO 95/21247, U.S. Pat. No. 4,643,736, EP 119,920 hereby in corporate by reference), beer making or brewing, in pulp and paper production.

Starch Conversion

Conventional starch-conversion processes, such as liquefaction and saccharification processes are described, e.g., in U.S. Pat. No. 3,912,590 and EP patent publications Nos. 252,730 and 63,909, hereby incorporated by reference.

In an embodiment the starch conversion process degrading starch to lower molecular weight carbohydrate components such as sugars or fat replacers includes a debranching step.

Starch to Sugar Conversion

In the case of converting starch into a sugar the starch is depolymerized. A such depolymerization process consists of a Pre-treatment step and two or three consecutive process steps, viz. a liquefaction process, a saccharification process and dependent on the desired end product optionally an isomerization process.

Pre-Treatment of Native Starch

Native starch consists of microscopic granules, which are insoluble in water at room temperature. When an aqueous starch slurry is heated, the granules swell and eventually burst, dispersing the starch molecules into the solution. During this "gelatinization" process there is a dramatic increase in viscosity. As the solids level is 30-40% in a typically industrial process, the starch has to be thinned or "liquefied" so that it can be handled. This reduction in viscosity is today mostly obtained by enzymatic degradation.

Liquefaction

During the liquefaction step, the long chained starch is degraded into branched and linear shorter units (maltodextrins) by an alpha-amylase. The liquefaction process is carried out at 105-110° C. for 5 to 10 minutes followed by 1-2 hours at 95° C. The pH lies between 5.5 and 6.2. In order to ensure optimal enzyme stability under these conditions, 1 mM of calcium is added (40 ppm free calcium ions). After this treatment the liquefied starch will have a "dextrose equivalent" (DE) of 10-15.

Saccharification

After the liquefaction process the maltodextrins are converted into dextrose by addition of a glucoamylase (e.g., AMG) and a debranching enzyme, such as an isoamylase (U.S. Pat. No. 4,335,208) or a pullulanase (e.g., Promozyme™) (U.S. Pat. No. 4,560,651). Before this step the pH is reduced to a value below 4.5, maintaining the high temperature (above 95° C.) to inactivate the liquefying alpha-amylase to reduce the formation of short oligosaccharide called "panose precursors" which cannot be hydrolyzed properly by the debranching enzyme.

The temperature is lowered to 60° C., and glucoamylase and debranching enzyme are added. The saccharification process proceeds for 24-72 hours.

Normally, when denaturing the α-amylase after the liquefaction step about 0.2-0.5% of the saccharification product is the branched trisaccharide $6^2$-alpha-glucosyl maltose (panose) which cannot be degraded by a pullulanase. If active amylase from the liquefaction step is present during saccharification (i.e., no denaturing), this level can be as high as 1-2%, which is highly undesirable as it lowers the saccharification yield significantly.

Isomerization

When the desired final sugar product is, e.g., high fructose syrup the dextrose syrup may be converted into fructose. After the saccharification process the pH is increased to a value in the range of 6-8, preferably pH 7.5, and the calcium is removed by ion exchange. The dextrose syrup is then converted into high fructose syrup using, e.g., an immobilized glucoseisomerase (such as Sweetzyme™ IT).

Ethanol Production

In general alcohol production (ethanol) from whole grain can be separated into 4 main steps Milling
Liquefaction
Saccharification
Fermentation Milling The grain is milled in order to open up the structure and allowing for further processing. Two processes are used wet or dry milling. In dry milling the whole kernel is milled and used in the remaining part of the process. Wet milling gives a very good separation of germ and meal (starch granules and protein) and is with a few exceptions applied at locations where there is a parallel production of syrups.

Liquefaction

In the liquefaction process the starch granules are solubilized by hydrolysis to maltodextrins mostly of a DP higher than 4. The hydrolysis may be carried out by acid treatment or enzymatically by alpha-amylase. Acid hydrolysis is used on a limited basis. The raw material can be milled whole grain or a side stream from starch processing.

Enzymatic liquefaction is typically carried out as a three-step hot slurry process. The slurry is heated to between 60-95° C., preferably 80-85° C., and the enzyme(s) is (are) added. Then the slurry is jet-cooked at between 95-140° C., preferably 105-125° C., cooled to 60-95° C. and more enzyme(s) is (are) added to obtain the final hydrolysis. The liquefaction process is carried out at pH 4.5-6.5, typically at a pH between 5 and 6. Milled and liquefied grain is also known as mash.

Saccharification

To produce low molecular sugars $DP_{1-3}$ that can be metabolized by yeast, the maltodextrin from the liquefaction must be further hydrolyzed. The hydrolysis is typically done enzymatically by glucoamylases, alternatively alpha-glucosidases or acid alpha-amylases can be used. A full saccharification step may last up to 72 hours, however, it is common only to do a pre-saccharification of typically 40-90 minutes and then complete saccharification during fermentation (SSF). Saccharification is typically carried out at temperatures from 30-65 C, typically around 60 C, and at pH 4.5.

Fermentation

Yeast typically from *Saccharomyces* spp. is added to the mash and the fermentation is ongoing for 24-96 hours, such as typically 35-60 hours. The temperature is between 26-34° C., typically at about 32° C., and the pH is from pH 3-6, preferably around pH 4-5.

Note that the most widely used process is a simultaneous saccharification and fermentation (SSF) process where there is no holding stage for the saccharification, meaning that yeast and enzyme is added together. When doing SSF it is common to introduce a pre-saccharification step at a temperature above 50° C., just prior to the fermentation.

Distillation

Following the fermentation the mash is distilled to extract the ethanol.

The ethanol obtained according to the process of the invention may be used as, e.g., fuel ethanol; drinking ethanol, i.e., potable neutral spirits; or industrial ethanol.

By-Products

Left over from the fermentation is the grain, which is typically used for animal feed either in liquid form or dried.

Further details on how to carry out liquefaction, saccharification, fermentation, distillation, and recovering of ethanol are well known to the skilled person.

According to the process of the invention the saccharification and fermentation may be carried out simultaneously or separately.

Pulp and Paper Production

The alkaline alpha-amylase of the invention may also be used in the production of lignocellulosic materials, such as pulp, paper and cardboard, from starch reinforced waste paper and cardboard, especially where re-pulping occurs at pH above 7 and where amylases facilitate the disintegration of the waste material through degradation of the reinforcing starch. The alpha-amylase of the invention is especially useful in a process for producing a papermaking pulp from starch-coated printed-paper. The process may be performed as described in WO 95/14807, comprising the following steps:

a) disintegrating the paper to produce a pulp, b) treating with a starch-degrading enzyme before, during or after step a), and c) separating ink particles from the pulp after steps a) and b).

The alpha-amylases of the invention may also be very useful in modifying starch where enzymatically modified starch is used in papermaking together with alkaline fillers such as calcium carbonate, kaolin and clays. With the alkaline alpha-amylases of the invention it becomes possible to modify the starch in the presence of the filler thus allowing for a simpler integrated process.

Desizing of Textiles, Fabrics and Garments

An alpha-amylase of the invention may also be very useful in textile, fabric or garment desizing. In the textile processing industry, alpha-amylases are traditionally used as auxiliaries in the desizing process to facilitate the removal of starch-containing size, which has served as a protective coating on weft yarns during weaving. Complete removal of the size coating after weaving is important to ensure optimum results in the subsequent processes, in which the fabric is scoured, bleached and dyed. Enzymatic starch breakdown is preferred because it does not involve any harmful effect on the fiber material. In order to reduce processing cost and increase mill throughput, the desizing processing is sometimes combined with the scouring and bleaching steps. In such cases, non-enzymatic auxiliaries such as alkali or oxidation agents are typically used to break down the starch, because traditional alpha-amylases are not very compatible with high pH levels and bleaching agents. The non-enzymatic breakdown of the starch size does lead to some fiber damage because of the rather aggressive chemicals used. Accordingly, it would be desirable to use the alpha-amylases of the invention as they have an improved performance in alkaline solutions. The alpha-amylases may be used alone or in combination with a cellulase when desizing cellulose-containing fabric or textile.

Desizing and bleaching processes are well known in the art. For instance, such processes are described in WO 95/21247, U.S. Pat. No. 4,643,736, EP 119,920 hereby incorporate by reference.

Commercially available products for desizing include AQUAZYME® and AQUAZYME® ULTRA from Novozymes A/S.

Beer Making

The alpha-amylases of the invention may also be very useful in a beer-making process; the alpha-amylases will typically be added during the mashing process.

Detergent Compositions

The alpha-amylase of the invention may be added to and thus become a component of a detergent composition.

The detergent composition of the invention may for example be formulated as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations.

In a specific aspect, the invention provides a detergent additive comprising the enzyme of the invention. The detergent additive as well as the detergent composition may comprise one or more other enzymes such as a protease, a lipase, a peroxidase, another amylolytic enzyme, e.g., another alpha-amylase, glucoamylase, maltogenic amylase, CGTase and/or a cellulase, mannanase (such as MANNAWAY™ from Novozymes, Denmark)), pectinase, pectine lyase, cutinase, and/or laccase.

In general the properties of the chosen enzyme(s) should be compatible with the selected detergent, (i.e., pH-optimum, compatibility with other enzymatic and non-enzymatic ingredients, etc.), and the enzyme(s) should be present in effective amounts.

Proteases: Suitable proteases include those of animal, vegetable or microbial origin. Microbial origin is preferred. Chemically modified or protein engineered mutants are included. The protease may be a serine protease or a metallo protease, preferably an alkaline microbial protease or a trypsin-like protease. Examples of alkaline proteases are subtilisins, especially those derived from *Bacillus*, e.g., subtilisin Novo, subtilisin Carlsberg, subtilisin 309, subtilisin 147 and subtilisin 168 (described in WO 89/06279). Examples of trypsin-like pro-teases are trypsin (e.g., of porcine or bovine origin) and the *Fusarium* protease described in WO 89/06270 and WO 94/25583.

Examples of useful proteases are the variants described in WO 92/19729, WO 98/20115, WO 98/20116, and WO 98/34946, especially the variants with substitutions in one or more of the following positions: 27, 36, 57, 76, 87, 97, 101, 104, 120, 123, 167, 170, 194, 206, 218, 222, 224, 235 and 274.

Preferred commercially available protease enzymes include ALCALASE®, SAVINASE®, PRIMASE®, DURALASE®, ESPERASE®, and KANNASE® (from Novozymes A/S), MAXATASE®, MAXACAL, MAXAPEM®, PROPERASE®, PURAFECT®, PURAFECT OXP®, FN2®, FN3®, FN4® (Genencor International Inc.).

Lipases: Suitable lipases include those of bacterial or fungal origin. Chemically modified or protein engineered mutants are included. Examples of useful lipases include lipases from *Humicola* (synonym *Thermomyces*), e.g., from *H. lanuginosa* (*T. lanuginosus*) as described in EP 258 068 and EP 305 216 or from *H. insolens* as described in WO 96/13580, a *Pseudomonas* lipase, e.g., from *P. alcaligenes* or *P. pseudoalcaligenes* (EP 218 272), *P. cepacia* (EP 331 376), *P. stutzeri* (GB 1,372,034), *P. fluorescens, Pseudomonas* sp. strain SD 705 (WO 95/06720 and WO 96/27002), *P. wisconsinensis* (WO 96/12012), a *Bacillus* lipase, e.g., from *B. subtilis* (Dartois et al. (1993), Biochemica et Biophysica Acta, 1131, 253-360), *B. stearothermophilus* (JP 64/744992) or *B. pumilus* (WO 91/16422).

Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079 and WO 97/07202.

Preferred commercially available lipase enzymes include LIPOLASE™ and LIPOLASE ULTRA™ (Novozymes A/S).

Amylases: Suitable amylases (alpha and/or beta) include those of bacterial or fungal origin. Chemically modified or protein engineered mutants are included. Amylases include, for example, alpha-amylases obtained from Bacillus, e.g., a special strain of B. licheniformis, described in more detail in GB 1,296,839. Examples of useful alpha-amylases are the variants described in WO 94/02597, WO 94/18314, WO 96/23873, and WO 97/43424, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444.

Commercially available alpha-amylases are DURAMYL™, LIQUEZYME™ TERMAMYL™, NATALASE™, FUNGAMYL™ and BAN™ (Novozymes A/S), RAPIDASE™ and PURASTAR™ (from Genencor International Inc.).

Cellulases: Suitable cellulases include those of bacterial or fungal origin. Chemically modified or protein engineered mutants are included. Suitable cellulases include cellulases from the genera Bacillus, Pseudomonas, Humicola, Fusarium, Thielavia, Acremonium, e.g., the fungal cellulases produced from Humicola insolens, Myceliophthora thermophila and Fusarium oxysporum disclosed in U.S. Pat. No. 4,435,307, U.S. Pat. No. 5,648,263, U.S. Pat. No. 5,691,178, U.S. Pat. No. 5,776,757 and WO 89/09259.

Especially suitable cellulases are the alkaline or neutral cellulases having colour care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. No. 5,457,046, U.S. Pat. No. 5,686,593, U.S. Pat. No. 5,763,254, WO 95/24471, WO 98/12307 and PCT/DK98/00299.

Commercially available cellulases include CELLUZYME®, and CAREZYME® (Novozymes A/S), CLAZINASE®, and PURADAX HA® (Genencor International Inc.), and KAC-500(B)® (Kao Corporation).

Peroxidases/Oxidases: Suitable peroxidases/oxidases include those of plant, bacterial or fungal origin. Chemically modified or protein engineered mutants are included. Examples of useful peroxidases include peroxidases from Coprinus, e.g., from C. cinereus, and variants thereof as those described in WO 93/24618, WO 95/10602, and WO 98/15257.

Commercially available peroxidases include GUARDZYME® (Novozymes A/S).

The detergent enzyme(s) may be included in a detergent composition by adding separate additives containing one or more enzymes, or by adding a combined additive comprising all of these enzymes. A detergent additive of the invention, i.e., a separate additive or a combined additive, can be formulated, e.g., granulate, a liquid, a slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonyl-phenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The detergent composition of the invention may be in any convenient form, e.g., a bar, a tablet, a powder, a granule, a paste or a liquid. A liquid detergent may be aqueous, typically containing up to 70% water and 0-30% organic solvent, or non-aqueous.

The detergent composition comprises one or more surfactants, which may be non-ionic including semi-polar and/or anionic and/or cationic and/or zwitterionic. The surfactants are typically present at a level of from 0.1% to 60% by weight.

When included therein the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid or soap.

When included therein the detergent will usually contain from about 0.2% to about 40% of a non-ionic surfactant such as alcohol ethoxylate, nonyl-phenol ethoxylate, alkylpolyglycoside, alkyldimethylamine-oxide, ethoxylated fatty acid monoethanol-amide, fatty acid monoethanolamide, polyhydroxy alkyl fatty acid amide, or N-acyl N-alkyl derivatives of glucosamine ("glucamides").

The detergent may contain 0-65% of a detergent builder or complexing agent such as zeolite, diphosphate, triphosphate, phosphonate, carbonate, citrate, nitrilotriacetic acid, ethylenediaminetetraacetic acid, diethylenetriaminepentaacetic acid, alkyl- or alkenylsuccinic acid, soluble silicates or layered silicates (e.g. SKS-6 from Hoechst).

The detergent may comprise one or more polymers. Examples are carboxymethylcellulose, poly(vinyl-pyrrolidone), poly (ethylene glycol), poly(vinyl alcohol), poly(vinylpyridine-N-oxide), poly(vinylimidazole), polycarboxylates such as polyacrylates, maleic/acrylic acid copolymers and lauryl methacrylate/acrylic acid co-polymers.

The detergent may contain a bleaching system, which may comprise a $H_2O_2$ source such as perborate or percarbonate which may be combined with a peracid-forming bleach activator such as tetraacetylethylenediamine or nonanoyloxybenzenesulfonate. Alternatively, the bleaching system may comprise peroxyacids of, e.g., the amide, imide, or sulfone type.

The enzyme(s) of the detergent composition of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in, e.g., WO 92/19709 and WO 92/19708.

The detergent may also contain other conventional detergent ingredients such as e.g. fabric conditioners including clays, foam boosters, suds suppressors, anti-corrosion agents, soil-suspending agents, anti-soil re-deposition agents, dyes, bactericides, optical brighteners, hydrotropes, tarnish inhibitors, or perfumes.

It is at present contemplated that in the detergent compositions any enzyme, in particular the enzyme of the invention, may be added in an amount corresponding to 0.01-100 mg of enzyme protein per liter of wash liquor, preferably 0.05-5 mg of enzyme protein per liter of wash liquor, in particular 0.1-1 mg of enzyme protein per liter of wash liquor.

The enzyme of the invention may additionally be incorporated in the detergent formulations disclosed in WO 97/07202, which is hereby incorporated as reference.

Dishwash Detergent Compositions

The enzyme of the invention mat also be used in dish wash detergent compositions, including the following:

| 1) POWDER AUTOMATIC DISHWASHING COMPOSITION | |
|---|---|
| Nonionic surfactant | 0.4-2.5% |
| Sodium metasilicate | 0-20% |
| Sodium disilicate | 3-20% |
| Sodium triphosphate | 20-40% |
| Sodium carbonate | 0-20% |
| Sodium perborate | 2-9% |
| Tetraacetyl ethylene diamine (TAED) | 1-4% |
| Sodium sulphate | 5-33% |
| Enzymes | 0.0001-0.1% |

| 2) POWDER AUTOMATIC DISHWASHING COMPOSITION | |
|---|---|
| Nonionic surfactant (e.g. alcohol ethoxylate) | 1-2% |
| Sodium disilicate | 2-30% |
| Sodium carbonate | 10-50% |
| Sodium phosphonate | 0-5% |
| Trisodium citrate dihydrate | 9-30% |
| Nitrilotrisodium acetate (NTA) | 0-20% |
| Sodium perborate monohydrate | 5-10% |
| Tetraacetyl ethylene diamine (TAED) | 1-2% |
| Polyacrylate polymer (e.g. maleic acid/acrylic acid copolymer) | 6-25% |
| Enzymes | 0.0001-0.1% |
| Perfume | 0.1-0.5% |
| Water | 5-10 |

| 3) POWDER AUTOMATIC DISHWASHING COMPOSITION | |
|---|---|
| Nonionic surfactant | 0.5-2.0% |
| Sodium disilicate | 25-40% |
| Sodium citrate | 30-55% |
| Sodium carbonate | 0-29% |
| Sodium bicarbonate | 0-20% |
| Sodium perborate monohydrate | 0-15% |
| Tetraacetyl ethylene diamine (TAED) | 0-6% |
| Maleic acid/acrylic acid copolymer | 0-5% |
| Clay | 1-3% |
| Polyamino acids | 0-20% |
| Sodium polyacrylate | 0-8% |
| Enzymes | 0.0001-0.1% |

| 4) POWDER AUTOMATIC DISHWASHING COMPOSITION | |
|---|---|
| Nonionic surfactant | 1-2% |
| Zeolite MAP | 15-42% |
| Sodium disilicate | 30-34% |
| Sodium citrate | 0-12% |
| Sodium carbonate | 0-20% |
| Sodium perborate monohydrate | 7-15% |
| Tetraacetyl ethylene diamine (TAED) | 0-3% |
| Polymer | 0-4% |
| Maleic acid/acrylic acid copolymer | 0-5% |
| Organic phosphonate | 0-4% |
| Clay | 1-2% |
| Enzymes | 0.0001-0.1% |
| Sodium sulphate | Balance |

| 5) POWDER AUTOMATIC DISHWASHING COMPOSITION | |
|---|---|
| Nonionic surfactant | 1-7% |
| Sodium disilicate | 18-30% |
| Trisodium citrate | 10-24% |
| Sodium carbonate | 12-20% |
| Monopersulphate (2KHSO$_5$•KHSO$_4$•K$_2$SO$_4$) | 15-21% |
| Bleach stabilizer | 0.1-2% |
| Maleic acid/acrylic acid copolymer | 0-6% |
| Diethylene triamine pentaacetate, pentasodium salt | 0-2.5% |
| Enzymes | 0.0001-0.1% |
| Sodium sulphate, water | Balance |

| 6) POWDER AND LIQUID DISHWASHING COMPOSITION WITH CLEANING SURFACTANT SYSTEM | |
|---|---|
| Nonionic surfactant | 0-1.5% |
| Octadecyl dimethylamine N-oxide dihydrate | 0-5% |
| 80:20 wt.C18/C16 blend of octadecyl dimethylamine N-oxide dihydrate and hexadecyldimethyl amine N-oxide dihydrate | 0-4% |
| 70:30 wt.C18/C16 blend of octadecyl bis (hydroxyethyl)amine N-oxide anhydrous and hexadecyl bis (hydroxyethyl)amine N-oxide anhydrous | 0-5% |
| $C_{13}$-$C_{15}$ alkyl ethoxysulfate with an average degree of ethoxylation of 3 | 0-10% |
| $C_{12}$-$C_{15}$ alkyl ethoxysulfate with an average degree of ethoxylation of 3 | 0-5% |
| $C_{13}$-$C_{15}$ ethoxylated alcohol with an average degree of ethoxylation of 12 | 0-5% |
| A blend of $C_{12}$-$C_{15}$ ethoxylated alcohols with an average degree of ethoxylation of 9 | 0-6.5% |
| A blend of $C_{13}$-$C_{15}$ ethoxylated alcohols with an average degree of ethoxylation of 30 | 0-4% |
| Sodium disilicate | 0-33% |
| Sodium tripolyphosphate | 0-46% |
| Sodium citrate | 0-28% |
| Citric acid | 0-29% |
| Sodium carbonate | 0-20% |
| Sodium perborate monohydrate | 0-11.5% |
| Tetraacetyl ethylene diamine (TAED) | 0-4% |
| Maleic acid/acrylic acid copolymer | 0-7.5% |
| Sodium sulphate | 0-12.5% |
| Enzymes | 0.0001-0.1% |

| 7) NON-AQUEOUS LIQUID AUTOMATIC DISHWASHING COMPOSITION | |
|---|---|
| Liquid nonionic surfactant (e.g. alcohol ethoxylates) | 2.0-10.0% |
| Alkali metal silicate | 3.0-15.0% |
| Alkali metal phosphate | 20.0-40.0% |
| Liquid carrier selected from higher glycols, polyglycols, polyoxides, glycolethers | 25.0-45.0% |
| Stabilizer (e.g. a partial ester of phosphoric acid and a $C_{16}$-$C_{18}$ alkanol) | 0.5-7.0% |
| Foam suppressor (e.g. silicone) | 0-1.5% |
| Enzymes | 0.0001-0.1% |

| 8) NON-AQUEOUS LIQUID DISHWASHING COMPOSITION | |
|---|---|
| Liquid nonionic surfactant (e.g. alcohol ethoxylates) | 2.0-10.0% |
| Sodium silicate | 3.0-15.0% |
| Alkali metal carbonate | 7.0-20.0% |
| Sodium citrate | 0.0-1.5% |
| Stabilizing system (e.g. mixtures of finely divided silicone and low molecular weight dialkyl polyglycol ethers) | 0.5-7.0% |
| Low molecule weight polyacrylate polymer | 5.0-15.0% |
| Clay gel thickener (e.g. bentonite) | 0.0-10.0% |
| Hydroxypropyl cellulose polymer | 0.0-0.6% |
| Enzymes | 0.0001-0.1% |
| Liquid carrier selected from higher lycols, polyglycols, polyoxides and glycol ethers | Balance |

| 9) THIXOTROPIC LIQUID AUTOMATIC DISHWASHING COMPOSITION | |
|---|---|
| $C_{12}$-$C_{14}$ fatty acid | 0-0.5% |
| Block co-polymer surfactant | 1.5-15.0% |
| Sodium citrate | 0-12% |
| Sodium tripolyphosphate | 0-15% |
| Sodium carbonate | 0-8% |
| Aluminium tristearate | 0-0.1% |
| Sodium cumene sulphonate | 0-1.7% |
| Polyacrylate thickener | 1.32-2.5% |
| Sodium polyacrylate | 2.4-6.0% |
| Boric acid | 0-4.0% |
| Sodium formate | 0-0.45% |
| Calcium formate | 0-0.2% |
| Sodium n-decydiphenyl oxide disulphonate | 0-4.0% |
| Monoethanol amine (MEA) | 0-1.86% |

-continued

| | |
|---|---|
| Sodium hydroxide (50%) | 1.9-9.3% |
| 1,2-Propanediol | 0-9.4% |
| Enzymes | 0.0001-0.1% |
| Suds suppressor, dye, perfumes, water | Balance |
| 10) LIQUID AUTOMATIC DISHWASHING COMPOSITION | |
| Alcohol ethoxylate | 0-20% |
| Fatty acid ester sulphonate | 0-30% |
| Sodium dodecyl sulphate | 0-20% |
| Alkyl polyglycoside | 0-21% |
| Oleic acid | 0-10% |
| Sodium disilicate monohydrate | 18-33% |
| Sodium citrate dihydrate | 18-33% |
| Sodium stearate | 0-2.5% |
| Sodium perborate monohydrate | 0-13% |
| Tetraacetyl ethylene diamine (TAED) | 0-8% |
| Maleic acid/acrylic acid copolymer | 4-8% |
| Enzymes | 0.0001-0.1% |
| 11) LIQUID AUTOMATIC DISHWASHING COMPOSITION CONTAINING PROTECTED BLEACH PARTICLES | |
| Sodium silicate | 5-10% |
| Tetrapotassium pyrophosphate | 15-25% |
| Sodium triphosphate | 0-2% |
| Potassium carbonate | 4-8% |
| Protected bleach particles, e.g. chlorine | 5-10% |
| Polymeric thickener | 0.7-1.5% |
| Potassium hydroxide | 0-2% |
| Enzymes | 0.0001-0.1% |
| Water | Balance |

11) Automatic dishwashing compositions as described in 1), 2), 3), 4), 6) and 10), wherein perborate is replaced by percarbonate.
12) Automatic dishwashing compositions as described in 1)-6) which additionally contain a manganese catalyst. The manganese catalyst may, e.g., be one of the compounds described in "Efficient manganese catalysts for low-temperature bleaching", Nature 369, 1994, pp. 637-639.

Uses

The present invention is also directed to methods for using an alpha-amylase variant of the invention in detergents, in particular laundry detergent compositions and dishwashing detergent compositions, hard surface cleaning compositions, and in composition for desizing of textiles, fabrics or garments, for production of pulp and paper, beer making, ethanol production, and starch conversion processes as described above.

Compositions

The invention also related to composition comprising a variant of the invention, and in a preferred embodiment also a *B. stearothermophilus* alpha-amylase (BSG), in particular a variant thereof.

In another embodiment the composition comprises beside a variant of the invention a glucoamylase, in particular a glucoamylase originating from *Aspergillus niger* (e.g., the G1 or G2 *A. niger* AMG disclosed in Boel et al. (1984), "Glucoamylases G1 and G2 from *Aspergillus niger* are synthesized from two different but closely related mRNAs", EMBO J. 3 (5), p. 1097-1102, or a variant therefore, in particular a variant disclosed in WO 00/04136 or WO 01/04273 or the *Talaromyces emersonii* AMG disclosed in WO 99/28448.

In an embodiment the composition of the invention also comprises a pullulanase, in particular a *Bacillus* pullulanase.

Materials and Methods

Materials:

*Bacillus licheniformis* alpha-amylase shown in SEQ ID NO: 8 and also available from Novozymes A/S, Denmark.

AA560: SEQ ID NO: 12; disclosed in WO 00/60060; deposited on 25 Jan. 1999 at DSMZ and assigned the DSMZ no. 12649.

LB medium (In 1 liter $H_2O$: 10 g bacto-tryptone, 5 g bacto-yeast extract, 10 g NaCl, pH adjusted to 7.0 w. NaOH, autoclaved).

TY agar plates (In 1 liter $H_2O$: 16 g bacto-tryptone, 10 g bacto-yeast extract, 5 g NaCl, pH adjusted to 7.0 w. NaOH, and 15 g bacto-agar is added prior to autoclaving).

10% Lugol solution (Iodine/Potassium iodine solution; made by 10-fold dil. in $H_2O$ of stock: Sigma Cat. no. L 6146).

*Bacillus subtilis* SHA273: see WO 95/10603

Detergents:

Model detergent: A/P (Asia/Pacific) Model Detergent has the following composition: 20% STPP (sodium tripolyphosphate), 25% $Na_2SO_4$, 15% $Na_2CO_3$, 20% LAS (linear alkylbenzene sulfonate, Nansa 80S), 5% C12-C15 alcohol ethoxylate (Dobanol 25-7), 5% $Na_2Si_2O_5$, 0.3% NaCl.

Omo Multi Acao (Brazil),
Omo concentrated powder (EU) (Unilever)
Ariel Futur liquid (EU) (Procter and Gamble)
Ariel Essential (EU) (Procter and Gamble)

Plasmids pDN1528 contains the complete gene encoding Termamyl, amyL, the expression of which is directed by its own promoter. Further, the plasmid contains the origin of replication, ori, from plasmid pUB110 and the cat gene from plasmid pC194 conferring resistance towards chloramphenicol. pDN1528 is shown in FIG. 9 of WO 96/23874.

Methods:

Filter Screening Assays

The below assays can be used to screening of Termamyl-like alpha-amylase variants having altered stability at high or low pH and/or under $Ca^{2+}$ depleted conditions compared to the parent enzyme and Termamyl-like alpha-amylase.

High pH Filter Assay

*Bacillus* libraries are plated on a sandwich of cellulose acetate (OE 67, Schleicher & Schuell, Dassel, Germany)- and nitrocellulose filters (Protran-Ba 85, Schleicher & Schuell, Dassel, Germany) on TY agar plates with 10 micro g/ml kanamycin at 37° C. for at least 21 hours. The cellulose acetate layer is located on the TY agar plate.

Each filter sandwich is specifically marked with a needle after plating, but before incubation in order to be able to localize positive variants on the filter and the nitrocellulose filter with bound variants is transferred to a container with glycin-NaOH buffer, pH 8.6-10.6 and incubated at room temperature (can be altered from 10-60° C.) for 15 min. The cellulose acetate filters with colonies are stored on the TY-plates at room temperature until use. After incubation, residual activity is detected on plates containing 1% agarose, 0.2% starch in glycin-NaOH buffer, pH 8.6-10.6. The assay plates with nitrocellulose filters are marked the same way as the filter sandwich and incubated for 2 hours at room temperature. After removal of the filters the assay plates are stained with 10% Lugol solution. Starch degrading variants are detected as white spots on dark blue background and then identified on the storage plates. Positive variants are rescreened twice under the same conditions as the first screen.

Low Calcium Filter Assay

*Bacillus* libraries are plated on a sandwich of cellulose acetate (OE 67, Schleicher & Schuell, Dassel, Germany)— and nitrocellulose filters (Protran-Ba 85, Schleicher & Schuell, Dassel, Germany) on TY agar plates with a relevant antibiotic, e.g., kanamycin or chloramphenicol, at 37° C. for at least 21 hours. The cellulose acetate layer is located on the TY agar plate.

Each filter sandwich is specifically marked with a needle after plating, but before incubation in order to be able to localize positive variants on the filter and the nitrocellulose filter with bound variants is transferred to a container with carbonate/bicarbonate buffer pH 8.5-10 and with different EDTA concentrations (0.001 mM-100 mM). The filters are incubated at room temperature for 1 hour. The cellulose acetate filters with colonies are stored on the TY-plates at room temperature until use. After incubation, residual activity is detected on plates containing 1% agarose, 0.2% starch in carbonate/bicarbonate buffer pH 8.5-10. The assay plates with nitrocellulose filters are marked the same way as the filter sandwich and incubated for 2 hours at room temperature. After removal of the filters the assay plates are stained with 10% Lugol solution. Starch degrading variants are detected as white spots on dark blue background and then identified on the storage plates. Positive variants are rescreened twice under the same conditions as the first screen.

Low pH Filter Assay

Bacillus libraries are plated on a sandwich of cellulose acetate (OE 67, Schleicher & Schuell, Dassel, Germany)—and nitrocellulose filters (Protran-Ba 85, Schleicher & Schuell, Dassel, Germany) on TY agar plates with 10 micro g/ml chloramphenicol at 37° C. for at least 21 hours. The cellulose acetate layer is located on the TY agar plate.

Each filter sandwich is specifically marked with a needle after plating, but before incubation in order to be able to localize positive variants on the filter, and the nitrocellulose filter with bound variants is transferred to a container with citrate buffer, pH 4.5 and incubated at 80° C. for 20 minutes (when screening for variants in the wild type backbone) or 85° C. for 60 minutes (when screening for variants of the parent alpha-amylase). The cellulose acetate filters with colonies are stored on the TY-plates at room temperature until use. After incubation, residual activity is detected on assay plates containing 1% agarose, 0.2% starch in citrate buffer, pH 6.0. The assay plates with nitrocellulose filters are marked the same way as the filter sandwich and incubated for 2 hours at 50° C. After removal of the filters the assay plates are stained with 10% Lugol solution. Starch degrading variants are detected as white spots on dark blue background and then identified on the storage plates. Positive variants are re-screened twice under the same conditions as the first screen.

Secondary Screening

Positive transformants after rescreening are picked from the storage plate and tested in a secondary plate assay. Positive transformants are grown for 22 hours at 37° C. in 5 ml LB+chloramphenicol. The Bacillus culture of each positive transformant and as a control a clone expressing the corresponding backbone are incubated in citrate buffer, pH 4.5 at 90° C. and samples are taken at 0, 10, 20, 30, 40, 60 and 80 minutes. A 3 micro liter sample is spotted on an assay plate. The assay plate is stained with 10% Lugol solution. Improved variants are seen as variants with higher residual activity (detected as halos on the assay plate) than the backbone. The improved variants are determined by nucleotide sequencing.

Stability Assay of Unpurified Variants:

Bacillus cultures expressing the variants to be analysed are grown for 21 hours at 37° C. in 10 ml LB+chloramphenicol. 800 micro liter culture is mixed with 200 micro l citrate buffer, pH 4.5. A number of 70 micro l aliquots corresponding to the number of sample time points are made in PCR tubes and incubated at 70° C. or 90° C. for various time points (typically 5, 10, 15, 20, 25 and 30 minutes) in a PCR machine. The 0 min sample is not incubated at high temperature. Activity in the sample is measured by transferring 20 micro l to 200 micro l of the alpha-amylase PNP-$G_7$ substrate MPR3 ((Boehringer Mannheim Cat. no. 1660730) as described below under "Assays for Alpha-Amylase Activity". Results are plotted as percentage activity (relative to the 0 time point) versus time, or stated as percentage residual activity after incubation for a certain period of time.

Fermentation and Purification of Alpha-Amylase Variants

A B. subtilis strain harbouring the relevant expression plasmid is streaked on a LB-agar plate with 10 micro g/ml kanamycin from −80° C. stock, and grown overnight at 37° C. The colonies are transferred to 100 ml PS-1 media supplemented with 10 micro g/ml chloamphinicol in a 500 ml shaking flask.

Composition of PS-1 Medium:

| Pearl sugar | 100 g/l |
| Soy Bean Meal | 40 g/l |
| $Na_2HPO_4$, $12H_2O$ | 10 g/l |
| Pluronic ™ PE 6100 | 0.1 g/l |
| $CaCO_3$ | 5 g/l |

The culture is shaken at 37° C. at 270 rpm for 5 days.

Cells and cell debris are removed from the fermentation broth by centrifugation at 4500 rpm in 20-25 minutes. Afterwards the supernatant is filtered to obtain a completely clear solution. The filtrate is concentrated and washed on a UF-filter (10000 cut off membrane) and the buffer is changed to 20 mM Acetate pH 5.5. The UF-filtrate is applied on a S-sepharose F.F. and elution is carried out by step elution with 0.2M NaCl in the same buffer. The eluate is dialysed against 10 mM Tris, pH 9.0 and applied on a Q-sepharose F.F. and eluted with a linear gradient from 0-0.3M NaCl over 6 column volumes. The fractions that contain the activity (measured by the Phadebas assay) are pooled, pH was adjusted to pH 7.5 and remaining color was removed by a treatment with 0.5% W/vol. active coal in 5 minutes.

Stability Determination of Purified Variants

All stability trials of purified variants are made using the same set up. The method is as follows:

The enzyme is incubated under the relevant conditions (1-4). Samples are taken at various time points, e.g., after 0, 5, 10, 15 and 30 minutes and diluted 25 times (same dilution for all taken samples) in assay buffer (0.1M 50 mM Britton buffer pH 7.3) and the activity is measured using the Phadebas assay (Pharmacia) under standard conditions pH 7.3, 37° C.

The activity measured before incubation (0 minutes) is used as reference (100%). The decline in percent is calculated as a function of the incubation time. The table shows the residual activity after, e.g., 30 minutes of incubation.

Specific Activity Determination

The specific activity is determined using the Phadebas® assay (Pharmacia) as activity/mg enzyme. The manufactures instructions are followed (see also below under "Assay for Alpha-Amylase Activity).

Determination of Isoelectric Point

The pI is determined by isoelectric focusing (ex: Pharmacia, Ampholine, pH 3.5-9.3).

Stability Determination

The amylase stability is measured using the method as follows:

The enzyme is incubated under the relevant conditions. Samples are taken at various time points, e.g., after 0, 5, 10, 15 and 30 minutes and diluted 25 times (same dilution for all taken samples) in assay buffer (0.1M 50 mM Britton buffer pH 7.3) and the activity is measured using the Phadebas assay (Pharmacia) under standard conditions pH 7.3, 37° C.

The activity measured before incubation (0 minutes) is used as reference (100%). The decline in percent is calculated as a function of the incubation time. The table shows the residual activity after, e.g., 30 minutes of incubation.

Measurement of the Calcium- and pH-Dependent Stability

Normally industrial liquefaction processes runs using pH 6.0-6.2 as liquefaction pH and an addition of 40 ppm free calcium in order to improve the stability at 95° C.-105° C. Some of the herein proposed substitutions have been made in order to improve the stability at
1. lower pH than pH 6.2 and/or
2. at free calcium levels lower than 40 ppm free calcium.

Two different methods can be used to measure the alterations in stability obtained by the different substitutions in the alpha-amylase in question:

Method 1. One assay which measures the stability at reduced pH, pH 5.0, in the presence of 5 ppm free calcium. 10 micro 9 of the variant are incubated under the following conditions: A 0.1 M acetate solution, pH adjusted to pH 5.0, containing 5 ppm calcium and 5% w/w common corn starch (free of calcium). Incubation is made in a water bath at 95° C. for 30 minutes.

Method 2. One assay, which measure the stability in the absence of free calcium and where the pH is maintained at pH 6.0. This assay measures the decrease in calcium sensitivity: 10 micro g of the variant were incubated under the following conditions: A 0.1 M acetate solution, pH adjusted to pH 6.0, containing 5% w/w common corn starch (free of calcium). Incubation was made in a water bath at 95° C. for 30 minutes.

Oxidation Stability Determination

Raw filtered culture broths with different variants of the Invention are diluted to an amylase activity of 100 KNU/ml (defined above) in 50 mM of a Britton-Robinson buffer at pH 9.0 and incubated at 40° C. Subsequently $H_2O_2$ is added to a concentration of 200 mM, and the pH value is re-adjusted to 9.0. The activity is now measured after 15 seconds and after 5, 15, and 30 minutes. The absorbance of the resulting blue solution, measured spectrophotometrically at 620 nm, is a function of the alpha-amylase activity.

Washing Performance

Washing performance is evaluated by washing soiled test swatches for 15 and 30 minutes at 25° C. and 40° C., respectively; at a pH in the range from 9-10.5; water hardness in the range from 6 to 15 dH; Ca:Mg ratio of from 2:1 to 4:1, in different detergent solutions (see above as described above in the Materials section) dosed from 1 to 5 g/l, such as 3 g/l, dependent on the detergent with the alpha-amylase variant in question.

The recombinant alpha-amylase variant is added to the detergent solutions at concentrations of for instance 0.01-5 mg/l. The test swatches are soiled with orange rice starch (CS-28 swatches available from CFT, Center for Test Material, Holland).

After washing, the swatches are evaluated by measuring the remission at 460 nm using an Elrepho Remission Spectrophotometer. The results are expressed as DeltaR=remission (° R of the swatch washed with the alpha-amylase minus the remission of a swatch washed at the same conditions without the alpha-amylase.

Assays for Alpha-Amylase Activity

1. Phadebas Assay

Alpha-amylase activity is determined by a method employing Phadebas® tablets as substrate. Phadebas tablets (Phadebas® Amylase Test, supplied by Pharmacia Diagnostic) contain a cross-linked insoluble blue-colored starch polymer, which has been mixed with bovine serum albumin and a buffer substance and tableted.

For every single measurement one tablet is suspended in a tube containing 5 ml 50 mM Britton-Robinson buffer (50 mM acetic acid, 50 mM phosphoric acid, 50 mM boric acid, 0.1 mM $CaCl_2$, pH adjusted to the value of interest with NaOH). The test is performed in a water bath at the temperature of interest. The alpha-amylase to be tested is diluted in x ml of 50 mM Britton-Robinson buffer. 1 ml of this alpha-amylase solution is added to the 5 ml 50 mM Britton-Robinson buffer. The starch is hydrolyzed by the alpha-amylase giving soluble blue fragments. The absorbance of the resulting blue solution, measured spectrophotometrically at 620 nm, is a function of the alpha-amylase activity.

It is important that the measured 620 nm absorbance after 10 or 15 minutes of incubation (testing time) is in the range of 0.2 to 2.0 absorbance units at 620 nm. In this absorbance range there is linearity between activity and absorbance (Lambert-Beer law). The dilution of the enzyme must therefore be adjusted to fit this criterion. Under a specified set of conditions (temp., pH, reaction time, buffer conditions) 1 mg of a given alpha-amylase will hydrolyze a certain amount of substrate and a blue colour will be produced. The colour intensity is measured at 620 nm. The measured absorbance is directly proportional to the specific activity (activity/mg of pure alpha-amylase protein) of the alpha-amylase in question under the given set of conditions.

2. Alternative Method

Alpha-amylase activity is determined by a method employing the PNP-$G_7$ substrate. PNP-$G_7$ which is a abbreviation for p-nitrophenyl-alpha,D-maltoheptaoside is a blocked oligosaccharide which can be cleaved by an endo-amylase. Following the cleavage, the alpha-Glucosidase included in the kit digest the substrate to liberate a free PNP molecule which has a yellow colour and thus can be measured by visible spectophometry at $\lambda$=405 nm (400-420 nm). Kits containing PNP-$G_7$ substrate and alpha-Glucosidase is manufactured by Boehringer-Mannheim (cat. No. 1054635).

To prepare the reagent solution 10 ml of substrate/buffer solution is added to 50 ml enzyme/buffer solution as recommended by the manufacturer. The assay is performed by transferring 20 micro l sample to a 96 well microtitre plate and incubating at 25° C. 200 micro l reagent solution pre-equilibrated to 25° C. is added. The solution is mixed and pre-incubated 1 minute and absorption is measured every 30 sec. over 4 minutes at OD 405 nm in an ELISA reader.

The slope of the time dependent absorption-curve is directly proportional to the activity of the alpha-amylase in question under the given set of conditions.

Determination of LAS Sensitivity

The variant is incubated with different concentrations of LAS (linear alkyl benzene sulphonate; Nansa 1169/P) for 10 minutes at 40° C.

The residual activity is determined using the Phadebas® assay method or the alternative method employing the PNP-$G_7$ substrate.

LAS is diluted in 0.1 M phosphate buffer pH 7.5.
The following concentrations are used:
500 ppm, 250 ppm, 100 ppm, 50 ppm, 25 ppm, and 10 ppm on no LAS.

The variant is diluted in the different LAS buffers to concentration of 0.01-5 mg/l in a total volume of 10 ml and incubated for 10 minutes in a temperature controlled water bath. The incubation is stopped by transferring a small aliquot into cold assay buffer. It is important that during activity measurement the LAS concentration is below 1 ppm, in order not to affect the activity measurement.

Then the residual activity is determined in duplicate using the above mentioned Phadebas® assay or alternative method.
The activity is measured after subtraction of the blank.
The activity with no LAS is 100%.

EXAMPLES

Example 1

Construction of Variants of the Invention and Determination of Altered Properties

The below listed variants are constructed as described in EXAMPLE 1 of WO 00/29560 (from Novozymes A/S) in the parent *Bacillus licheniformis* alpha-amylase shown in SEQ ID NO: 8.

G5A,R,N,D,C,Q,E,H,I,L,K,M,F,P,S,T,W,Y,V;
T6A,R,N,D,C,Q,E,G,H,I,L,K,M,F,P,S,W,Y,V;
G36A,R,N,D,C,Q,E,H,I,L,K,M,F,P,S,T,W,Y,V;
I37A,R,N,D,C,Q,E,G,H,L,K,M,F,P,S,T,W,Y,V;
T38A,R,N,D,C,Q,E,G,H,I,L,K,M,F,P,S,W,Y,V;
A39R,N,D,C,Q,E,G,H,I,L,K,M,F,P,S,T,W,Y,V;
I42A,R,N,D,C,Q,E,G,H,L,K,M,F,P,S,T,W,Y,V;
A45R,N,D,C,Q,E,G,H,I,L,K,M,F,P,S,T,W,Y,V;
K47A,R,N,D,C,Q,E,G,H,I,L,M,F,P,S,T,W,Y,V;
D63A,R,N,C,Q,E,G,H,I,L,K,M,F,P,S,T,W,Y,V;
E66A,R,N,D,C,Q,G,H,I,L,K,M,F,P,S,T,W,Y,V;
Q69A,R,N,D,C,E,G,H,I,L,K,M,F,P,S,T,W,Y,V;
K70A,R,N,D,C,Q,E,G,H,I,L,M,F,P,S,T,W,Y,V;
G71A,R,N,D,C,Q,E,H,I,L,K,M,F,P,S,T,W,Y,V;
T72A,R,N,D,C,Q,E,G,H,I,L,K,M,F,P,S,W,Y,V;
R74A,N,D,C,Q,E,G,H,I,L,K,M,F,P,S,T,W,Y,V;
T75A,R,N,D,C,Q,E,G,H,I,L,K,M,F,P,S,W,Y,V;
K76A,R,N,D,C,Q,E,G,H,I,L,M,F,P,S,T,W,Y,V;
T79A,R,N,D,C,Q,E,G,H,I,L,K,M,F,P,S,W,Y,V;
E82A,R,N,D,C,Q,G,H,I,L,K,M,F,P,S,T,W,Y,V;
L83A,R,N,D,C,Q,E,G,H,I,K,M,F,P,S,T,W,Y,V;
A86R,N,D,C,Q,E,G,H,I,L,K,M,F,P,S,T,W,Y,V;
I87A,R,N,D,C,Q,E,G,H,L,K,M,F,P,S,T,W,Y,V;
S89A,R,N,D,C,Q,E,G,H,I,L,K,M,F,P,T,W,Y,V;
R93A,N,D,C,Q,E,G,H,I,L,K,M,F,P,S,T,W,Y,V;
T112A,R,N,D,C,Q,E,G,H,I,L,K,M,F,P,S,W,Y,V;
E113A,R,N,D,C,Q,G,H,I,L,K,M,F,P,S,T,W,Y,V;
A117R,N,D,C,Q,E,G,H,I,L,K,M,F,P,S,T,W,Y,V;
V120A,R,N,D,C,Q,E,G,H,I,L,K,M,F,P,S,T,W,Y;
A137R,N,D,C,Q,E,G,H,I,L,K,M,F,P,S,T,W,Y,V;
K213A,R,N,D,C,Q,E,G,H,I,L,M,F,P,S,T,W,Y,V;
G216A,R,N,D,C,Q,E,H,I,L,K,M,F,P,S,T,W,Y,V;
A220R,N,D,C,Q,E,G,H,I,L,K,M,F,P,S,T,W,Y,V;
L223A,R,N,D,C,Q,E,G,H,I,K,M,F,P,S,T,W,Y,V;
L225A,R,N,D,C,Q,E,G,H,I,K,M,F,P,S,T,W,Y,V;
D226A,R,N,C,Q,E,G,H,I,L,K,M,F,P,S,T,W,Y,V;
G227A,R,N,D,C,Q,E,H,I,L,K,M,F,P,S,T,W,Y,V
R229A,N,D,C,Q,E,G,H,I,L,K,M,F,P,S,T,W,Y,V;
D243A,R,N,C,Q,E,G,H,I,L,K,M,F,P,S,T,W,Y,V;
V245A,R,N,D,C,Q,E,G,H,I,L,K,M,F,P,S,T,W,Y;
F279A,R,N,D,C,Q,E,G,H,I,L,K,M,P,S,T,W,Y,V;
S282A,R,N,D,C,Q,E,G,H,I,L,K,M,F,P,T,W,Y,V;
T311A,R,N,D,C,Q,E,G,H,I,L,K,M,F,P,S,W,Y,V;
V321A,R,N,D,C,Q,E,G,H,I,L,K,M,F,P,S,T,W,Y;
V324A,R,N,D,C,Q,E,G,H,I,L,K,M,F,P,S,T,W,Y;
L352A,R,N,D,C,Q,E,G,H,I,K,M,F,P,S,T,W,Y,V;
T353A,R,N,D,C,Q,E,G,H,I,L,K,M,F,P,S,W,Y,V;
R354A,N,D,C,Q,E,G,H,I,L,K,M,F,P,S,T,W,Y,V;
G357A,R,N,D,C,Q,E,H,I,L,K,M,F,P,S,T,W,Y,V;
V361A,R,N,D,C,Q,E,G,H,I,L,K,M,F,P,S,T,W,Y;
F362A,R,N,D,C,Q,E,G,H,I,L,K,M,P,S,T,W,Y,V;
G364A,R,N,D,C,Q,E,H,I,L,K,M,F,P,S,T,W,Y,V;
G368A,R,N,D,C,Q,E,H,I,L,K,M,F,P,S,T,W,Y,P;
A390R,N,D,C,Q,E,G,H,I,L,K,M,F,P,S,T,W,Y,V;
A395R,N,D,C,Q,E,G,H,I,L,K,M,F,P,S,T,W,Y,V;
G397A,R,N,D,C,Q,E,H,I,L,K,M,F,P,S,T,W,Y,V;
Q399A,R,N,D,C,E,G,H,I,L,K,M,F,P,S,T,W,Y,V;
H400A,R,N,D,C,Q,E,G,I,L,K,M,F,P,S,T,W,Y,V;
D401A,R,N,C,Q,E,G,H,I,L,K,M,F,P,S,T,W,Y,V;
A425R,N,D,C,Q,E,G,H,I,L,K,M,F,P,S,T,W,Y,V;
D451A,R,N,C,Q,E,G,H,I,L,K,M,F,P,S,T,W,Y,V;
I452A,R,N,D,C,Q,E,G,H,L,K,M,F,P,S,T,W,Y,V;
T453A,R,N,D,C,Q,E,G,H,I,L,K,M,F,P,S,W,Y,V;
G466A,R,N,D,C,Q,E,H,I,L,K,M,F,P,S,T,W,Y,V;
G468A,R,N,D,C,Q,E,H,I,L,K,M,F,P,S,T,W,Y,V;
F470A,R,N,D,C,Q,E,G,H,I,L,K,M,P,S,T,W,Y,V;
H471A,R,N,D,C,Q,E,G,I,L,K,M,F,P,S,T,W,Y,V;
S478A,R,N,D,C,Q,E,G,H,I,L,K,M,F,P,T,W,Y,V
L7A,R,N,D,C,Q,E,G,H,K,M,P,S,Y,V;
M8C;
Q9A,R,N,D,C,G,H,M,P,S,T,W,Y,V;
F11A,N,D,C,Q,G,H,I,L,M,P,S,T,W,Y,V;
E12A,R,N,D,C,G,H,I,L,K,M,F,P,S,T,W,Y,V;
G19A,R,N,D,C,Q,E,H,I,L,K,M,F,P,S,T,W,Y,V;
H21A,R,N,D,C,Q,E,G,I,L,K,M,F,P,S,T,W,Y,V;
W22A,R,N,D,C,Q,E,G,H,I,L,K,M,F,P,S,T,Y,V;
L25A,R,N,D,C,Q,E,G,H,I,K,M,F,P,S,T,W,Y,V;
L32A,R,N,D,C,Q,E,G,H,I,K,M,F,P,S,T,W,Y,V;
V40A,R,N,D,C,Q,E,G,H,I,L,K,M,F,P,S,T,W,Y;
W41A,R,N,D,C,Q,E,G,H,I,L,K,M,F,P,S,T,Y,V;
Y46A,R,D,C,G,K,M,P,W;
G48R,N,D,C,Q,E,H,K,M,F,P,W,Y;
G55A,R,N,D,C,Q,E,H,I,L,K,M,F,P,S,T,W,Y,V;
G57R,N,D,C,Q,E,H,K,M,P,W;
A58R,N,D,C,Q,E,G,H,K,M,S,T,W,Y;
D60A,R,C,Q,E,G,H,I,L,K,M,F,P,S,T,W,Y,V;
Y77A,R,D,C,G,K,M,P,W;
I95A,R,N,D,C,Q,E,G,H,L,K,M,F,P,S,T,W,Y,V;
V97A,R,N,D,C,Q,E,G,H,I,L,K,M,F,P,S,T,W,Y;
Y98A,R,D,C,G,K,M,P,W;
G99R,N,D,C,Q,E,H,I,L,K,M,F,P,S,T,W,Y,V;
D100A,R,C,Q,E,G,H,I,K,M,F,P,S,T,W,Y,V;
V101A,N,C,Q,G,I,L,M,P,S,T,W,Y;
V102N,D,C,Q,E,H,I,L,M,F,P,W,Y;
I103A,N,D,C,Q,E,G,M,P,S,W,Y;
H105A,N,C,Q,G,I,L,M,P,S,T,Y,V;
G107R,N,D,Q,E,H,K,M,F,P,W,Y;
V115R,N,D,C,Q,E,H,I,L,K,M,F,P,S,T,W,Y;
V118R,N,C,Q,E,H,I,L,K,M,F,P,S,T,W,Y;
I135A,R,N,D,C,Q,E,G,H,L,K,M,F,P,S,T,W,Y,V;
T139A,R,N,D,C,Q,E,G,H,I,L,K,M,F,P,S,W,Y,V;
F141A,R,N,D,C,Q,E,G,H,I,L,K,M,P,S,T,W,Y,V;
F143A,R,N,D,C,Q,E,G,H,I,L,K,M,P,S,T,Y,V;
S151A,R,N,D,C,Q,E,G,H,K,M,P,T,Y,V;
H159A,R,N,D,C,Q,E,G,I,L,K,M,F,P,S,T,W,V;
F160A,R,N,D,C,Q,E,G,H,I,L,K,M,P,S,T,W,Y,V;
D161A,R,C,Q,E,G,H,I,L,K,M,F,P,S,T,W,Y,V;
G162A,R,N,D,C,Q,E,H,I,L,K,M,F,P,S,T,W,Y,V;
T163A,R,N,D,C,Q,E,G,H,I,L,K,M,F,P,S,W,Y,V;
D166A,R,N,C,Q,G,H,I,L,K,M,F,P,S,T,W,Y,V;
Y175A,R,D,C,G,K,M,P,W;
F177A,N,D,C,Q,E,H,I,L,K,M,P,S,T,W,Y,V;
D183A,R,C,Q,E,G,H,I,L,K,M,F,P,S,T,W,Y,V;
V186A,R,N,D,C,Q,E,G,H,I,L,K,M,F,P,S,T,W,Y;
S187A,R,C,Q,E,G,H,I,L,K,M,F,P,W,Y,V;
N192A,R,D,C,Q,E,G,H,I,L,K,M,F,P,S,T,W,Y,V;
A199R,N,D,C,Q,E,G,H,I,L,K,M,F,P,S,T,W,Y,V;
D200A,R,C,Q,E,G,H,I,L,K,M,F,P,S,T,W,Y,V;
D202A,R,C,Q,E,G,H,I,L,K,M,F,P,S,T,W,Y,V;
Y203A,R,D,C,G,K,M,P;
V208A,R,N,D,C,Q,E,G,H,L,K,M,F,P,S,T,W,Y;
I212A,N,C,Q,G,H,M,P,S,T,V;
W215A,R,N,D,C,Q,E,G,H,I,L,K,M,F,P,S,T,Y,V;

Y219A,R,D,C,G,K,M,P,W;
F228A,R,N,D,C,Q,E,G,H,I,L,K,M,P,S,T,W,Y,V;
L230A,R,N,D,C,Q,E,G,M,P,S,T,W,Y,V;
V233R,N,C,Q,E,G,H,I,K,M,P,S,T,W,Y;
I236A,C,Q,G,H,M,P,S,T,V;
F238A,R,N,D,C,Q,E,G,H,I,K,M,P,S,T,W,Y,V;
F240A,R,N,D,C,Q,E,G,H,I,L,K,M,P,S,T,W,Y,V;
L241A,N,C,Q,G,H,P,S,T,V;
W244A,R,N,D,C,Q,E,G,H,I,L,K,M,F,P,S,T,Y,V;
V248A,R,N,D,C,Q,E,G,H,I,L,K,M,F,P,S,T,W,Y;
M256C;
T258A,R,N,D,C,Q,E,G,H,I,L,K,M,F,P,S,W,Y,V;
V259A,R,N,D,C,Q,E,G,H,K,M,P,S,T,W,Y;
A260R,N,D,C,Q,E,H,I,L,K,M,F,P,T,W,Y,V;
Y262A,R,D,C,G,K,M,P,W;
L270A,N,C,Q,G,I,M,F,P,S,T,W,Y,V;
Y273A.R,D,C,G,K,M,P;
L274A,R,N,D,C,Q,E,G,H,I,K,M,F,P,S,T,W,Y,V;
T277A,R,N,D,C,Q,E,G,H,K,M,P,S,W,Y,V;
H281A,R,N,D,C,Q,E,G,K,M,P,S,T,W,Y,V;
V283A,R,N,C,Q,E,G,I,L,K,M,F,P,S,T,W,Y;
F284A,R,N,D,C,Q,E,G,I,L,K,M,P,S,T,Y,V;
D285A,R,C,Q,E,G,H,I,K,M,F,P,S,T,W,Y,V;
V286A,R,D,C,Q,E,G,H,I,K,M,F,P,S,T,W,Y;
P287R,N,D,C,Q,E,G,H,I,L,K,M,F,S,T,W,Y,V;
L288A,R,N,D,C,Q,E,G,H,I,K,M,F,P,S,T,W,Y,V;
H289A,R,N,D,C,Q,E,G,I,L,K,M,F,P,S,T,W,Y,V;
F292A,R,N,D,C,Q,E,G,H,I,L,K,M,P,S,T,W,Y,V
A295R,N,D,C,Q,E,G,H,I,L,K,M,F,P,S,T,W,Y,V;
S296A,R,N,D,C,Q,E,G,H,I,L,K,M,F,P,T,W,Y,V;
M304C;
L307A,R,N,D,C,Q,E,G,H,I,K,M,F,P,S,T,W,Y,V;
V312A,N,C,Q,G,H,I,L,M,F,P,S,T,W,Y;
V313A,R,N,D,C,Q,E,G,H,I,L,K,M,F,P,S,T,W,Y;
S320R,N,D,C,Q,E,G,H,I,L,K,M,F,P,T,W,Y,V;
T322R,N,D,C,Q,E,G,H,L,K,M,F,P,S,W,Y,V;
F323A,R,N,D,C,Q,E,G,I,L,K,M,P,S,T,W,Y,V;
D325A,R,C,Q,E,G,H,I,L,K,M,F,P,S,T,W,Y,V;
N326A,R,C,Q,E,G,M,P,S,T,W;
H327A,R,C,G,I,L,K,M,P,S,T,W,Y,V;
T329A,R,N,D,C,Q,E,G,H,I,L,K,M,F,P,W,Y,V;
P331N,D,C,Q,E,G,H,I,L,M,F,S,T,W,Y,V;
V339A,R,N,C,Q,E,G,H,I,L,K,M,F,P,S,T,W,Y;
F343A,R,N,D,C,Q,E,G,H,I,L,K,M,P,S,T,Y,V;
K344A,R,N,D,C,Q,E,G,H,I,L,M,F,P,S,T,W,Y,V;
L346A,R,N,D,Q,E,G,H,I,K,M,F,P,S,T,W,Y,V;
A347R,N,D,C,Q,E,G,H,I,L,K,M,F,P,S,T,W,Y,V;
A349R,N,D,Q,E,G,H,I,L,K,M,F,P,S,T,W,Y,V;
F350A,R,N,C,Q,G,H,I,L,K,M,P,S,T,Y,V;
P359R,N,D,C,Q,E,G,H,I,L,K,M,F,S,T,W,Y,V;
Q360N,D,G,H,I,L,M,F,P,S,T,W,Y,V;
T369A,R,N,D,C,Q,E,G,H,I,L,K,M,F,P,S,W,Y,V;
I377A,R,N,D,C,Q,E,G,H,L,K,M,F,P,S,T,W,Y,V;
L380A,R,N,D,C,Q,E,G,H,K,P,S,W,Y,V;
I387A,R,N,D,C,Q,E,G,H,L,K,M,P,S,T,W,Y,V;
V409N,C,Q,E,G,H,M,P,S,T,W,Y;
G410A,R,N,D,C,Q,E,H,I,L,K,M,F,P,S,T,W,Y,V;
W411A,R,N,D,C,Q,E,G,H,I,L,K,M,F,P,S,T,Y,V;
T412R,N,C,Q,E,G,H,I,L,K,M,F,P,S,W,Y,V;
G423A,R,N,D,C,Q,E,H,I,L,K,M,F,P,S,T,W,Y,V;
L424A,R,N,D,C,Q,E,G,H,I,K,M,F,P,S,T,W,Y,V;
A426R,N,D,C,Q,E,G,H,I,L,K,M,F,P,S,T,W,Y,V;
L427A,R,N,D,C,Q,E,G,H,K,M,P,S,T,Y,V;
I428A,N,D,Q,E,G,H,M,F,P,S,W,Y,V;
T429A,R,N,D,C,Q,E,G,H,I,L,K,M,F,P,S,W,Y,V;
D430A,R,C,Q,E,G,H,I,L,K,M,F,P,S,T,W,Y,V;
M438C;
V440R,N,D,C,Q,E,G,H,I,L,K,M,F,P,S,T,W,Y;
G441A,R,N,D,C,Q,E,H,I,L,K,M,F,P,S,T,W,Y,V;
W449A,R,N,D,C,Q,E,G,H,I,L,K,M,F,P,S,T,Y,V;
I462A,R,N,D,C,Q,E,G,H,L,K,M,F,P,S,T,W,Y,V;
V472A,R,N,D,C,Q,E,G,H,I,L,K,M,F,P,S,T,W,Y;
V477A,R,N,D,C,Q,E,G,H,I,L,K,M,F,P,S,T,W,Y;
I479A,R,N,D,Q,E,G,H,L,K,M,F,P,S,W,Y,V;
Y480A,R,D,C,G,K,M,P,W;
V481A,R,N,D,C,Q,E,G,H,K,M,P,S,T,Y.
A1R,N,D,C,Q,E,G,H,I,L,K,M,F,P,S,T,W,Y;
N2R,D,C,Q,E,G,H,I,L,K,M,F,S,T,W,Y,V;
L3A,R,N,D,C,Q,E,G,H,I,K,M,F,P,S,T,W,Y;
N4A,R,D,C,Q,E,G,H,I,L,K,M,F,P,S,T,W,Y,V;
W13R,N,D,C,Q,E,G,H,K,M,P,S,T;
Y14A,R,D,C,G,K,M,P,W;
P16R,N,D,C,Q,E,G,H,I,L,K,M,F,S,T,W,Y,V;
N17A,R,D,C,Q,E,G,H,I,L,K,M,F,P,S,T,W,Y,V;
D18A,R,N,C,Q,E,G,H,I,L,K,M,F,P,S,T,W,Y,V;
Q20A,R,N,D,C,E,G,H,I,L,K,M,F,P,S,T,W,Y,V;
R23A,N,D,C,Q,E,G,H,I,L,M,F,P,S,W,Y,V;
R24A,N,D,C,Q,E,G,H,I,L,K,M,F,P,S,T,W,Y,V;
Q26A,D,C,E,G,H,I,L,M,F,P,S,T,W,V;
E34A,R,N,C,Q,G,H,I,L,K,M,F,P,T,W,Y,V;
H35A,R,N,D,C,Q,E,G,K,M,F,P,S,T,W,Y,V;
T49A,C,G,H,P;
S50A,R,N,C,Q,E,G,H,K,M,F,P,W;
Q51A,N,D,C,E,G,H,I,L,M,F,P,S,T,W,Y,V;
A52R,D,C,Q,E,G,H,K,P;
D53A,C,G,H,K,M,P;
L61A,R,N,D,C,Q,E,G,H,I,K,M,P,S,T,Y;
Y62A,R,D,C,G,K,M,P;
F67A,R,N,D,C,Q,E,G,H,I,L,K,M,P,S,T,Y,V;
H68A,R,D,C,E,G,I,L,K,M,F,P,S,T,W,Y,V;
V73A,R,N,D,C,Q,E,G,H,K,M,P,S,T,W,Y;
Q84A,R,N,D,C,G,H,I,L,K,M,F,P,S,T,W,Y,V;
S85A,R,N,C,E,G,H,I,L,K,M,F,P,T,W,Y,V;
K88A,R,N,D,C,E,G,H,I,L,M,F,P,S,T,W,Y,V;
H91A,R,N,D,C,Q,E,G,I,L,K,M,F,P,S,T,W,Y,V;
S92A,R,N,D,C,Q,E,G,H,I,L,M,F,P,T,W,Y,V;
N96A,R,D,C,E,G,H,I,L,K,M,F,P,S,T,W,Y,V;
K106A,N,D,C,Q,E,G,H,I,L,M,P,S,T,Y,V;
G108R,N,D,C,Q,E,H,I,L,K,M,F,P,S,T,W,Y,V;
D114A,N,C,Q,E,G,H,K,F,P,S,T,W,Y;
T116A,R,D,C,Q,E,G,H,I,L,M,F,P,S,W,Y,V;
E119A,R,N,D,Q,G,H,I,L,K,M,F,P,S,T,W,Y,V;
D121A,R,C,Q,E,G,H,I,L,K,M,F,P,S,T,W,Y,V;
P122R,N,Q,G,H,I,L,M,F,S,T,W,Y,V;
A123N,D,C,Q,E,G,H,I,L,M,F,P,S,T,W,Y,V;
D124N,Q,G,H,I,L,M,F,P,S,T,W,Y,V;
R125N,Q,E,G,I,K,M,F,S,T,W,Y;
N126Q,G,H,I,L,M,F,P,S,T,W,Y,V;
R127A,N,D,E,G,H,I,L,K,M,F,P,S,T,W,Y,V;
V128A,R,N,D,C,Q,G,H,I,L,K,M,F,P,S,W,Y;
I129A,R,N,D,C,Q,E,G,H,L,K,M,F,P,S,W,Y,V;
S130A,R,N,D,Q,E,G,H,I,L,K,M,F,P,W,Y,V;
G131A,R,N,D,C,Q,H,I,L,K,M,F,P,S,T,W,Y,V;
E132R,N,D,C,Q,G,H,I,L,K,M,F,S,W,Y;
H133R,N,D,C,M,T,W,V;
L134A,N,D,C,E,G,H,I,K,M,F,P,S,T,W,Y,V;
K136A,R,N,D,C,E,G,H,I,L,M,F,P,S,T,W,Y,V;
W138R,N,D,Q,E,G,I,K,M,P,S,T,V;
G145A,R,N,D,C,Q,E,H,I,L,K,M,P,S,T,Y,V;
G147A,R,N,D,C,Q,E,H,I,L,K,M,P,S,T,W,Y,V;
S148A,R,D,C,Q,E,G,H,I,L,K,M,F,P,T,W,Y,V;
T149A,R,N,D,C,Q,E,G,H,L,K,M,F,P,S,W,Y,V;
Y150A,D,C,G,M,P,W;
D152A,R,N,C,Q,E,G,H,I,L,K,M,F,P,T,W,Y,V;

F153A,R,N,D,C,Q,E,G,H,I,L,M,P,S,T,W,Y,V;
K154A,R,N,D,C,Q,E,G,H,I,L,M,F,P,S,T,W,Y,V;
W155A,R,N,D,C,Q,E,G,H,I,L,K,M,F,P,S,T,Y,V;
H156A,C,Q,E,G,I,L,M,F,P,S,T,W,V;
W157R,I,L,M,F,P,S,T,Y,V;
Y158R,M,P,W;
D164R,I,L,M,F,P,S,T,W,Y,V;
W165A,N,D,C,Q,E,H,I,L,K,M,F,P,S,T,Y,V;
E167A,R,N,D,C,Q,G,H,I,L,K,M,F,P,S,T,W,Y,V;
S168A,R,N,D,C,Q,E,G,H,I,L,K,M,F,T,W,V;
R169A,N,D,C,Q,E,G,H,M,P,S,W,Y,V;
K170A,R,N,D,C,E,G,H,I,L,M,F,P,S,T,W,Y,V;
L171A,R,N,D,C,Q,E,G,H,K,M,P,S,T,W,Y,V;
N172A,D,C,Q,E,G,I,L,M,F,P,T,W,Y,V;
R173A,N,D,C,Q,E,G,H,M,P,S,W,Y,V;
K176A,N,D,C,Q,E,G,H,I,L,M,F,P,S,T,W,Y,V;
G179D,C,Q,E,H,I,L,K,M,F,P,W,Y,V;
K180A,G,I,L,M,F,P,W,Y,V;
A181G;
W182A,R,N,D,C,Q,E,G,H,I,L,K,M,F,P,S,T,Y,V;
W184I,L,M,F,P,W,Y,V;
E185R,I,L,M,F,P,S,T,W,Y,V;
N188A,R,Q,G,H,L,M,F,W,V;
E189A,R,N,G,H,I,L,M,F,P,S,T,W,Y,V;
G191A,R,N,Q,H,I,L,M,F,P,S,T,W,Y,V;
Y193A,R,G,M,P,W;
L196A,N,Q,G,H,I,M,P,S,T,W,V;
Y198A,R,G,M,P,W;
D204R,L,M,F,P,T,W,Y,V;
H205A,G,I,L,M,F,P,W,Y,V;
P206R,N,D,C,Q,E,G,H,I,L,K,M,F,S,T,W,Y,V;
A209R,P,S,W,Y;
A210R,N,D,C,Q,E,G,H,I,L,K,M,F,P,W,Y,V;
R214A,D,C,Q,E,G,I,L,M,F,P,S,T,Y,V;
T217A,R,N,D,C,Q,G,H,I,L,M,F,P,S,W.Y;
W218A,R,N,D,C,Q,E,G,H,I,L,K,M,F,P,S,T,Y,V;
N221A,R,D,C,Q,E,G,H,I,L,K,M,F,P,S,T,W,Y,V;
E222A,R,N,D,C,G,H,I,L,K,M,F,P,S,W,Y,V;
K234A,D,C,G,H,I,M,F,P,S,T,W,Y,V;
H235A,R,N,D,C,Q,E,G,I,L,K,M,F,P,S,T,W,Y,V;
K237A,G,H,I,L,M,F,W,Y,V;
S239G,H,I,L,M,F,P,T,Y,V;
R242G,I,L,M,F,S,T,W,Y,V;
N246A,R,D,C,Q,E,G,H,I,L,K,M,F,P,S,T,W,Y,V;
H247R,N,D,C,Q,E,G,I,L,K,M,F,P,S,T,W,V;
R249A,N,D,C,Q,E,G,H,I,L,K,M,F,P,S,T,W,Y,V;
E250A,R,N,D,C,H,I,L,K,M,P,T,W,Y,V;
K251R,N,D,C,E,G,H,I,L,M,F,P,S,T,W,Y,V;
T252A,R,N,D,C,Q,E,G,H,I,L,K,M,F,P,S,W,Y,V;
G253R,D,C,Q,E,H,I,L,K,M,F,P,S,T,W,Y;
K254A,R,N,D,C,Q,E,G,H,I,L,M,F,P,S,T,W,Y,V;
E255A,R,D,C,G,H,I,L,K,M,F,S,T,W,Y,V;
F257A,R,N,D,C,Q,E,G,H,I,L,K,M,P,S,T,W,Y,V;
E261A,R,N,D,C,Q,G,H,I,L,K,M,F,P,S,T,W,Y,V;
W263A,R,N,D,C,Q,E,G,I,L,K,M,F,P,S,T,Y,V;
N265C,Q,E,H,I,L,M,F,P,W;
D266A,R,N,C,Q,E,G,H,I,L,K,M,F,P,S,T,W,Y,V;
L267A,R,N,D,C,Q,E,G,H,K,P,S,T,W,Y,V;
G268A,R,N,D,C,Q,E,H,I,L,K,M,F,P,S,T,W,Y,V;
A269N,C,Q,G,H,I,L,M,F,P,S,T,W,Y,V;
E271A,R,N,D,C,Q,G,H,I,L,K,M,F,P,S,T,W,Y,V;
N272A,R,D,C,Q,E,G,H,I,L,K,M,F,P,S,T,W,Y,V;
N275A,R,D,C,Q,E,G,H,I,L,K,M,F,P,S,W,Y,V;
K276A,R,N,D,C,Q,E,G,H,I,L,M,F,P,S,T,W,Y,V;
N278A,R,D,C,Q,E,G,H,I,L,K,M,F,P,S,T,W,Y,V;
N280A,R,D,C,E,G,H,I,L,K,M,F,P,W,Y,V;
Y290W;
Q291A,R,N,G,H,I,L,M,F,P,S,T,W,Y,V;
H293A,R,N,G,I,L,M,P,S,T,W,V;
A294R,N,Q,G,H,I,L,M,F,P,S,T,W,Y;
T297A,G,H,I,L,M,F,P,W,Y,V;
Q298G,H,I,L,M,F,P,S,T,W,Y,V;
G299A,H,M,P,S,T;
G300A,C,H,I,L,M,F,P,T,W,Y,V;
G301N,Q,H,I,L,M,F,P,S,T,W,Y,V;
Y302R,M,P,W;
D303R,I,L,M,F,P,S,T,W,Y,V;
R305G,I,L,M,F,P,S,T,W,Y,V;
K306Q,G,H,I,L,M,F,P,S,T,W,Y,V;
L308A,R,N,D,C,Q,E,G,H,I,K,M,F,P,S,T,W,Y,V;
N309Q,G,H,I,L,M,F,P,S,T,W,Y,V;
G310A,R,N,C,Q,E,H,I,L,K,M,F,P,S,T,W,Y,V;
S314A,D,C,E,G,I,L,M,F,P,W,Y,V;
K315A,N,C,Q,E,G,H,I,L,M,F,P,S,T,W,Y,V;
H316A,R,N,D,C,Q,E,G,I,L,K,M,F,P,S,T,W,V;
P317R,N,D,C,Q,E,G,H,I,L,K,M,F,S,T,W,Y,V;
L318A,R,N,D,C,Q,E,G,H,I,K,P,S,W,Y,V;
K319A,R,N,D,C,Q,E,G,H,I,L,M,F,P,S,T,W,Y,V;
D328A,R,N,C,Q,E,G,H,I,L,K,M,F,P,S,T,W,Y,V;
G332A,R,N,C,Q,E,H,I,L,K,M,F,P,S,T,W,Y,V;
Q333A,N,D,C,G,I,M,F,P,S,T,Y,V;
S334R,N,C,Q,E,G,H,K,M,F,P,W,Y;
L335R,D,C,Q,E,H,I,K,M,F,P,W,Y,V;
E336A,N,D,C,Q,G,H,I,L,M,F,P,S,T,W,Y,V;
S337A,R,N,C,Q,E,G,H,I,L,M,F,P,T,W,Y,V;
T338A,R,N,C,Q,G,H,I,L,K,M,F,P,S,W,Y,V;
Q340I,L,M,F,P,S,T,W,Y,V;
T341A,R,D,C,G,H,I,L,K,M,F,W,Y,V;
W342R,I,L,M,F,P,S,T,Y,V;
P345R,N,D,C,Q,E,G,H,I,L,K,M,F,T,W,Y,V;
E355A,R,N,D,C,Q,G,H,I,L,K,M,F,P,S,T,W,Y,V;
Y358A,R,D,C,G,K,M,P,W;
Y363A,R,D,C,G,K,M,P,W;
K370A,R,N,D,C,Q,E,G,H,I,L,M,F,P,S,T,W,Y,V;
G371A,N,C,Q,E,H,I,L,K,M,F,P,S,T,W,Y,V;
S373A,R,N,D,C,Q,E,G,H,I,L,K,M,F,T,W,Y,V;
Q374A,N,D,C,E,G,H,I,L,K,M,F,S,T,W,Y,V;
R375A,N,D,C,Q,G,H,I,L,K,M,F,P,S,T,W,V;
E376A,R,N,D,C,Q,G,H,I,L,M,F,P,S,T,W,Y,V;
P378R,N,D,C,Q,E,G,H,I,L,K,M,F,S,T,W,Y,V;
A379R,N,D,C,Q,E,G,H,I,L,K,M,F,P,T,W,Y,V;
K381A,R,N,D,C,Q,E,G,H,I,L,M,F,P,S,T,W,Y,V;
K389A,D,C,G,H,M,F,P,S,T,W,Y,V;
Q393A,N,C,E,G,H,I,L,K,M,F,P,S,T,W,Y,V;
Y394A,R,D,C,G,K,M,P,W;
Y396A,R,D,C,G,K,M,P,W;
A398R,N,D,C,Q,E,G,H,I,L,M,F,W,Y,V;
Y402R,C,G,K,M,P,W;
F403A,R,N,Q,G,H,I,L,M,P,S,T,W,Y,V;
D404R,I,L,M,F,P,S,T,W,Y,V;
H405R,G,I,L,M,F,P,W,Y,V;
H406A,R,G,I,M,F,P,Y,V;
D407A,R,Q,G,H,I,L,M,F,P,S,T,W,Y,V;
I408A,R,N,D,C,Q,E,G,H,K,M,P,S,T,W,Y,V;
R413A,N,D,C,Q,E,G,H,I,L,K,M,F,P,S,T,W,Y,V;
E414A,R,N,D,C,Q,G,H,I,L,K,M,F,P,S,T,W,Y,V;
G415A,R,N,D,C,Q,E,H,I,L,K,M,F,P,S,T,W,Y,V;
D416A,R,N,C,Q,E,G,H,I,L,K,M,F,P,S,T,W,Y,V;
S417A,R,N,D,C,Q,E,G,H,I,L,K,M,F,P,W,Y,V;
S418A,R,N,D,C,Q,E,G,H,I,L,K,M,F,P,T,W,Y,V;
V419A,R,N,D,C,Q,E,G,H,I,L,M,F,P,S,T,W,Y;
A420N,D,C,E,G,H,I,L,K,M,F,S,T,W,Y,V;
N421A,R,D,C,Q,E,H,I,L,K,M,F,P,S,T,W,Y,V;
S422A,R,N,D,C,Q,E,G,H,I,L,K,M,F,P,T,W,Y,V;

G431A,R,N,Q,H,I,L,M,F,P,S,T,W,Y,V;
P432G,H,I,L,M,F,S,T,W,Y,V;
G433A,R,N,Q,H,I,L,M,F,P,S,T,W,Y,V;
G434A,R,N,Q,H,I,L,M,F,P,S,T,W,Y,V;
A435Q,G,H,I,L,M,F,P,T,W,Y,V;
K436A,R,N,D,C,Q,E,G,H,I,L,M,F,P,S,T,W,Y,V;
R437A,N,D,C,Q,E,G,H,I,L,K,M,F,P,S,T,W,Y,V;
Y439A,R,D,C,G,K,M,P,W;
R442A,N,D,C,E,G,H,I,L,M,F,P,S,T,W,Y,V;
Q443A,R,N,D,C,E,G,H,I,L,M,F,P,S,T,W,Y,V;
N444A,C,G,H,I,L,M,F,P,S,T,W,Y,V;
A445R,N,D,C,Q,E,G,H,I,L,K,M,F,P,S,T,W,Y,V;
G446A,R,N,D,C,Q,E,H,I,L,K,M,F,P,S,T,W,Y,V;
E447A,N,D,C,G,H,I,L,M,F,P,S,T,W,Y,V;
T448A,R,N,D,C,Q,E,G,H,I,L,K,M,F,P,S,W,Y,V;
H450A,N,D,C,Q,E,G,I,L,K,M,F,P,S,T,W,V;
G454A,R,N,D,C,Q,E,H,I,L,K,M,F,P,S,T,W,Y,V;
N455A,R,C,Q,G,H,I,L,K,M,F,P,S,T,W,Y,V;
R456A,D,C,E,G,H,I,L,M,F,P,S,T,W,Y,V;
S457A,R,N,D,C,Q,E,G,H,I,L,K,M,F,W,Y,V;
E458A,R,N,C,Q,G,H,I,L,K,M,F,P,S,T,W,Y,V;
P459R,N,D,C,Q,E,G,H,I,L,K,M,F,S,W,Y,V;
V460A,R,N,D,C,Q,E,G,H,I,L,K,M,F,P,S,T,W,Y;
V461A,R,N,D,C,Q,E,G,H,I,L,M,F,P,S,W,Y;
N463A,R,D,C,Q,E,H,I,L,K,M,F,P,S,T,W,Y,V;
S464A,R,N,D,C,Q,E,G,H,I,L,K,M,F,P,T,W,Y,V;
E465A,R,N,C,Q,G,H,I,L,K,M,F,P,S,T,W,Y,V;
W467A,R,N,D,C,Q,E,G,H,I,L,K,M,F,P,S,T,Y,V;
E469A,R,N,D,C,Q,G,H,I,L,K,M,F,P,S,T,W,Y,V;
N473Q,G,H,I,L,M,F,P,S,T,W,Y,V;
G474A,R,H,I,L,M,F,P,W,Y,V;
G475A,N,Q,H,I,L,M,F,P,S,T,W,Y,V;
S476G,H,I,L,M,F,P,T,W,Y,V;
Q482A,N,D,C,G,H,I,L,M,F,S,T,W,Y,V;
R483A,N,D,C,Q,E,G,H,I,L,M,F,P,S,T,W,Y,V.

The variants are tested for altered substrate specificity, substrate binding, substrate cleavage pattern, thermal stability, pH activity profile, pH stability profile, stability towards oxidation, $Ca^{2+}$ dependency, reduced LAS sensitivity, reduced and increased pI and improved wash performance, and specific activity as described in the "Materials & Methods" section above.

Example 2

Construction of Variants of the Invention and Determination of Altered Properties The below listed variants are constructed as described in EXAMPLE 1 of WO 00/37626 (from Novozymes A/S) in the parent *Bacillus licheniformis* alpha-amylase shown in SEQ ID NO: 8. The alterations of the variants are, as specified in the list below, insertion of an amino acid downstream of the amino acid which occupies the position, or deletion of the amino acid which occupies the position.
A1 insertion;
L3 insertion;
N4 insertion;
N17 insertion;
D18 insertion;
Q20 insertion;
R23 insertion;
R24 insertion;
D28 insertion;
Y56 insertion;
L61 insertion or deletion;
Y62 insertion;
F67 insertion or deletion;
H68 insertion;
K80 insertion or deletion;
G81 insertion or deletion;
Q84 insertion;
S85 insertion;
H91 insertion or deletion;
S92 insertion or deletion;
K106 insertion or deletion;
D110 insertion or deletion;
D114 deletion;
E119 insertion or deletion;
D121 insertion;
P122 insertion;
A123 insertion;
D124 insertion;
R125 insertion;
N126 insertion;
R127 insertion;
I129 insertion;
G131 insertion;
L134 insertion;
K136 insertion;
N172 insertion;
E185 insertion;
L196 insertion or deletion;
P206 insertion or deletion;
T217 insertion;
W218 insertion;
D231 insertion or deletion;
A232 insertion or deletion;
H235 insertion or deletion;
N246 insertion;
H247 insertion;
R249 insertion;
K251 insertion;
F257 insertion or deletion;
N278 insertion;
G310 insertion or deletion;
H316 insertion;
P317 insertion;
D328 insertion or deletion;
G332 insertion or deletion;
E355 insertion or deletion;
Y358 insertion;
Y363 insertion;
Y367 insertion;
K370 insertion;
S373 insertion;
R375 insertion;
E376 insertion;
K381 insertion;
H382 insertion;
R391 insertion or deletion;
Y396 insertion;
R413 insertion or deletion;
E414 insertion or deletion;
G415 insertion or deletion;
D416 insertion;
S417 insertion;
S418 insertion;
V419 insertion;
A420 insertion;
N421 insertion;
S422 insertion or deletion;
Y439 insertion;
A445 insertion or deletion;

G446 insertion or deletion;
T448 insertion or deletion;
H450 insertion;
G454 insertion or deletion;
N455 insertion;
E458 insertion;
P459 insertion;
V460 insertion;
V461 insertion;
N463 insertion;
S464 insertion;
E465 insertion;
W467 insertion;
L7 insertion or deletion;
M8 insertion;
Y10 insertion;
F11 insertion;
E12 insertion or deletion;
M15 insertion;
G19 insertion;
H21 insertion;
W22 insertion;
L25 insertion;
V40 insertion or deletion;
W41 insertion;
P43 insertion or deletion;
P44 insertion or deletion;
Y46 insertion;
G55 insertion;
Y59 insertion;
Y77 insertion;
G78 insertion or deletion;
L90 insertion or deletion;
I95 insertion;
V97 insertion;
Y98 insertion;
G99 insertion;
D100 insertion;
V101 insertion;
V102 insertion;
H105 insertion or deletion;
A109 insertion or deletion;
V15 insertion or deletion;
V118 insertion or deletion;
I135 insertion;
T139 insertion or deletion;
F141 insertion or deletion;
Y195 insertion;
V208 insertion or deletion;
W215 insertion;
Y219 insertion;
I236 insertion or deletion;
F238 insertion or deletion;
F240 insertion or deletion;
W244 insertion;
V248 insertion;
M256 insertion;
T258 insertion or deletion;
V259 insertion or deletion;
V312 insertion or deletion;
V313 insertion or deletion;
S320 insertion;
T322 insertion or deletion;
F323 insertion or deletion;
D325 insertion or deletion;
N326 insertion;
H327 insertion or deletion;
Q330 insertion or deletion;
P331 insertion or deletion;
Y348 insertion;
A349 insertion or deletion;
F350 insertion or deletion;
P359 insertion or deletion;
Q360 insertion;
D365 insertion or deletion;
M366 insertion;
T369 insertion;
I377 insertion;
I384 insertion or deletion;
L388 insertion or deletion;
G423 insertion or deletion;
L424 insertion or deletion;
M438 insertion;
G441 insertion or deletion;
W449 insertion;
I462 insertion;
I479 insertion or deletion;
Y480 insertion;
V481 insertion or deletion.

The variants are tested for altered substrate specificity, substrate binding, substrate cleavage pattern, thermal stability, pH activity profile, pH stability profile, stability towards oxidation, $Ca^{2+}$ dependency, reduced and increased pI and improved wash performance, specific activity as described in the "Materials & Methods" section above.

The invention claimed is:

1. An isolated variant alpha-amylase, wherein the variant alpha-amylase has at least 90% sequence identity to SEQ ID NO: 2, 4, 6, 8, 10, 12, or 13 and wherein the variant comprises an alteration at one or more positions corresponding to positions of SEQ ID NO:8 selected from the group consisting of: 79, 86, 112, 113, 368, 390, 470, and 478,
wherein
the alteration(s) are a substitution of the amino acid which occupies the position with a different amino acid; and
the variant has alpha-amylase activity.

2. The variant of claim 1, wherein the variant has at least 95% sequence identity to SEQ ID NO: 2, 4, 6, 8, 10, 12, or 13.

3. The variant of claim 1, wherein the variant has at least 96% sequence identity to SEQ ID NO: 2, 4, 6, 8, 10, 12, or 13.

4. The variant of claim 1, wherein the variant has at least 97% sequence identity to SEQ ID NO: 2, 4, 6, 8, 10, 12, or 13.

5. The variant of claim 1, wherein the variant has at least 98% sequence identity to SEQ ID NO: 2, 4, 6, 8, 10, 12, or 13.

6. The variant of claim 1, wherein the variant has at least 99% sequence identity to SEQ ID NO: 2, 4, 6, 8, 10, 12, or 13.

7. A detergent composition comprising the alpha-amylase variant according to claim 1 and a surfactant.

8. The detergent composition of claim 7, which additionally comprises another enzyme selected from the group consisting of a protease, a lipase, a peroxidase, another amylolytic enzyme, a glucoamylase, a maltogenic amylase, a CGTase, a mannanase, a cutinase, a laccase and a cellulase.

9. A recombinant variant alpha-amylase, wherein the variant alpha-amylase has at least 90% sequence identity to SEQ ID NO: 2, 4, 6, 8, 10, 12 or 13, wherein said variant comprises a substitution at one or more positions corresponding to positions of SEQ ID NO: 8 selected from the group consisting of 79, 86, 112, 113, 368, 390, 470, and 478, wherein the variant has alpha-amylase activity.

10. The variant alpha-amylase in accordance with claim 9, wherein the variant comprises a substitution at position 79.

11. The variant alpha-amylase in accordance with claim 9, wherein the variant comprises a substitution at position 86.

12. The variant alpha-amylase in accordance with claim 9, wherein the variant comprises a substitution at position 112.

13. The variant alpha-amylase in accordance with claim 9, wherein the variant comprises a substitution at position 113.

14. The variant alpha-amylase in accordance with claim 9, wherein the variant comprises a substitution at position 368.

15. The variant alpha-amylase in accordance with claim 9, wherein the variant comprises a substitution at position 390.

16. The variant alpha-amylase in accordance with claim 9, wherein the variant comprises a substitution at position 470.

17. The variant alpha-amylase in accordance with claim 9, wherein the variant comprises a substitution at position 478.

18. The variant in according with claim 9, wherein the variant has at least 99% sequence identity to SEQ ID NO: 2, 4, 6, 8, 10, 12 or 13.

19. The variant of claim 9, wherein the variant has at least 99% sequence identity to SEQ ID NO: 2.

20. The variant of claim 9, wherein the variant has at least 99% sequence identity to SEQ ID NO: 4.

21. The variant of claim 9, wherein the variant has at least 99% sequence identity to SEQ ID NO: 6.

22. The variant of claim 9, wherein the variant has at least 99% sequence identity to SEQ ID NO: 8.

23. The variant of claim 9, wherein the variant has at least 99% sequence identity to SEQ ID NO: 10.

24. The variant of claim 9, wherein the variant has at least 99% sequence identity to SEQ ID NO: 12.

25. The variant of claim 9, wherein the variant has at least 99% sequence identity to SEQ ID NO: 13.

\* \* \* \* \*

SEQUENCE LISTING

```
<160> NUMBER OF SEQ ID NOS: 13

<210> SEQ ID NO 1
<211> LENGTH: 1455
<212> TYPE: DNA
<213> ORGANISM: Unknown
<220> FEATURE:
<223> OTHER INFORMATION: Bacillus species
<220> FEATURE:
<221> NAME/KEY: CDS
<222> LOCATION: (1)..(1455)
<223> OTHER INFORMATION: SP690

<400> SEQUENCE: 1 cat cat aat gga aca aat ggt act atg atg caa tat ttc gaa tgg tat      48
His His Asn Gly Thr Asn Gly Thr Met Met Gln Tyr Phe Glu Trp Tyr
```

```
            1               5               10              15 ttg cca aat gac ggg aat cat tgg aac agg ttg agg gat gac gca gct      96
Leu Pro Asn Asp Gly Asn His Trp Asn Arg Leu Arg Asp Asp Ala Ala
                20              25              30 aac tta aag agt aaa ggg ata aca gct gta tgg atc cca cct gca tgg      144
Asn Leu Lys Ser Lys Gly Ile Thr Ala Val Trp Ile Pro Pro Ala Trp
        35              40              45 aag ggg act tcc cag aat gat gta ggt tat gga gcc tat gat tta tat      192
Lys Gly Thr Ser Gln Asn Asp Val Gly Tyr Gly Ala Tyr Asp Leu Tyr
    50              55              60 gat ctt gga gag ttt aac cag aag ggg acg gtt cgt aca aaa tat gga      240
Asp Leu Gly Glu Phe Asn Gln Lys Gly Thr Val Arg Thr Lys Tyr Gly
65              70              75              80 aca cgc aac cag cta cag gct gcg gtg acc tct tta aaa aat aac ggc      288
Thr Arg Asn Gln Leu Gln Ala Ala Val Thr Ser Leu Lys Asn Asn Gly
                85              90              95 att cag gta tat ggt gat gtc gtc atg aat cat aaa ggt gga gca gat      336
Ile Gln Val Tyr Gly Asp Val Val Met Asn His Lys Gly Gly Ala Asp
            100             105             110 ggt acg gaa att gta aat gcg gta gaa gtg aat cgg agc aac cga aac      384
Gly Thr Glu Ile Val Asn Ala Val Glu Val Asn Arg Ser Asn Arg Asn
        115             120             125 cag gaa acc tca gga gag tat gca ata gaa gcg tgg aca aag ttt gat      432
Gln Glu Thr Ser Gly Glu Tyr Ala Ile Glu Ala Trp Thr Lys Phe Asp
    130             135             140 ttt cct gga aga gga aat aac cat tcc agc ttt aag tgg cgc tgg tat      480
Phe Pro Gly Arg Gly Asn Asn His Ser Ser Phe Lys Trp Arg Trp Tyr
145             150             155             160 cat ttt gat ggg aca gat tgg gat cag tca cgc cag ctt caa aac aaa      528
His Phe Asp Gly Thr Asp Trp Asp Gln Ser Arg Gln Leu Gln Asn Lys
                165             170             175 ata tat aaa ttc agg gga aca ggc aag gcc tgg gac tgg gaa gtc gat      576
Ile Tyr Lys Phe Arg Gly Thr Gly Lys Ala Trp Asp Trp Glu Val Asp
            180             185             190 aca gag aat ggc aac tat gac tat ctt atg tat gca gac gtg gat atg      624
Thr Glu Asn Gly Asn Tyr Asp Tyr Leu Met Tyr Ala Asp Val Asp Met
        195             200             205 gat cac cca gaa gta ata cat gaa ctt aga aac tgg gga gtg tgg tat      672
Asp His Pro Glu Val Ile His Glu Leu Arg Asn Trp Gly Val Trp Tyr
    210             215             220 acg aat aca ctg aac ctt gat gga ttt aga ata gat gca gtg aaa cat      720
Thr Asn Thr Leu Asn Leu Asp Gly Phe Arg Ile Asp Ala Val Lys His
225             230             235             240 ata aaa tat agc ttt acg aga gat tgg ctt aca cat gtg cgt aac acc      768
Ile Lys Tyr Ser Phe Thr Arg Asp Trp Leu Thr His Val Arg Asn Thr
                245             250             255 aca ggt aaa cca atg ttt gca gtg gct gag ttt tgg aaa aat gac ctt      816
Thr Gly Lys Pro Met Phe Ala Val Ala Glu Phe Trp Lys Asn Asp Leu
            260             265             270 ggt gca att gaa aac tat ttg aat aaa aca agt tgg aat cac tcg gtg      864
Gly Ala Ile Glu Asn Tyr Leu Asn Lys Thr Ser Trp Asn His Ser Val
        275             280             285 ttt gat gtt cct ctc cac tat aat ttg tac aat gca tct aat agc ggt      912
Phe Asp Val Pro Leu His Tyr Asn Leu Tyr Asn Ala Ser Asn Ser Gly
    290             295             300 ggt tat tat gat atg aga aat att tta aat ggt tct gtg gtg caa aaa      960
Gly Tyr Tyr Asp Met Arg Asn Ile Leu Asn Gly Ser Val Val Gln Lys
305             310             315             320 cat cca aca cat gcc gtt act ttt gtt gat aac cat gat tct cag ccc      1008
His Pro Thr His Ala Val Thr Phe Val Asp Asn His Asp Ser Gln Pro
```

```
                  325                 330                 335
ggg gaa gca ttg gaa tcc ttt gtt caa caa tgg ttt aaa cca ctt gca      1056
Gly Glu Ala Leu Glu Ser Phe Val Gln Gln Trp Phe Lys Pro Leu Ala
            340                 345                 350 tat gca ttg gtt ctg aca agg gaa caa ggt tat cct tcc gta ttt tat      1104
Tyr Ala Leu Val Leu Thr Arg Glu Gln Gly Tyr Pro Ser Val Phe Tyr
        355                 360                 365 ggg gat tac tac ggt atc cca acc cat ggt gtt ccg gct atg aaa tct      1152
Gly Asp Tyr Tyr Gly Ile Pro Thr His Gly Val Pro Ala Met Lys Ser
    370                 375                 380 aaa ata gac cct ctt ctg cag gca cgt caa act ttt gcc tat ggt acg      1200
Lys Ile Asp Pro Leu Leu Gln Ala Arg Gln Thr Phe Ala Tyr Gly Thr
385                 390                 395                 400 cag cat gat tac ttt gat cat cat gat att atc ggt tgg aca aga gag      1248
Gln His Asp Tyr Phe Asp His His Asp Ile Ile Gly Trp Thr Arg Glu
                405                 410                 415 gga aat agc tcc cat cca aat tca ggc ctt gcc acc att atg tca gat      1296
Gly Asn Ser Ser His Pro Asn Ser Gly Leu Ala Thr Ile Met Ser Asp
            420                 425                 430 ggt cca ggt ggt aac aaa tgg atg tat gtg ggg aaa aat aaa gcg gga      1344
Gly Pro Gly Gly Asn Lys Trp Met Tyr Val Gly Lys Asn Lys Ala Gly
        435                 440                 445 caa gtt tgg aga gat att acc gga aat agg aca ggc acc gtc aca att      1392
Gln Val Trp Arg Asp Ile Thr Gly Asn Arg Thr Gly Thr Val Thr Ile
    450                 455                 460 aat gca gac gga tgg ggt aat ttc tct gtt aat gga ggg tcc gtt tcg      1440
Asn Ala Asp Gly Trp Gly Asn Phe Ser Val Asn Gly Gly Ser Val Ser
465                 470                 475                 480 gtt tgg gtg aag caa                                                  1455
Val Trp Val Lys Gln
                485

<210> SEQ ID NO 2
<211> LENGTH: 485
<212> TYPE: PRT
<213> ORGANISM: Unknown
<220> FEATURE:
<223> OTHER INFORMATION: Bacillus species

<400> SEQUENCE: 2

His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Asp Asp Ala Ala
            20                  25                  30

Asn Leu Lys Ser Lys Gly Ile Thr Ala Val Trp Ile Pro Pro Ala Trp
        35                  40                  45

Lys Gly Thr Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Arg Asn Gln Leu Gln Ala Ala Val Thr Ser Leu Lys Asn Asn Gly
                85                  90                  95

Ile Gln Val Tyr Gly Asp Val Val Met Asn His Lys Gly Gly Ala Asp
            100                 105                 110

Gly Thr Glu Ile Val Asn Ala Val Glu Val Asn Arg Ser Asn Arg Asn
        115                 120                 125

Gln Glu Thr Ser Gly Glu Tyr Ala Ile Glu Ala Trp Thr Lys Phe Asp
    130                 135                 140

Phe Pro Gly Arg Gly Asn Asn His Ser Ser Phe Lys Trp Arg Trp Tyr
```

```
                145                 150                 155                 160
His Phe Asp Gly Thr Asp Trp Asp Gln Ser Arg Gln Leu Gln Asn Lys
                    165                 170                 175

Ile Tyr Lys Phe Arg Gly Thr Gly Lys Ala Trp Asp Trp Glu Val Asp
                    180                 185                 190

Thr Glu Asn Gly Asn Tyr Asp Tyr Leu Met Tyr Ala Asp Val Asp Met
                    195                 200                 205

Asp His Pro Glu Val Ile His Glu Leu Arg Asn Trp Gly Val Trp Tyr
    210                 215                 220

Thr Asn Thr Leu Asn Leu Asp Gly Phe Arg Ile Asp Ala Val Lys His
225                 230                 235                 240

Ile Lys Tyr Ser Phe Thr Arg Asp Trp Leu Thr His Val Arg Asn Thr
                    245                 250                 255

Thr Gly Lys Pro Met Phe Ala Val Ala Glu Phe Trp Lys Asn Asp Leu
                    260                 265                 270

Gly Ala Ile Glu Asn Tyr Leu Asn Lys Thr Ser Trp Asn His Ser Val
                    275                 280                 285

Phe Asp Val Pro Leu His Tyr Asn Leu Tyr Asn Ala Ser Asn Ser Gly
    290                 295                 300

Gly Tyr Tyr Asp Met Arg Asn Ile Leu Asn Gly Ser Val Val Gln Lys
305                 310                 315                 320

His Pro Thr His Ala Val Thr Phe Val Asp Asn His Asp Ser Gln Pro
                    325                 330                 335

Gly Glu Ala Leu Glu Ser Phe Val Gln Gln Trp Phe Lys Pro Leu Ala
                    340                 345                 350

Tyr Ala Leu Val Leu Thr Arg Glu Gln Gly Tyr Pro Ser Val Phe Tyr
                    355                 360                 365

Gly Asp Tyr Tyr Gly Ile Pro Thr His Gly Val Pro Ala Met Lys Ser
    370                 375                 380

Lys Ile Asp Pro Leu Leu Gln Ala Arg Gln Thr Phe Ala Tyr Gly Thr
385                 390                 395                 400

Gln His Asp Tyr Phe Asp His His Asp Ile Ile Gly Trp Thr Arg Glu
                    405                 410                 415

Gly Asn Ser Ser His Pro Asn Ser Gly Leu Ala Thr Ile Met Ser Asp
                    420                 425                 430

Gly Pro Gly Gly Asn Lys Trp Met Tyr Val Gly Lys Asn Lys Ala Gly
                    435                 440                 445

Gln Val Trp Arg Asp Ile Thr Gly Asn Arg Thr Gly Thr Val Thr Ile
    450                 455                 460

Asn Ala Asp Gly Trp Gly Asn Phe Ser Val Asn Gly Gly Ser Val Ser
465                 470                 475                 480

Val Trp Val Lys Gln
                485

<210> SEQ ID NO 3
<211> LENGTH: 1455
<212> TYPE: DNA
<213> ORGANISM: Unknown
<220> FEATURE:
<223> OTHER INFORMATION: Bacillus species
<220> FEATURE:
<221> NAME/KEY: CDS
<222> LOCATION: (1)..(1455)
<223> OTHER INFORMATION: SP722

<400> SEQUENCE: 3 cat cat aat ggg aca aat ggg acg atg atg caa tac ttt gaa tgg cac      48
```

-continued

| | |
|---|---|
| His His Asn Gly Thr Asn Gly Thr Met Met Gln Tyr Phe Glu Trp His<br>1               5                   10                  15 | |
| ttg cct aat gat ggg aat cac tgg aat aga tta aga gat gat gct agt<br>Leu Pro Asn Asp Gly Asn His Trp Asn Arg Leu Arg Asp Asp Ala Ser<br>            20                  25                  30 | 96 |
| aat cta aga aat aga ggt ata acc gct att tgg att ccg cct gcc tgg<br>Asn Leu Arg Asn Arg Gly Ile Thr Ala Ile Trp Ile Pro Pro Ala Trp<br>        35                  40                  45 | 144 |
| aaa ggg act tcg caa aat gat gtg ggg tat gga gcc tat gat ctt tat<br>Lys Gly Thr Ser Gln Asn Asp Val Gly Tyr Gly Ala Tyr Asp Leu Tyr<br>    50                  55                  60 | 192 |
| gat tta ggg gaa ttt aat caa aag ggg acg gtt cgt act aag tat ggg<br>Asp Leu Gly Glu Phe Asn Gln Lys Gly Thr Val Arg Thr Lys Tyr Gly<br>65                  70                  75                  80 | 240 |
| aca cgt agt caa ttg gag tct gcc atc cat gct tta aag aat aat ggc<br>Thr Arg Ser Gln Leu Glu Ser Ala Ile His Ala Leu Lys Asn Asn Gly<br>                85                  90                  95 | 288 |
| gtt caa gtt tat ggg gat gta gtg atg aac cat aaa gga gga gct gat<br>Val Gln Val Tyr Gly Asp Val Val Met Asn His Lys Gly Gly Ala Asp<br>            100                 105                 110 | 336 |
| gct aca gaa aac gtt ctt gct gtc gag gtg aat cca aat aac cgg aat<br>Ala Thr Glu Asn Val Leu Ala Val Glu Val Asn Pro Asn Asn Arg Asn<br>        115                 120                 125 | 384 |
| caa gaa ata tct ggg gac tac aca att gag gct tgg act aag ttt gat<br>Gln Glu Ile Ser Gly Asp Tyr Thr Ile Glu Ala Trp Thr Lys Phe Asp<br>    130                 135                 140 | 432 |
| ttt cca ggg agg ggt aat aca tac tca gac ttt aaa tgg cgt tgg tat<br>Phe Pro Gly Arg Gly Asn Thr Tyr Ser Asp Phe Lys Trp Arg Trp Tyr<br>145                 150                 155                 160 | 480 |
| cat ttc gat ggt gta gat tgg gat caa tca cga caa ttc caa aat cgt<br>His Phe Asp Gly Val Asp Trp Asp Gln Ser Arg Gln Phe Gln Asn Arg<br>                165                 170                 175 | 528 |
| atc tac aaa ttc cga ggt gat ggt aag gca tgg gat tgg gaa gta gat<br>Ile Tyr Lys Phe Arg Gly Asp Gly Lys Ala Trp Asp Trp Glu Val Asp<br>            180                 185                 190 | 576 |
| tcg gaa aat gga aat tat gat tat tta atg tat gca gat gta gat atg<br>Ser Glu Asn Gly Asn Tyr Asp Tyr Leu Met Tyr Ala Asp Val Asp Met<br>        195                 200                 205 | 624 |
| gat cat ccg gag gta gta aat gag ctt aga aga tgg gga gaa tgg tat<br>Asp His Pro Glu Val Val Asn Glu Leu Arg Arg Trp Gly Glu Trp Tyr<br>    210                 215                 220 | 672 |
| aca aat aca tta aat ctt gat gga ttt agg atc gat gcg gtg aag cat<br>Thr Asn Thr Leu Asn Leu Asp Gly Phe Arg Ile Asp Ala Val Lys His<br>225                 230                 235                 240 | 720 |
| att aaa tat agc ttt aca cgt gat tgg ttg acc cat gta aga aac gca<br>Ile Lys Tyr Ser Phe Thr Arg Asp Trp Leu Thr His Val Arg Asn Ala<br>                245                 250                 255 | 768 |
| acg gga aaa gaa atg ttt gct gtt gct gaa ttt tgg aaa aat gat tta<br>Thr Gly Lys Glu Met Phe Ala Val Ala Glu Phe Trp Lys Asn Asp Leu<br>            260                 265                 270 | 816 |
| ggt gcc ttg gag aac tat tta aat aaa aca aac tgg aat cat tct gtc<br>Gly Ala Leu Glu Asn Tyr Leu Asn Lys Thr Asn Trp Asn His Ser Val<br>        275                 280                 285 | 864 |
| ttt gat gtc ccc ctt cat tat aat ctt tat aac gcg tca aat agt gga<br>Phe Asp Val Pro Leu His Tyr Asn Leu Tyr Asn Ala Ser Asn Ser Gly<br>    290                 295                 300 | 912 |
| ggc aac tat gac atg gca aaa ctt ctt aat gga acg gtt gtt caa aag<br>Gly Asn Tyr Asp Met Ala Lys Leu Leu Asn Gly Thr Val Val Gln Lys<br>305                 310                 315                 320 | 960 |
| cat cca atg cat gcc gta act ttt gtg gat aat cac gat tct caa cct | 1008 |

```
His Pro Met His Ala Val Thr Phe Val Asp Asn His Asp Ser Gln Pro
                325                 330                 335 ggg gaa tca tta gaa tca ttt gta caa gaa tgg ttt aag cca ctt gct      1056
Gly Glu Ser Leu Glu Ser Phe Val Gln Glu Trp Phe Lys Pro Leu Ala
                340                 345                 350 tat gcg ctt att tta aca aga gaa caa ggc tat ccc tct gtc ttc tat      1104
Tyr Ala Leu Ile Leu Thr Arg Glu Gln Gly Tyr Pro Ser Val Phe Tyr
                355                 360                 365 ggt gac tac tat gga att cca aca cat agt gtc cca gca atg aaa gcc      1152
Gly Asp Tyr Tyr Gly Ile Pro Thr His Ser Val Pro Ala Met Lys Ala
        370                 375                 380 aag att gat cca atc tta gag gcg cgt caa aat ttt gca tat gga aca      1200
Lys Ile Asp Pro Ile Leu Glu Ala Arg Gln Asn Phe Ala Tyr Gly Thr
385                 390                 395                 400 caa cat gat tat ttt gac cat cat aat ata atc gga tgg aca cgt gaa      1248
Gln His Asp Tyr Phe Asp His His Asn Ile Ile Gly Trp Thr Arg Glu
                405                 410                 415 gga aat acc acg cat ccc aat tca gga ctt gcg act atc atg tcg gat      1296
Gly Asn Thr Thr His Pro Asn Ser Gly Leu Ala Thr Ile Met Ser Asp
                420                 425                 430 ggg cca ggg gga gag aaa tgg atg tac gta ggg caa aat aaa gca ggt      1344
Gly Pro Gly Gly Glu Lys Trp Met Tyr Val Gly Gln Asn Lys Ala Gly
                435                 440                 445 caa gtt tgg cat gac ata act gga aat aaa cca gga aca gtt acg atc      1392
Gln Val Trp His Asp Ile Thr Gly Asn Lys Pro Gly Thr Val Thr Ile
        450                 455                 460 aat gca gat gga tgg gct aat ttt tca gta aat gga gga tct gtt tcc      1440
Asn Ala Asp Gly Trp Ala Asn Phe Ser Val Asn Gly Gly Ser Val Ser
465                 470                 475                 480 att tgg gtg aaa cga                                                  1455
Ile Trp Val Lys Arg
                485

<210> SEQ ID NO 4
<211> LENGTH: 485
<212> TYPE: PRT
<213> ORGANISM: Unknown
<220> FEATURE:
<223> OTHER INFORMATION: Bacillus species

<400> SEQUENCE: 4

His His Asn Gly Thr Asn Gly Thr Met Met Gln Tyr Phe Glu Trp His
1               5                   10                  15

Leu Pro Asn Asp Gly Asn His Trp Asn Arg Leu Arg Asp Asp Ala Ser
                20                  25                  30

Asn Leu Arg Asn Arg Gly Ile Thr Ala Ile Trp Ile Pro Pro Ala Trp
            35                  40                  45

Lys Gly Thr Ser Gln Asn Asp Val Gly Tyr Gly Ala Tyr Asp Leu Tyr
        50                  55                  60

Asp Leu Gly Glu Phe Asn Gln Lys Gly Thr Val Arg Thr Lys Tyr Gly
65                  70                  75                  80

Thr Arg Ser Gln Leu Glu Ser Ala Ile His Ala Leu Lys Asn Asn Gly
                85                  90                  95

Val Gln Val Tyr Gly Asp Val Val Met Asn His Lys Gly Gly Ala Asp
                100                 105                 110

Ala Thr Glu Asn Val Leu Ala Val Glu Val Asn Pro Asn Asn Arg Asn
            115                 120                 125

Gln Glu Ile Ser Gly Asp Tyr Thr Ile Glu Ala Trp Thr Lys Phe Asp
        130                 135                 140
```

```
Phe Pro Gly Arg Gly Asn Thr Tyr Ser Asp Phe Lys Trp Arg Trp Tyr
145                 150                 155                 160

His Phe Asp Gly Val Asp Trp Asp Gln Ser Arg Gln Phe Gln Asn Arg
                165                 170                 175

Ile Tyr Lys Phe Arg Gly Asp Gly Lys Ala Trp Asp Trp Glu Val Asp
            180                 185                 190

Ser Glu Asn Gly Asn Tyr Asp Tyr Leu Met Tyr Ala Asp Val Asp Met
        195                 200                 205

Asp His Pro Glu Val Val Asn Glu Leu Arg Arg Trp Gly Glu Trp Tyr
    210                 215                 220

Thr Asn Thr Leu Asn Leu Asp Gly Phe Arg Ile Asp Ala Val Lys His
225                 230                 235                 240

Ile Lys Tyr Ser Phe Thr Arg Asp Trp Leu Thr His Val Arg Asn Ala
                245                 250                 255

Thr Gly Lys Glu Met Phe Ala Val Ala Glu Phe Trp Lys Asn Asp Leu
            260                 265                 270

Gly Ala Leu Glu Asn Tyr Leu Asn Lys Thr Asn Trp Asn His Ser Val
        275                 280                 285

Phe Asp Val Pro Leu His Tyr Asn Leu Tyr Asn Ala Ser Asn Ser Gly
    290                 295                 300

Gly Asn Tyr Asp Met Ala Lys Leu Leu Asn Gly Thr Val Val Gln Lys
305                 310                 315                 320

His Pro Met His Ala Val Thr Phe Val Asp Asn His Asp Ser Gln Pro
                325                 330                 335

Gly Glu Ser Leu Glu Ser Phe Val Gln Glu Trp Phe Lys Pro Leu Ala
            340                 345                 350

Tyr Ala Leu Ile Leu Thr Arg Glu Gln Gly Tyr Pro Ser Val Phe Tyr
        355                 360                 365

Gly Asp Tyr Tyr Gly Ile Pro Thr His Ser Val Pro Ala Met Lys Ala
    370                 375                 380

Lys Ile Asp Pro Ile Leu Glu Ala Arg Gln Asn Phe Ala Tyr Gly Thr
385                 390                 395                 400

Gln His Asp Tyr Phe Asp His His Asn Ile Ile Gly Trp Thr Arg Glu
                405                 410                 415

Gly Asn Thr Thr His Pro Asn Ser Gly Leu Ala Thr Ile Met Ser Asp
            420                 425                 430

Gly Pro Gly Gly Glu Lys Trp Met Tyr Val Gly Gln Asn Lys Ala Gly
        435                 440                 445

Gln Val Trp His Asp Ile Thr Gly Asn Lys Pro Gly Thr Val Thr Ile
    450                 455                 460

Asn Ala Asp Gly Trp Ala Asn Phe Ser Val Asn Gly Gly Ser Val Ser
465                 470                 475                 480

Ile Trp Val Lys Arg
                485
```

<210> SEQ ID NO 5
<211> LENGTH: 1548
<212> TYPE: DNA
<213> ORGANISM: Bacillus stearothermophilus
<220> FEATURE:
<221> NAME/KEY: CDS
<222> LOCATION: (1)..(1548)
<223> OTHER INFORMATION: BSG

<400> SEQUENCE: 5

```
gcc gca ccg ttt aac ggc acc atg atg cag tat ttt gaa tgg tac ttg      48
Ala Ala Pro Phe Asn Gly Thr Met Met Gln Tyr Phe Glu Trp Tyr Leu
```

```
ccg gat gat ggc acg tta tgg acc aaa gtg gcc aat gaa gcc aac aac      96
Pro Asp Asp Gly Thr Leu Trp Thr Lys Val Ala Asn Glu Ala Asn Asn
             20                  25                  30 tta tcc agc ctt ggc atc acc gct ctt tgg ctg ccg ccc gct tac aaa     144
Leu Ser Ser Leu Gly Ile Thr Ala Leu Trp Leu Pro Pro Ala Tyr Lys
         35                  40                  45 gga aca agc cgc agc gac gta ggg tac gga gta tac gac ttg tat gac     192
Gly Thr Ser Arg Ser Asp Val Gly Tyr Gly Val Tyr Asp Leu Tyr Asp
     50                  55                  60 ctc ggc gaa ttc aat caa aaa ggg acc gtc cgc aca aaa tac gga aca     240
Leu Gly Glu Phe Asn Gln Lys Gly Thr Val Arg Thr Lys Tyr Gly Thr
 65                  70                  75                  80 aaa gct caa tat ctt caa gcc att caa gcc gcc cac gcc gct gga atg     288
Lys Ala Gln Tyr Leu Gln Ala Ile Gln Ala Ala His Ala Ala Gly Met
                 85                  90                  95 caa gtg tac gcc gat gtc gtg ttc gac cat aaa ggc ggc gct gac ggc     336
Gln Val Tyr Ala Asp Val Val Phe Asp His Lys Gly Gly Ala Asp Gly
            100                 105                 110 acg gaa tgg gtg gac gcc gtc gaa gtc aat ccg tcc gac cgc aac caa     384
Thr Glu Trp Val Asp Ala Val Glu Val Asn Pro Ser Asp Arg Asn Gln
        115                 120                 125 gaa atc tcg ggc acc tat caa atc caa gca tgg acg aaa ttt gat ttt     432
Glu Ile Ser Gly Thr Tyr Gln Ile Gln Ala Trp Thr Lys Phe Asp Phe
    130                 135                 140 ccc ggg cgg ggc aac acc tac tcc agc ttt aag tgg cgc tgg tac cat     480
Pro Gly Arg Gly Asn Thr Tyr Ser Ser Phe Lys Trp Arg Trp Tyr His
145                 150                 155                 160 ttt gac ggc gtt gat tgg gac gaa agc cga aaa ttg agc cgc att tac     528
Phe Asp Gly Val Asp Trp Asp Glu Ser Arg Lys Leu Ser Arg Ile Tyr
                165                 170                 175 aaa ttc cgc ggc atc ggc aaa gcg tgg gat tgg gaa gta gac acg gaa     576
Lys Phe Arg Gly Ile Gly Lys Ala Trp Asp Trp Glu Val Asp Thr Glu
            180                 185                 190 aac gga aac tat gac tac tta atg tat gcc gac ctt gat atg gat cat     624
Asn Gly Asn Tyr Asp Tyr Leu Met Tyr Ala Asp Leu Asp Met Asp His
        195                 200                 205 ccc gaa gtc gtg acc gag ctg aaa aac tgg ggg aaa tgg tat gtc aac     672
Pro Glu Val Val Thr Glu Leu Lys Asn Trp Gly Lys Trp Tyr Val Asn
    210                 215                 220 aca acg aac att gat ggg ttc cgg ctt gat gcc gtc aag cat att aag     720
Thr Thr Asn Ile Asp Gly Phe Arg Leu Asp Ala Val Lys His Ile Lys
225                 230                 235                 240 ttc agt ttt ttt cct gat tgg ttg tcg tat gtg cgt tct cag act ggc     768
Phe Ser Phe Phe Pro Asp Trp Leu Ser Tyr Val Arg Ser Gln Thr Gly
                245                 250                 255 aag ccg cta ttt acc gtc ggg gaa tat tgg agc tat gac atc aac aag     816
Lys Pro Leu Phe Thr Val Gly Glu Tyr Trp Ser Tyr Asp Ile Asn Lys
            260                 265                 270 ttg cac aat tac att acg aaa aca gac gga acg atg tct ttg ttt gat     864
Leu His Asn Tyr Ile Thr Lys Thr Asp Gly Thr Met Ser Leu Phe Asp
        275                 280                 285 gcc ccg tta cac aac aaa ttt tat acc gct tcc aaa tca ggg ggc gca     912
Ala Pro Leu His Asn Lys Phe Tyr Thr Ala Ser Lys Ser Gly Gly Ala
    290                 295                 300 ttt gat atg cgc acg tta atg acc aat act ctc atg aaa gat caa ccg     960
Phe Asp Met Arg Thr Leu Met Thr Asn Thr Leu Met Lys Asp Gln Pro
305                 310                 315                 320 aca ttg gcc gtc acc ttc gtt gat aat cat gac acc gaa ccc ggc caa    1008
Thr Leu Ala Val Thr Phe Val Asp Asn His Asp Thr Glu Pro Gly Gln
```

```
                    325                 330                 335
gcg ctg cag tca tgg gtc gac cca tgg ttc aaa ccg ttg gct tac gcc      1056
Ala Leu Gln Ser Trp Val Asp Pro Trp Phe Lys Pro Leu Ala Tyr Ala
        340                 345                 350 ttt att cta act cgg cag gaa gga tac ccg tgc gtc ttt tat ggt gac      1104
Phe Ile Leu Thr Arg Gln Glu Gly Tyr Pro Cys Val Phe Tyr Gly Asp
355                 360                 365 tat tat ggc att cca caa tat aac att cct tcg ctg aaa agc aaa atc      1152
Tyr Tyr Gly Ile Pro Gln Tyr Asn Ile Pro Ser Leu Lys Ser Lys Ile
    370                 375                 380 gat ccg ctc ctc atc gcg cgc agg gat tat gct tac gga acg caa cat      1200
Asp Pro Leu Leu Ile Ala Arg Arg Asp Tyr Ala Tyr Gly Thr Gln His
385                 390                 395                 400 gat tat ctt gat cac tcc gac atc atc ggg tgg aca agg gaa ggg ggc      1248
Asp Tyr Leu Asp His Ser Asp Ile Ile Gly Trp Thr Arg Glu Gly Gly
            405                 410                 415 act gaa aaa cca gga tcc gga ctg gcc gca ctg atc acc gat ggg ccg      1296
Thr Glu Lys Pro Gly Ser Gly Leu Ala Ala Leu Ile Thr Asp Gly Pro
        420                 425                 430 gga gga agc aaa tgg atg tac gtt ggc aaa caa cac gct gga aaa gtg      1344
Gly Gly Ser Lys Trp Met Tyr Val Gly Lys Gln His Ala Gly Lys Val
            435                 440                 445 ttc tat gac ctt acc ggc aac cgg agt gac acc gtc acc atc aac agt      1392
Phe Tyr Asp Leu Thr Gly Asn Arg Ser Asp Thr Val Thr Ile Asn Ser
450                 455                 460 gat gga tgg ggg gaa ttc aaa gtc aat ggc ggt tcg gtt tcg gtt tgg      1440
Asp Gly Trp Gly Glu Phe Lys Val Asn Gly Gly Ser Val Ser Val Trp
465                 470                 475                 480 gtt cct aga aaa acg acc gtt tct acc atc gct cgg ccg atc aca acc      1488
Val Pro Arg Lys Thr Thr Val Ser Thr Ile Ala Arg Pro Ile Thr Thr
            485                 490                 495 cga ccg tgg act ggt gaa ttc gtc cgt tgg acc gaa cca cgg ttg gtg      1536
Arg Pro Trp Thr Gly Glu Phe Val Arg Trp Thr Glu Pro Arg Leu Val
        500                 505                 510 gca tgg cct tga                                                      1548
Ala Trp Pro
    515

<210> SEQ ID NO 6
<211> LENGTH: 515
<212> TYPE: PRT
<213> ORGANISM: Bacillus stearothermophilus

<400> SEQUENCE: 6

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
            20                  25                  30

Leu Ser Ser Leu Gly Ile Thr Ala Leu Trp Leu Pro Pro Ala Tyr Lys
        35                  40                  45

Gly Thr Ser Arg Ser Asp Val Gly Tyr Gly Val Tyr Asp Leu Tyr Asp
    50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
            100                 105                 110

Thr Glu Trp Val Asp Ala Val Glu Val Asn Pro Ser Asp Arg Asn Gln
```

```
            115                 120                 125
Glu Ile Ser Gly Thr Tyr Gln Ile Gln Ala Trp Thr Lys Phe Asp Phe
130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly Ile Gly Lys Ala Trp Asp Trp Glu Val Asp Thr Glu
                180                 185                 190

Asn Gly Asn Tyr Asp Tyr Leu Met Tyr Ala Asp Leu Asp Met Asp His
                195                 200                 205

Pro Glu Val Val Thr Glu Leu Lys Asn Trp Gly Lys Trp Tyr Val Asn
210                 215                 220

Thr Thr Asn Ile Asp Gly Phe Arg Leu Asp Ala Val Lys His Ile Lys
225                 230                 235                 240

Phe Ser Phe Phe Pro Asp Trp Leu Ser Tyr Val Arg Ser Gln Thr Gly
                245                 250                 255

Lys Pro Leu Phe Thr Val Gly Glu Tyr Trp Ser Tyr Asp Ile Asn Lys
                260                 265                 270

Leu His Asn Tyr Ile Thr Lys Thr Asp Gly Thr Met Ser Leu Phe Asp
                275                 280                 285

Ala Pro Leu His Asn Lys Phe Tyr Thr Ala Ser Lys Ser Gly Gly Ala
290                 295                 300

Phe Asp Met Arg Thr Leu Met Thr Asn Thr Leu Met Lys Asp Gln Pro
305                 310                 315                 320

Thr Leu Ala Val Thr Phe Val Asp Asn His Asp Thr Glu Pro Gly Gln
                325                 330                 335

Ala Leu Gln Ser Trp Val Asp Pro Trp Phe Lys Pro Leu Ala Tyr Ala
                340                 345                 350

Phe Ile Leu Thr Arg Gln Glu Gly Tyr Pro Cys Val Phe Tyr Gly Asp
                355                 360                 365

Tyr Tyr Gly Ile Pro Gln Tyr Asn Ile Pro Ser Leu Lys Ser Lys Ile
370                 375                 380

Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Gly
                405                 410                 415

Thr Glu Lys Pro Gly Ser Gly Leu Ala Ala Leu Ile Thr Asp Gly Pro
                420                 425                 430

Gly Gly Ser Lys Trp Met Tyr Val Gly Lys Gln His Ala Gly Lys Val
                435                 440                 445

Phe Tyr Asp Leu Thr Gly Asn Arg Ser Asp Thr Val Thr Ile Asn Ser
450                 455                 460

Asp Gly Trp Gly Glu Phe Lys Val Asn Gly Gly Ser Val Ser Val Trp
465                 470                 475                 480

Val Pro Arg Lys Thr Thr Val Ser Thr Ile Ala Arg Pro Ile Thr Thr
                485                 490                 495

Arg Pro Trp Thr Gly Glu Phe Val Arg Trp Thr Glu Pro Arg Leu Val
                500                 505                 510

Ala Trp Pro
        515

<210> SEQ ID NO 7
<211> LENGTH: 1920
```

<212> TYPE: DNA
<213> ORGANISM: Bacillus licheniformis
<220> FEATURE:
<221> NAME/KEY: CDS
<222> LOCATION: (421)..(1872)
<223> OTHER INFORMATION: TERMAMYL

<400> SEQUENCE: 7

```
cggaagattg gaagtacaaa aataagcaaa agattgtcaa tcatgtcatg agccatgcgg      60
gagacggaaa atcgtctta atgcacgata tttatgcaac gttcgcagat gctgctgaag     120
agattattaa aaagctgaaa gcaaaaggct atcaattggt aactgtatct cagcttgaag     180
aagtgaagaa gcagagaggc tattgaataa atgagtagaa gcgccatatc ggcgcttttc     240
ttttggaaga aaatataggg aaaatggtac ttgttaaaaa ttcggaatat ttatacaaca     300
tcatatgttt cacattgaaa ggggaggaga atcatgaaac aacaaaaacg gctttacgcc     360
cgattgctga cgctgttatt tgcgctcatc ttcttgctgc ctcattctgc agcagcggcg     420
```

| gca | aat | ctt | aat | ggg | acg | ctg | atg | cag | tat | ttt | gaa | tgg | tac | atg | ccc | 468 |
|---|---|---|---|---|---|---|---|---|---|---|---|---|---|---|---|---|
| Ala | Asn | Leu | Asn | Gly | Thr | Leu | Met | Gln | Tyr | Phe | Glu | Trp | Tyr | Met | Pro | |
| 1 | | | | 5 | | | | | 10 | | | | | 15 | | |

| aat | gac | ggc | caa | cat | tgg | agg | cgt | ttg | caa | aac | gac | tcg | gca | tat | ttg | 516 |
|---|---|---|---|---|---|---|---|---|---|---|---|---|---|---|---|---|
| Asn | Asp | Gly | Gln | His | Trp | Arg | Arg | Leu | Gln | Asn | Asp | Ser | Ala | Tyr | Leu | |
| | | 20 | | | | | 25 | | | | | 30 | | | | |

| gct | gaa | cac | ggt | att | act | gcc | gtc | tgg | att | ccc | ccg | gca | tat | aag | gga | 564 |
|---|---|---|---|---|---|---|---|---|---|---|---|---|---|---|---|---|
| Ala | Glu | His | Gly | Ile | Thr | Ala | Val | Trp | Ile | Pro | Pro | Ala | Tyr | Lys | Gly | |
| | | | 35 | | | | | 40 | | | | | 45 | | | |

| acg | agc | caa | gcg | gat | gtg | ggc | tac | ggt | gct | tac | gac | ctt | tat | gat | tta | 612 |
|---|---|---|---|---|---|---|---|---|---|---|---|---|---|---|---|---|
| Thr | Ser | Gln | Ala | Asp | Val | Gly | Tyr | Gly | Ala | Tyr | Asp | Leu | Tyr | Asp | Leu | |
| | 50 | | | | | 55 | | | | | 60 | | | | | |

| ggg | gag | ttt | cat | caa | aaa | ggg | acg | gtt | cgg | aca | aag | tac | ggc | aca | aaa | 660 |
|---|---|---|---|---|---|---|---|---|---|---|---|---|---|---|---|---|
| Gly | Glu | Phe | His | Gln | Lys | Gly | Thr | Val | Arg | Thr | Lys | Tyr | Gly | Thr | Lys | |
| 65 | | | | | 70 | | | | | 75 | | | | | 80 | |

| gga | gag | ctg | caa | tct | gcg | atc | aaa | agt | ctt | cat | tcc | cgc | gac | att | aac | 708 |
|---|---|---|---|---|---|---|---|---|---|---|---|---|---|---|---|---|
| Gly | Glu | Leu | Gln | Ser | Ala | Ile | Lys | Ser | Leu | His | Ser | Arg | Asp | Ile | Asn | |
| | | | | 85 | | | | | 90 | | | | | 95 | | |

| gtt | tac | ggg | gat | gtg | gtc | atc | aac | cac | aaa | ggc | ggc | gct | gat | gcg | acc | 756 |
|---|---|---|---|---|---|---|---|---|---|---|---|---|---|---|---|---|
| Val | Tyr | Gly | Asp | Val | Val | Ile | Asn | His | Lys | Gly | Gly | Ala | Asp | Ala | Thr | |
| | | 100 | | | | | 105 | | | | | 110 | | | | |

| gaa | gat | gta | acc | gcg | gtt | gaa | gtc | gat | ccc | gct | gac | cgc | aac | cgc | gta | 804 |
|---|---|---|---|---|---|---|---|---|---|---|---|---|---|---|---|---|
| Glu | Asp | Val | Thr | Ala | Val | Glu | Val | Asp | Pro | Ala | Asp | Arg | Asn | Arg | Val | |
| | | | 115 | | | | | 120 | | | | | 125 | | | |

| att | tca | gga | gaa | cac | cta | att | aaa | gcc | tgg | aca | cat | ttt | cat | ttt | ccg | 852 |
|---|---|---|---|---|---|---|---|---|---|---|---|---|---|---|---|---|
| Ile | Ser | Gly | Glu | His | Leu | Ile | Lys | Ala | Trp | Thr | His | Phe | His | Phe | Pro | |
| | 130 | | | | | 135 | | | | | 140 | | | | | |

| ggg | cgc | ggc | agc | aca | tac | agc | gat | ttt | aaa | tgg | cat | tgg | tac | cat | ttt | 900 |
|---|---|---|---|---|---|---|---|---|---|---|---|---|---|---|---|---|
| Gly | Arg | Gly | Ser | Thr | Tyr | Ser | Asp | Phe | Lys | Trp | His | Trp | Tyr | His | Phe | |
| 145 | | | | | 150 | | | | | 155 | | | | | 160 | |

| gac | gga | acc | gat | tgg | gac | gag | tcc | cga | aag | ctg | aac | cgc | atc | tat | aag | 948 |
|---|---|---|---|---|---|---|---|---|---|---|---|---|---|---|---|---|
| Asp | Gly | Thr | Asp | Trp | Asp | Glu | Ser | Arg | Lys | Leu | Asn | Arg | Ile | Tyr | Lys | |
| | | | | 165 | | | | | 170 | | | | | 175 | | |

| ttt | caa | gga | aag | gct | tgg | gat | tgg | gaa | gtt | tcc | aat | gaa | aac | ggc | aac | 996 |
|---|---|---|---|---|---|---|---|---|---|---|---|---|---|---|---|---|
| Phe | Gln | Gly | Lys | Ala | Trp | Asp | Trp | Glu | Val | Ser | Asn | Glu | Asn | Gly | Asn | |
| | | 180 | | | | | 185 | | | | | 190 | | | | |

| tat | gat | tat | ttg | atg | tat | gcc | gac | atc | gat | tat | gac | cat | cct | gat | gtc | 1044 |
|---|---|---|---|---|---|---|---|---|---|---|---|---|---|---|---|---|
| Tyr | Asp | Tyr | Leu | Met | Tyr | Ala | Asp | Ile | Asp | Tyr | Asp | His | Pro | Asp | Val | |
| | | | 195 | | | | | 200 | | | | | 205 | | | |

| gca | gca | gaa | att | aag | aga | tgg | ggc | act | tgg | tat | gcc | aat | gaa | ctg | caa | 1092 |
|---|---|---|---|---|---|---|---|---|---|---|---|---|---|---|---|---|
| Ala | Ala | Glu | Ile | Lys | Arg | Trp | Gly | Thr | Trp | Tyr | Ala | Asn | Glu | Leu | Gln | |
| | | 210 | | | | | 215 | | | | | 220 | | | | |

| ttg | gac | ggt | ttc | cgt | ctt | gat | gct | gtc | aaa | cac | att | aaa | ttt | tct | ttt | 1140 |

```
                                                                    -continued
Leu Asp Gly Phe Arg Leu Asp Ala Val Lys His Ile Lys Phe Ser Phe
225                 230                 235                 240 ttg cgg gat tgg gtt aat cat gtc agg gaa aaa acg ggg aag gaa atg    1188
Leu Arg Asp Trp Val Asn His Val Arg Glu Lys Thr Gly Lys Glu Met
                245                 250                 255 ttt acg gta gct gaa tat tgg cag aat gac ttg ggc gcg ctg gaa aac    1236
Phe Thr Val Ala Glu Tyr Trp Gln Asn Asp Leu Gly Ala Leu Glu Asn
            260                 265                 270 tat ttg aac aaa aca aat ttt aat cat tca gtg ttt gac gtg ccg ctt    1284
Tyr Leu Asn Lys Thr Asn Phe Asn His Ser Val Phe Asp Val Pro Leu
        275                 280                 285 cat tat cag ttc cat gct gca tcg aca cag gga ggc ggc tat gat atg    1332
His Tyr Gln Phe His Ala Ala Ser Thr Gln Gly Gly Gly Tyr Asp Met
    290                 295                 300 agg aaa ttg ctg aac ggt acg gtc gtt tcc aag cat ccg ttg aaa tcg    1380
Arg Lys Leu Leu Asn Gly Thr Val Val Ser Lys His Pro Leu Lys Ser
305                 310                 315                 320 gtt aca ttt gtc gat aac cat gat aca cag ccg ggg caa tcg ctt gag    1428
Val Thr Phe Val Asp Asn His Asp Thr Gln Pro Gly Gln Ser Leu Glu
                325                 330                 335 tcg act gtc caa aca tgg ttt aag ccg ctt gct tac gct ttt att ctc    1476
Ser Thr Val Gln Thr Trp Phe Lys Pro Leu Ala Tyr Ala Phe Ile Leu
            340                 345                 350 aca agg gaa tct gga tac cct cag gtt ttc tac ggg gat atg tac ggg    1524
Thr Arg Glu Ser Gly Tyr Pro Gln Val Phe Tyr Gly Asp Met Tyr Gly
        355                 360                 365 acg aaa gga gac tcc cag cgc gaa att cct gcc ttg aaa cac aaa att    1572
Thr Lys Gly Asp Ser Gln Arg Glu Ile Pro Ala Leu Lys His Lys Ile
    370                 375                 380 gaa ccg atc tta aaa gcg aga aaa cag tat gcg tac gga gca cag cat    1620
Glu Pro Ile Leu Lys Ala Arg Lys Gln Tyr Ala Tyr Gly Ala Gln His
385                 390                 395                 400 gat tat ttc gac cac cat gac att gtc ggc tgg aca agg gaa ggc gac    1668
Asp Tyr Phe Asp His His Asp Ile Val Gly Trp Thr Arg Glu Gly Asp
                405                 410                 415 agc tcg gtt gca aat tca ggt ttg gcg gca tta ata aca gac gga ccc    1716
Ser Ser Val Ala Asn Ser Gly Leu Ala Ala Leu Ile Thr Asp Gly Pro
            420                 425                 430 ggt ggg gca aag cga atg tat gtc ggc cgg caa aac gcc ggt gag aca    1764
Gly Gly Ala Lys Arg Met Tyr Val Gly Arg Gln Asn Ala Gly Glu Thr
        435                 440                 445 tgg cat gac att acc gga aac cgt tcg gag ccg gtt gtc atc aat tcg    1812
Trp His Asp Ile Thr Gly Asn Arg Ser Glu Pro Val Val Ile Asn Ser
    450                 455                 460 gaa ggc tgg gga gag ttt cac gta aac ggc ggg tcg gtt tca att tat    1860
Glu Gly Trp Gly Glu Phe His Val Asn Gly Gly Ser Val Ser Ile Tyr
465                 470                 475                 480 gtt caa aga tag aagagcagag aggacggatt tcctgaagga aatccgtttt        1912
Val Gln Arg tttatttt                                                            1920

<210> SEQ ID NO 8
<211> LENGTH: 483
<212> TYPE: PRT
<213> ORGANISM: Bacillus licheniformis

<400> SEQUENCE: 8

Ala Asn Leu Asn Gly Thr Leu Met Gln Tyr Phe Glu Trp Tyr Met Pro
1               5                   10                  15

Asn Asp Gly Gln His Trp Arg Arg Leu Gln Asn Asp Ser Ala Tyr Leu
```

-continued

```
                20                  25                  30
Ala Glu His Gly Ile Thr Ala Val Trp Ile Pro Pro Ala Tyr Lys Gly
                35                  40                  45

Thr Ser Gln Ala Asp Val Gly Tyr Gly Ala Tyr Asp Leu Tyr Asp Leu
 50                  55                  60

Gly Glu Phe His Gln Lys Gly Thr Val Arg Thr Lys Tyr Gly Thr Lys
 65                  70                  75                  80

Gly Glu Leu Gln Ser Ala Ile Lys Ser Leu His Ser Arg Asp Ile Asn
                85                  90                  95

Val Tyr Gly Asp Val Val Ile Asn His Lys Gly Gly Ala Asp Ala Thr
                100                 105                 110

Glu Asp Val Thr Ala Val Glu Val Asp Pro Ala Asp Arg Asn Arg Val
                115                 120                 125

Ile Ser Gly Glu His Leu Ile Lys Ala Trp Thr His Phe His Phe Pro
                130                 135                 140

Gly Arg Gly Ser Thr Tyr Ser Asp Phe Lys Trp His Trp Tyr His Phe
145                 150                 155                 160

Asp Gly Thr Asp Trp Asp Glu Ser Arg Lys Leu Asn Arg Ile Tyr Lys
                165                 170                 175

Phe Gln Gly Lys Ala Trp Asp Trp Glu Val Ser Asn Glu Asn Gly Asn
                180                 185                 190

Tyr Asp Tyr Leu Met Tyr Ala Asp Ile Asp Tyr Asp His Pro Asp Val
                195                 200                 205

Ala Ala Glu Ile Lys Arg Trp Gly Thr Trp Tyr Ala Asn Glu Leu Gln
                210                 215                 220

Leu Asp Gly Phe Arg Leu Asp Ala Val Lys His Ile Lys Phe Ser Phe
225                 230                 235                 240

Leu Arg Asp Trp Val Asn His Val Arg Glu Lys Thr Gly Lys Glu Met
                245                 250                 255

Phe Thr Val Ala Glu Tyr Trp Gln Asn Asp Leu Gly Ala Leu Glu Asn
                260                 265                 270

Tyr Leu Asn Lys Thr Asn Phe Asn His Ser Val Phe Asp Val Pro Leu
                275                 280                 285

His Tyr Gln Phe His Ala Ala Ser Thr Gln Gly Gly Gly Tyr Asp Met
                290                 295                 300

Arg Lys Leu Leu Asn Gly Thr Val Val Ser Lys His Pro Leu Lys Ser
305                 310                 315                 320

Val Thr Phe Val Asp Asn His Asp Thr Gln Pro Gly Gln Ser Leu Glu
                325                 330                 335

Ser Thr Val Gln Thr Trp Phe Lys Pro Leu Ala Tyr Ala Phe Ile Leu
                340                 345                 350

Thr Arg Glu Ser Gly Tyr Pro Gln Val Phe Tyr Gly Asp Met Tyr Gly
                355                 360                 365

Thr Lys Gly Asp Ser Gln Arg Glu Ile Pro Ala Leu Lys His Lys Ile
                370                 375                 380

Glu Pro Ile Leu Lys Ala Arg Lys Gln Tyr Ala Tyr Gly Ala Gln His
385                 390                 395                 400

Asp Tyr Phe Asp His His Asp Ile Val Gly Trp Thr Arg Glu Gly Asp
                405                 410                 415

Ser Ser Val Ala Asn Ser Gly Leu Ala Ala Leu Ile Thr Asp Gly Pro
                420                 425                 430

Gly Gly Ala Lys Arg Met Tyr Val Gly Arg Gln Asn Ala Gly Glu Thr
                435                 440                 445
```

```
Trp His Asp Ile Thr Gly Asn Arg Ser Glu Pro Val Val Ile Asn Ser
    450                 455                 460
Glu Gly Trp Gly Glu Phe His Val Asn Gly Ser Val Ser Ile Tyr
465                 470                 475                 480
Val Gln Arg

<210> SEQ ID NO 9
<211> LENGTH: 2084
<212> TYPE: DNA
<213> ORGANISM: Bacillus amyloliquefaciens
<220> FEATURE:
<221> NAME/KEY: CDS
<222> LOCATION: (343)..(1794)
<223> OTHER INFORMATION: BAN

<400> SEQUENCE: 9
gccccgcaca tacgaaaaga ctggctgaaa acattgagcc tttgatgact gatgatttgg      60
ctgaagaagt ggatcgattg tttgagaaaa gaagaagacc ataaaaatac cttgtctgtc     120
atcagacagg gtattttta tgctgtccag actgtccgct gtgtaaaaat aaggaataaa      180 gggggggttgt tattatttta ctgatatgta aatataatt tgtataagaa aatgagaggg     240
agaggaaaca tgattcaaaa acgaaagcgg acagtttcgt tcagacttgt gcttatgtgc    300
acgctgttat ttgtcagttt gccgattaca aaaacatcag cc gta aat ggc acg         354
                                              Val Asn Gly Thr
                                               1 ctg atg cag tat ttt gaa tgg tat acg ccg aac gac ggc cag cat tgg        402
Leu Met Gln Tyr Phe Glu Trp Tyr Thr Pro Asn Asp Gly Gln His Trp
 5              10                  15                      20 aaa cga ttg cag aat gat gcg gaa cat tta tcg gat atc gga atc act        450
Lys Arg Leu Gln Asn Asp Ala Glu His Leu Ser Asp Ile Gly Ile Thr
            25                  30                  35 gcc gtc tgg att cct ccc gca tac aaa gga ttg agc caa tcc gat aac        498
Ala Val Trp Ile Pro Pro Ala Tyr Lys Gly Leu Ser Gln Ser Asp Asn
        40                  45                  50 gga tac gga cct tat gat ttg tat gat tta gga gaa ttc cag caa aaa       546
Gly Tyr Gly Pro Tyr Asp Leu Tyr Asp Leu Gly Glu Phe Gln Gln Lys
    55                  60                  65 ggg acg gtc aga acg aaa tac ggc aca aaa tcg gag ctt caa gat gcg       594
Gly Thr Val Arg Thr Lys Tyr Gly Thr Lys Ser Glu Leu Gln Asp Ala
70                  75                  80 atc ggc tca ctg cat tcc cgg aac gtc caa gta tac gga gat gtg gtt       642
Ile Gly Ser Leu His Ser Arg Asn Val Gln Val Tyr Gly Asp Val Val
85                  90                  95                 100 ttg aat cat aag gct ggt gct gat gca aca gaa gat gta act gcc gtc       690
Leu Asn His Lys Ala Gly Ala Asp Ala Thr Glu Asp Val Thr Ala Val
            105                 110                 115 gaa gtc aat ccg gcc aat aga aat cag gaa act tcg gag gaa tat caa       738
Glu Val Asn Pro Ala Asn Arg Asn Gln Glu Thr Ser Glu Glu Tyr Gln
        120                 125                 130 atc aaa gcg tgg acg gat ttt cgt ttt ccg ggc cgt gga aac acg tac       786
Ile Lys Ala Trp Thr Asp Phe Arg Phe Pro Gly Arg Gly Asn Thr Tyr
    135                 140                 145 agt gat ttt aaa tgg cat tgg tat cat ttc gac gga gcg gac tgg gat       834
Ser Asp Phe Lys Trp His Trp Tyr His Phe Asp Gly Ala Asp Trp Asp
150                 155                 160 gaa tcc cgg aag atc agc cgc atc ttt aag ttt cgt ggg gaa gga aaa       882
Glu Ser Arg Lys Ile Ser Arg Ile Phe Lys Phe Arg Gly Glu Gly Lys
165                 170                 175                 180 gcg tgg gat tgg gaa gta tca agt gaa aac ggc aac tat gac tat tta       930
Ala Trp Asp Trp Glu Val Ser Ser Glu Asn Gly Asn Tyr Asp Tyr Leu
```

```
                    185                 190                 195
atg tat gct gat gtt gac tac gac cac cct gat gtc gtg gca gag aca      978
Met Tyr Ala Asp Val Asp Tyr Asp His Pro Asp Val Val Ala Glu Thr
        200                 205                 210 aaa aaa tgg ggt atc tgg tat gcg aat gaa ctg tca tta gac ggc ttc     1026
Lys Lys Trp Gly Ile Trp Tyr Ala Asn Glu Leu Ser Leu Asp Gly Phe
            215                 220                 225 cgt att gat gcc gcc aaa cat att aaa ttt tca ttt ctg cgt gat tgg     1074
Arg Ile Asp Ala Ala Lys His Ile Lys Phe Ser Phe Leu Arg Asp Trp
    230                 235                 240 gtt cag gcg gtc aga cag gcg acg gga aaa gaa atg ttt acg gtt gcg     1122
Val Gln Ala Val Arg Gln Ala Thr Gly Lys Glu Met Phe Thr Val Ala
245                 250                 255                 260 gag tat tgg cag aat aat gcc ggg aaa ctc gaa aac tac ttg aat aaa     1170
Glu Tyr Trp Gln Asn Asn Ala Gly Lys Leu Glu Asn Tyr Leu Asn Lys
                265                 270                 275 aca agc ttt aat caa tcc gtg ttt gat gtt ccg ctt cat ttc aat tta     1218
Thr Ser Phe Asn Gln Ser Val Phe Asp Val Pro Leu His Phe Asn Leu
            280                 285                 290 cag gcg gct tcc tca caa gga ggc gga tat gat atg agg cgt ttg ctg     1266
Gln Ala Ala Ser Ser Gln Gly Gly Gly Tyr Asp Met Arg Arg Leu Leu
        295                 300                 305 gac ggt acc gtt gtg tcc agg cat ccg gaa aag gcg gtt aca ttt gtt     1314
Asp Gly Thr Val Val Ser Arg His Pro Glu Lys Ala Val Thr Phe Val
    310                 315                 320 gaa aat cat gac aca cag ccg gga cag tca ttg gaa tcg aca gtc caa     1362
Glu Asn His Asp Thr Gln Pro Gly Gln Ser Leu Glu Ser Thr Val Gln
325                 330                 335                 340 act tgg ttt aaa ccg ctt gca tac gcc ttt att ttg aca aga gaa tcc     1410
Thr Trp Phe Lys Pro Leu Ala Tyr Ala Phe Ile Leu Thr Arg Glu Ser
                345                 350                 355 ggt tat cct cag gtg ttc tat ggg gat atg tac ggg aca aaa ggg aca     1458
Gly Tyr Pro Gln Val Phe Tyr Gly Asp Met Tyr Gly Thr Lys Gly Thr
            360                 365                 370 tcg cca aag gaa att ccc tca ctg aaa gat aat ata gag ccg att tta     1506
Ser Pro Lys Glu Ile Pro Ser Leu Lys Asp Asn Ile Glu Pro Ile Leu
        375                 380                 385 aaa gcg cgt aag gag tac gca tac ggg ccc cag cac gat tat att gac     1554
Lys Ala Arg Lys Glu Tyr Ala Tyr Gly Pro Gln His Asp Tyr Ile Asp
    390                 395                 400 cac ccg gat gtg atc gga tgg acg agg gaa ggt gac agc tcc gcc gcc     1602
His Pro Asp Val Ile Gly Trp Thr Arg Glu Gly Asp Ser Ser Ala Ala
405                 410                 415                 420 aaa tca ggt ttg gcc gct tta atc acg gac gga ccc ggc gga tca aag     1650
Lys Ser Gly Leu Ala Ala Leu Ile Thr Asp Gly Pro Gly Gly Ser Lys
                425                 430                 435 cgg atg tat gcc ggc ctg aaa aat gcc ggc gag aca tgg tat gac ata     1698
Arg Met Tyr Ala Gly Leu Lys Asn Ala Gly Glu Thr Trp Tyr Asp Ile
            440                 445                 450 acg ggc aac cgt tca gat act gta aaa atc gga tct gac ggc tgg gga     1746
Thr Gly Asn Arg Ser Asp Thr Val Lys Ile Gly Ser Asp Gly Trp Gly
        455                 460                 465 gag ttt cat gta aac gat ggg tcc gtc tcc att tat gtt cag aaa taa     1794
Glu Phe His Val Asn Asp Gly Ser Val Ser Ile Tyr Val Gln Lys
    470                 475                 480 ggtaataaaa aaacacctcc aagctgagtg cgggtatcag cttggaggtg cgtttatttt    1854
ttcagccgta tgacaaggtc ggcatcaggt gtgacaaata cggtatgctg gctgtcatag    1914
gtgacaaatc cgggttttgc gccgtttggc ttttcacat gtctgatttt tgtataatca    1974
```

```
acaggcacgg agccggaatc tttcgccttg gaaaaataag cggcgatcgt agctgcttcc    2034
aatatggatt gttcatcggg atcgctgctt ttaatcacaa cgtgggatcc               2084
```

<210> SEQ ID NO 10
<211> LENGTH: 483
<212> TYPE: PRT
<213> ORGANISM: Bacillus amyloliquefaciens

<400> SEQUENCE: 10

```
Val Asn Gly Thr Leu Met Gln Tyr Phe Glu Trp Tyr Thr Pro Asn Asp
1               5                   10                  15

Gly Gln His Trp Lys Arg Leu Gln Asn Asp Ala Glu His Leu Ser Asp
            20                  25                  30

Ile Gly Ile Thr Ala Val Trp Ile Pro Pro Ala Tyr Lys Gly Leu Ser
        35                  40                  45

Gln Ser Asp Asn Gly Tyr Gly Pro Tyr Asp Leu Tyr Asp Leu Gly Glu
    50                  55                  60

Phe Gln Gln Lys Gly Thr Val Arg Thr Lys Tyr Gly Thr Lys Ser Glu
65                  70                  75                  80

Leu Gln Asp Ala Ile Gly Ser Leu His Ser Arg Asn Val Gln Val Tyr
                85                  90                  95

Gly Asp Val Val Leu Asn His Lys Ala Gly Ala Asp Ala Thr Glu Asp
            100                 105                 110

Val Thr Ala Val Glu Val Asn Pro Ala Asn Arg Asn Gln Glu Thr Ser
        115                 120                 125

Glu Glu Tyr Gln Ile Lys Ala Trp Thr Asp Phe Arg Phe Pro Gly Arg
    130                 135                 140

Gly Asn Thr Tyr Ser Asp Phe Lys Trp His Trp Tyr His Phe Asp Gly
145                 150                 155                 160

Ala Asp Trp Asp Glu Ser Arg Lys Ile Ser Arg Ile Phe Lys Phe Arg
                165                 170                 175

Gly Glu Gly Lys Ala Trp Asp Trp Glu Val Ser Ser Glu Asn Gly Asn
            180                 185                 190

Tyr Asp Tyr Leu Met Tyr Ala Asp Val Asp Tyr Asp His Pro Asp Val
        195                 200                 205

Val Ala Glu Thr Lys Lys Trp Gly Ile Trp Tyr Ala Asn Glu Leu Ser
    210                 215                 220

Leu Asp Gly Phe Arg Ile Asp Ala Ala Lys His Ile Lys Phe Ser Phe
225                 230                 235                 240

Leu Arg Asp Trp Val Gln Ala Val Arg Gln Ala Thr Gly Lys Glu Met
                245                 250                 255

Phe Thr Val Ala Glu Tyr Trp Gln Asn Asn Ala Gly Lys Leu Glu Asn
            260                 265                 270

Tyr Leu Asn Lys Thr Ser Phe Asn Gln Ser Val Phe Asp Val Pro Leu
        275                 280                 285

His Phe Asn Leu Gln Ala Ala Ser Ser Gln Gly Gly Gly Tyr Asp Met
    290                 295                 300

Arg Arg Leu Leu Asp Gly Thr Val Val Ser Arg His Pro Glu Lys Ala
305                 310                 315                 320

Val Thr Phe Val Glu Asn His Asp Thr Gln Pro Gly Gln Ser Leu Glu
                325                 330                 335

Ser Thr Val Gln Thr Trp Phe Lys Pro Leu Ala Tyr Ala Phe Ile Leu
            340                 345                 350

Thr Arg Glu Ser Gly Tyr Pro Gln Val Phe Tyr Gly Asp Met Tyr Gly
        355                 360                 365
```

-continued

```
Thr Lys Gly Thr Ser Pro Lys Glu Ile Pro Ser Leu Lys Asp Asn Ile
    370                 375                 380

Glu Pro Ile Leu Lys Ala Arg Lys Glu Tyr Ala Tyr Gly Pro Gln His
385                 390                 395                 400

Asp Tyr Ile Asp His Pro Asp Val Ile Gly Trp Thr Arg Glu Gly Asp
                405                 410                 415

Ser Ser Ala Ala Lys Ser Gly Leu Ala Ala Leu Ile Thr Asp Gly Pro
            420                 425                 430

Gly Gly Ser Lys Arg Met Tyr Ala Gly Leu Lys Asn Ala Gly Glu Thr
        435                 440                 445

Trp Tyr Asp Ile Thr Gly Asn Arg Ser Asp Thr Val Lys Ile Gly Ser
    450                 455                 460

Asp Gly Trp Gly Glu Phe His Val Asn Asp Gly Ser Val Ser Ile Tyr
465                 470                 475                 480

Val Gln Lys

<210> SEQ ID NO 11
<211> LENGTH: 1458
<212> TYPE: DNA
<213> ORGANISM: Unknown
<220> FEATURE:
<223> OTHER INFORMATION: Bacillus species
<220> FEATURE:
<221> NAME/KEY: CDS
<222> LOCATION: (1)..(1458)
<223> OTHER INFORMATION: AA560

<400> SEQUENCE: 11 cac cat aat ggt acg aac ggc aca atg atg cag tac ttt gaa tgg tat      48
His His Asn Gly Thr Asn Gly Thr Met Met Gln Tyr Phe Glu Trp Tyr
1               5                  10                  15 cta cca aat gac gga aac cat tgg aat aga tta agg tct gat gca agt      96
Leu Pro Asn Asp Gly Asn His Trp Asn Arg Leu Arg Ser Asp Ala Ser
                20                  25                  30 aac cta aaa gat aaa ggg atc tca gcg gtt tgg att cct cct gca tgg    144
Asn Leu Lys Asp Lys Gly Ile Ser Ala Val Trp Ile Pro Pro Ala Trp
            35                  40                  45 aag ggt gcc tct caa aat gat gtg ggg tat ggt gct tat gat ctg tat    192
Lys Gly Ala Ser Gln Asn Asp Val Gly Tyr Gly Ala Tyr Asp Leu Tyr
        50                  55                  60 gat tta gga gaa ttc aat caa aaa gga acc att cgt aca aaa tat gga    240
Asp Leu Gly Glu Phe Asn Gln Lys Gly Thr Ile Arg Thr Lys Tyr Gly
65                  70                  75                  80 acg cgc aat cag tta caa gct gca gtt aac gcc ttg aaa agt aat gga    288
Thr Arg Asn Gln Leu Gln Ala Ala Val Asn Ala Leu Lys Ser Asn Gly
                85                  90                  95 att caa gtg tat ggc gat gtt gta atg aat cat aaa ggg gga gca gac    336
Ile Gln Val Tyr Gly Asp Val Val Met Asn His Lys Gly Gly Ala Asp
            100                 105                 110 gct acc gaa atg gtt agg gca gtt gaa gta aac ccg aat aat aga aat    384
Ala Thr Glu Met Val Arg Ala Val Glu Val Asn Pro Asn Asn Arg Asn
        115                 120                 125 caa gaa gtg tcc ggt gaa tat aca att gag gct tgg aca aag ttt gac    432
Gln Glu Val Ser Gly Glu Tyr Thr Ile Glu Ala Trp Thr Lys Phe Asp
    130                 135                 140 ttt cca gga cga ggt aat act cat tca aac ttc aaa tgg aga tgg tat    480
Phe Pro Gly Arg Gly Asn Thr His Ser Asn Phe Lys Trp Arg Trp Tyr
145                 150                 155                 160 cac ttt gat gga gta gat tgg gat cag tca cgt aag ctg aac aat cga    528
His Phe Asp Gly Val Asp Trp Asp Gln Ser Arg Lys Leu Asn Asn Arg
```

-continued

```
                    165                 170                 175
att tat aaa ttt aga ggt gat gga aaa ggg tgg gat tgg gaa gtc gat       576
Ile Tyr Lys Phe Arg Gly Asp Gly Lys Gly Trp Asp Trp Glu Val Asp
        180                 185                 190 aca gaa aac ggt aac tat gat tac cta atg tat gca gat att gac atg       624
Thr Glu Asn Gly Asn Tyr Asp Tyr Leu Met Tyr Ala Asp Ile Asp Met
            195                 200                 205 gat cac cca gag gta gtg aat gag cta aga aat tgg ggt gtt tgg tat       672
Asp His Pro Glu Val Val Asn Glu Leu Arg Asn Trp Gly Val Trp Tyr
210                 215                 220 acg aat aca tta ggc ctt gat ggt ttt aga ata gat gca gta aaa cat       720
Thr Asn Thr Leu Gly Leu Asp Gly Phe Arg Ile Asp Ala Val Lys His
225                 230                 235                 240 ata aaa tac agc ttt act cgt gat tgg att aat cat gtt aga agt gca       768
Ile Lys Tyr Ser Phe Thr Arg Asp Trp Ile Asn His Val Arg Ser Ala
                245                 250                 255 act ggc aaa aat atg ttt gcg gtt gcg gaa ttt tgg aaa aat gat tta       816
Thr Gly Lys Asn Met Phe Ala Val Ala Glu Phe Trp Lys Asn Asp Leu
            260                 265                 270 ggt gct att gaa aac tat tta aac aaa aca aac tgg aac cat tca gtc       864
Gly Ala Ile Glu Asn Tyr Leu Asn Lys Thr Asn Trp Asn His Ser Val
        275                 280                 285 ttt gat gtt ccg ctg cac tat aac ctc tat aat gct tca aaa agc gga       912
Phe Asp Val Pro Leu His Tyr Asn Leu Tyr Asn Ala Ser Lys Ser Gly
    290                 295                 300 ggg aat tat gat atg agg caa ata ttt aat ggt aca gtc gtg caa aga       960
Gly Asn Tyr Asp Met Arg Gln Ile Phe Asn Gly Thr Val Val Gln Arg
305                 310                 315                 320 cat cca atg cat gct gtt aca ttt gtt gat aat cat gat tcg caa cct      1008
His Pro Met His Ala Val Thr Phe Val Asp Asn His Asp Ser Gln Pro
                325                 330                 335 gaa gaa gct tta gag tct ttt gtt gaa gaa tgg ttc aaa cca tta gcg      1056
Glu Glu Ala Leu Glu Ser Phe Val Glu Glu Trp Phe Lys Pro Leu Ala
            340                 345                 350 tat gct ttg aca tta aca cgt gaa caa ggc tac cct tct gta ttt tat      1104
Tyr Ala Leu Thr Leu Thr Arg Glu Gln Gly Tyr Pro Ser Val Phe Tyr
        355                 360                 365 gga gat tat tat ggc att cca acg cat ggt gta cca gcg atg aaa tcg      1152
Gly Asp Tyr Tyr Gly Ile Pro Thr His Gly Val Pro Ala Met Lys Ser
    370                 375                 380 aaa att gac ccg att cta gaa gcg cgt caa aag tat gca tat gga aga      1200
Lys Ile Asp Pro Ile Leu Glu Ala Arg Gln Lys Tyr Ala Tyr Gly Arg
385                 390                 395                 400 caa aat gac tac tta gac cat cat aat atc atc ggt tgg aca cgt gaa      1248
Gln Asn Asp Tyr Leu Asp His His Asn Ile Ile Gly Trp Thr Arg Glu
                405                 410                 415 ggg aat aca gca cac ccc aac tcc ggt tta gct act atc atg tcc gat      1296
Gly Asn Thr Ala His Pro Asn Ser Gly Leu Ala Thr Ile Met Ser Asp
            420                 425                 430 ggg gca gga gga aat aag tgg atg ttt gtt ggg cgt aat aaa gct ggt      1344
Gly Ala Gly Gly Asn Lys Trp Met Phe Val Gly Arg Asn Lys Ala Gly
        435                 440                 445 caa gtt tgg acc gat atc act gga aat cgt gca ggt act gtt acg att      1392
Gln Val Trp Thr Asp Ile Thr Gly Asn Arg Ala Gly Thr Val Thr Ile
    450                 455                 460 aat gct gat gga tgg ggt aat ttt tct gta aat gga gga tca gtt tct      1440
Asn Ala Asp Gly Trp Gly Asn Phe Ser Val Asn Gly Gly Ser Val Ser
465                 470                 475                 480 att tgg gta aac aaa taa                                              1458
Ile Trp Val Asn Lys
```

<210> SEQ ID NO 12
<211> LENGTH: 485
<212> TYPE: PRT
<213> ORGANISM: Unknown
<220> FEATURE:
<223> OTHER INFORMATION: Bacillus species

<400> SEQUENCE: 12

```
His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Ser Asp Ala Ser
            20                  25                  30

Asn Leu Lys Asp Lys Gly Ile Ser Ala Val Trp Ile Pro Pro Ala Trp
        35                  40                  45

Lys Gly Ala Ser Gln Asn Asp Val Gly Tyr Gly Ala Tyr Asp Leu Tyr
50                  55                  60

Asp Leu Gly Glu Phe Asn Gln Lys Gly Thr Ile Arg Thr Lys Tyr Gly
65                  70                  75                  80

Thr Arg Asn Gln Leu Gln Ala Ala Val Asn Ala Leu Lys Ser Asn Gly
                85                  90                  95

Ile Gln Val Tyr Gly Asp Val Val Met Asn His Lys Gly Gly Ala Asp
            100                 105                 110

Ala Thr Glu Met Val Arg Ala Val Glu Val Asn Pro Asn Asn Arg Asn
        115                 120                 125

Gln Glu Val Ser Gly Glu Tyr Thr Ile Glu Ala Trp Thr Lys Phe Asp
130                 135                 140

Phe Pro Gly Arg Gly Asn Thr His Ser Asn Phe Lys Trp Arg Trp Tyr
145                 150                 155                 160

His Phe Asp Gly Val Asp Trp Asp Gln Ser Arg Lys Leu Asn Asn Arg
                165                 170                 175

Ile Tyr Lys Phe Arg Gly Asp Gly Lys Gly Trp Asp Trp Glu Val Asp
            180                 185                 190

Thr Glu Asn Gly Asn Tyr Asp Tyr Leu Met Tyr Ala Asp Ile Asp Met
        195                 200                 205

Asp His Pro Glu Val Val Asn Glu Leu Arg Asn Trp Gly Val Trp Tyr
210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Ile Asn His Val Arg Ser Ala
                245                 250                 255

Thr Gly Lys Asn Met Phe Ala Val Ala Glu Phe Trp Lys Asn Asp Leu
            260                 265                 270

Gly Ala Ile Glu Asn Tyr Leu Asn Lys Thr Asn Trp Asn His Ser Val
        275                 280                 285

Phe Asp Val Pro Leu His Tyr Asn Leu Tyr Asn Ala Ser Lys Ser Gly
290                 295                 300

Gly Asn Tyr Asp Met Arg Gln Ile Phe Asn Gly Thr Val Val Gln Arg
305                 310                 315                 320

His Pro Met His Ala Val Thr Phe Val Asp Asn His Asp Ser Gln Pro
                325                 330                 335

Glu Glu Ala Leu Glu Ser Phe Val Glu Glu Trp Phe Lys Pro Leu Ala
            340                 345                 350

Tyr Ala Leu Thr Leu Thr Arg Glu Gln Gly Tyr Pro Ser Val Phe Tyr
        355                 360                 365
```

```
Gly Asp Tyr Tyr Gly Ile Pro Thr His Gly Val Pro Ala Met Lys Ser
    370                 375                 380

Lys Ile Asp Pro Ile Leu Glu Ala Arg Gln Lys Tyr Ala Tyr Gly Arg
385                 390                 395                 400

Gln Asn Asp Tyr Leu Asp His His Asn Ile Ile Gly Trp Thr Arg Glu
                405                 410                 415

Gly Asn Thr Ala His Pro Asn Ser Gly Leu Ala Thr Ile Met Ser Asp
            420                 425                 430

Gly Ala Gly Gly Asn Lys Trp Met Phe Val Gly Arg Asn Lys Ala Gly
            435                 440                 445

Gln Val Trp Thr Asp Ile Thr Gly Asn Arg Ala Gly Thr Val Thr Ile
    450                 455                 460

Asn Ala Asp Gly Trp Gly Asn Phe Ser Val Asn Gly Gly Ser Val Ser
465                 470                 475                 480

Ile Trp Val Asn Lys
                485

<210> SEQ ID NO 13
<211> LENGTH: 485
<212> TYPE: PRT
<213> ORGANISM: Unknown
<220> FEATURE:
<223> OTHER INFORMATION: Bacillus species

<400> SEQUENCE: 13

His His Asn Gly Thr Asn Gly Thr Met Met Gln Tyr Phe Glu Trp Tyr
1               5                   10                  15

Leu Pro Asn Asp Gly Asn His Trp Asn Arg Leu Asn Ser Asp Ala Ser
                20                  25                  30

Asn Leu Lys Ser Lys Gly Ile Thr Ala Val Trp Ile Pro Pro Ala Trp
            35                  40                  45

Lys Gly Ala Ser Gln Asn Asp Val Gly Tyr Gly Ala Tyr Asp Leu Tyr
        50                  55                  60

Asp Leu Gly Glu Phe Asn Gln Lys Gly Thr Val Arg Thr Lys Tyr Gly
65                  70                  75                  80

Thr Arg Ser Gln Leu Gln Ala Ala Val Thr Ser Leu Lys Asn Asn Gly
                85                  90                  95

Ile Gln Val Tyr Gly Asp Val Val Met Asn His Lys Gly Gly Ala Asp
                100                 105                 110

Ala Thr Glu Met Val Arg Ala Val Glu Val Asn Pro Asn Asn Arg Asn
            115                 120                 125

Gln Glu Val Thr Gly Glu Tyr Thr Ile Glu Ala Trp Thr Arg Phe Asp
        130                 135                 140

Phe Pro Gly Arg Gly Asn Thr His Ser Ser Phe Lys Trp Arg Trp Tyr
145                 150                 155                 160

His Phe Asp Gly Val Asp Trp Asp Gln Ser Arg Arg Leu Asn Asn Arg
                165                 170                 175

Ile Tyr Lys Phe Arg Gly His Gly Lys Ala Trp Asp Trp Glu Val Asp
            180                 185                 190

Thr Glu Asn Gly Asn Tyr Asp Tyr Leu Met Tyr Ala Asp Ile Asp Met
        195                 200                 205

Asp His Pro Glu Val Val Asn Glu Leu Arg Asn Trp Gly Val Trp Tyr
    210                 215                 220

Thr Asn Thr Leu Gly Leu Asp Gly Phe Arg Ile Asp Ala Val Lys His
225                 230                 235                 240
```

```
Ile Lys Tyr Ser Phe Thr Arg Asp Trp Ile Asn His Val Arg Ser Ala
            245                 250                 255

Thr Gly Lys Asn Met Phe Ala Val Ala Glu Phe Trp Lys Asn Asp Leu
            260                 265                 270

Gly Ala Ile Glu Asn Tyr Leu Gln Lys Thr Asn Trp Asn His Ser Val
            275                 280                 285

Phe Asp Val Pro Leu His Tyr Asn Leu Tyr Asn Ala Ser Lys Ser Gly
            290                 295                 300

Gly Asn Tyr Asp Met Arg Asn Ile Phe Asn Gly Thr Val Val Gln Arg
305                 310                 315                 320

His Pro Ser His Ala Val Thr Phe Val Asp Asn His Asp Ser Gln Pro
                325                 330                 335

Glu Glu Ala Leu Glu Ser Phe Val Glu Glu Trp Phe Lys Pro Leu Ala
                340                 345                 350

Tyr Ala Leu Thr Leu Thr Arg Glu Gln Gly Tyr Pro Ser Val Phe Tyr
                355                 360                 365

Gly Asp Tyr Tyr Gly Ile Pro Thr His Gly Val Pro Ala Met Arg Ser
            370                 375                 380

Lys Ile Asp Pro Ile Leu Glu Ala Arg Gln Lys Tyr Ala Tyr Gly Lys
385                 390                 395                 400

Gln Asn Asp Tyr Leu Asp His His Asn Ile Ile Gly Trp Thr Arg Glu
                405                 410                 415

Gly Asn Thr Ala His Pro Asn Ser Gly Leu Ala Thr Ile Met Ser Asp
                420                 425                 430

Gly Ala Gly Gly Ser Lys Trp Met Phe Val Gly Arg Asn Lys Ala Gly
            435                 440                 445

Gln Val Trp Ser Asp Ile Thr Gly Asn Arg Thr Gly Thr Val Thr Ile
450                 455                 460

Asn Ala Asp Gly Trp Gly Asn Phe Ser Val Asn Gly Gly Ser Val Ser
465                 470                 475                 480

Ile Trp Val Asn Lys
            485
```